United States Patent
Simpson et al.

(10) Patent No.: US 10,561,352 B2
(45) Date of Patent: *Feb. 18, 2020

(54) PARTICLE-CONTAINING MEMBRANE AND PARTICULATE ELECTRODE FOR ANALYTE SENSORS

(71) Applicant: DexCom, Inc., San Diego, CA (US)

(72) Inventors: Peter C. Simpson, Cardiff, CA (US); Robert J. Boock, Carlsbad, CA (US); Matthew D. Wightlin, San Diego, CA (US); Mark C. Shults, Madison, WI (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/027,103

(22) Filed: Jul. 3, 2018

(65) Prior Publication Data

US 2018/0317819 A1 Nov. 8, 2018

Related U.S. Application Data

(63) Continuation of application No. 15/711,863, filed on Sep. 21, 2017, now Pat. No. 10,028,684, which is a (Continued)

(51) Int. Cl.
*A61B 5/05* (2006.01)
*A61B 5/1473* (2006.01)
(Continued)

(52) U.S. Cl.
CPC ........ *A61B 5/1473* (2013.01); *A61B 5/14532* (2013.01); *A61B 5/14546* (2013.01);
(Continued)

(58) Field of Classification Search
CPC ............. A61B 5/1473; A61B 5/14532; A61B 5/14865; A61B 5/14546; A61B 5/6848; A61B 2562/028
See application file for complete search history.

(56) References Cited

U.S. PATENT DOCUMENTS 2,719,797 A 10/1955 Rosenblatt et al.
2,830,020 A 4/1958 Christmann et al.
(Continued)

FOREIGN PATENT DOCUMENTS

EP 0 098 592 1/1984
EP 0 127 958 12/1984
(Continued)

OTHER PUBLICATIONS

US 7,530,950 B2, 05/2009, Brister et al. (withdrawn)
(Continued)

*Primary Examiner* — Christian Jang
(74) *Attorney, Agent, or Firm* — Knobbe Martens Olson & Bear, LLP

(57) ABSTRACT

Systems and methods of use involving sensors having a particle-containing domain are provided for continuous analyte measurement in a host. In some embodiments, a continuous analyte measurement system is configured to be wholly, transcutaneously, intravascularly or extracorporeally implanted.

13 Claims, 5 Drawing Sheets

Related U.S. Application Data continuation of application No. 14/887,232, filed on Oct. 19, 2015, now abandoned, which is a continuation of application No. 13/907,507, filed on May 31, 2013, now Pat. No. 9,339,222, which is a continuation of application No. 12/562,011, filed on Sep. 17, 2009, now Pat. No. 8,560,039.

(60) Provisional application No. 61/098,667, filed on Sep. 19, 2008.

(51) Int. Cl.
 A61B 5/145 (2006.01)
 A61B 5/00 (2006.01)
 A61B 5/1486 (2006.01)

(52) U.S. Cl.
 CPC ........ *A61B 5/14865* (2013.01); *A61B 5/6848* (2013.01); *A61B 2562/028* (2013.01)

(56) References Cited

U.S. PATENT DOCUMENTS

| | | |
|---|---|---|
| 3,210,578 A | 10/1965 | Sherer |
| 3,219,533 A | 11/1965 | Mullins |
| 3,220,960 A | 11/1965 | Drahoslav et al. |
| 3,381,371 A | 5/1968 | Russell |
| 3,562,352 A | 2/1971 | Nyilas |
| 3,607,329 A | 9/1971 | Manjikian |
| 3,746,588 A | 7/1973 | Brown |
| 3,826,244 A | 7/1974 | Salcman et al. |
| 3,898,984 A | 8/1975 | Mandel et al. |
| 3,943,918 A | 3/1976 | Lewis |
| 3,957,613 A | 5/1976 | Macur |
| 3,979,274 A | 9/1976 | Newman |
| 4,052,754 A | 10/1977 | Homsy |
| 4,136,250 A | 1/1979 | Mueller et al. |
| 4,253,469 A | 3/1981 | Aslan |
| 4,256,561 A | 3/1981 | Schindler et al. |
| 4,260,725 A | 4/1981 | Keogh et al. |
| 4,267,145 A | 5/1981 | Wysong |
| 4,292,423 A | 9/1981 | Kaufmann et al. |
| 4,374,013 A | 2/1983 | Enfors |
| 4,403,984 A | 9/1983 | Ash et al. |
| 4,415,666 A | 11/1983 | D'Orazio et al. |
| 4,431,507 A | 2/1984 | Nankai et al. |
| 4,442,841 A | 4/1984 | Uehara et al. |
| 4,454,295 A | 6/1984 | Wittmann et al. |
| 4,477,314 A | 10/1984 | Richter et al. |
| 4,482,666 A | 11/1984 | Reeves |
| 4,484,987 A | 11/1984 | Gough |
| 4,493,714 A | 1/1985 | Ueda et al. |
| 4,494,950 A | 1/1985 | Fischell |
| 4,527,999 A | 7/1985 | Lee |
| 4,545,382 A | 10/1985 | Higgins et al. |
| 4,554,927 A | 11/1985 | Fussell |
| 4,583,976 A | 4/1986 | Ferguson |
| 4,602,922 A | 7/1986 | Cabasso et al. |
| 4,632,968 A | 12/1986 | Yokota et al. |
| 4,644,046 A | 2/1987 | Yamada |
| 4,647,643 A | 3/1987 | Zdrahala et al. |
| 4,650,547 A | 3/1987 | Gough |
| 4,655,880 A | 4/1987 | Liu |
| 4,671,288 A | 6/1987 | Gough |
| 4,672,970 A | 6/1987 | Uchida et al. |
| 4,680,268 A | 7/1987 | Clark, Jr. |
| 4,684,538 A | 8/1987 | Klemarczyk |
| 4,685,463 A | 8/1987 | Williams |
| 4,686,137 A | 8/1987 | Ward, Jr. et al. |
| 4,689,149 A | 8/1987 | Kanno et al. |
| 4,703,756 A | 11/1987 | Gough et al. |
| 4,711,245 A | 12/1987 | Higgins |
| 4,721,677 A | 1/1988 | Clark |
| 4,726,381 A | 2/1988 | Jones |
| 4,731,726 A | 3/1988 | Allen |
| 4,739,380 A | 4/1988 | Lauks et al. |
| 4,750,496 A | 6/1988 | Reinhart et al. |
| 4,757,022 A | 7/1988 | Shults et al. |
| 4,763,658 A | 8/1988 | Jones |
| 4,777,205 A | 10/1988 | La Scola et al. |
| 4,781,733 A | 11/1988 | Babcock et al. |
| 4,786,657 A | 11/1988 | Hammar et al. |
| 4,793,555 A | 12/1988 | Lee et al. |
| 4,795,542 A | 1/1989 | Ross et al. |
| 4,805,624 A | 2/1989 | Yao et al. |
| 4,805,625 A | 2/1989 | Wyler |
| 4,813,424 A | 3/1989 | Wilkins |
| 4,822,336 A | 4/1989 | DiTraglia |
| 4,831,070 A | 5/1989 | McInally et al. |
| 4,832,034 A | 5/1989 | Pizziconi |
| 4,852,573 A | 8/1989 | Kennedy |
| 4,858,615 A | 8/1989 | Meinema |
| 4,861,830 A | 8/1989 | Ward, Jr. |
| 4,871,440 A | 10/1989 | Nagata et al. |
| 4,880,883 A | 11/1989 | Grasel et al. |
| 4,883,057 A | 11/1989 | Broderick |
| 4,886,740 A | 12/1989 | Vadgama |
| 4,890,620 A | 1/1990 | Gough |
| 4,890,621 A | 1/1990 | Hakky |
| 4,908,208 A | 3/1990 | Lee et al. |
| 4,909,908 A | 3/1990 | Ross et al. |
| 4,919,141 A | 4/1990 | Zier et al. |
| 4,927,516 A | 5/1990 | Yamaguchi et al. |
| 4,938,860 A | 7/1990 | Wogoman |
| 4,944,299 A | 7/1990 | Silvian |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,970,145 A | 11/1990 | Bennetto et al. |
| 4,973,320 A | 11/1990 | Brenner et al. |
| 4,974,929 A | 12/1990 | Curry |
| 4,988,341 A | 1/1991 | Columbus et al. |
| 4,992,794 A | 2/1991 | Brouwers |
| 4,994,167 A | 2/1991 | Shults et al. |
| 5,002,590 A | 3/1991 | Friesen et al. |
| 5,010,141 A | 4/1991 | Mueller |
| 5,034,112 A | 7/1991 | Murase et al. |
| 5,034,461 A | 7/1991 | Lai et al. |
| 5,045,601 A | 9/1991 | Capelli et al. |
| 5,050,612 A | 9/1991 | Matsumura |
| 5,063,081 A | 11/1991 | Cozzette et al. |
| 5,070,169 A | 12/1991 | Robertson et al. |
| 5,071,452 A | 12/1991 | Avrillon et al. |
| 5,094,876 A | 3/1992 | Goldberg et al. |
| 5,097,834 A | 3/1992 | Skrabal |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint et al. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,200,051 A | 4/1993 | Cozzette et al. |
| 5,202,261 A | 4/1993 | Musho et al. |
| 5,208,147 A | 5/1993 | Kagenow et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,242,835 A | 9/1993 | Jensen |
| 5,249,576 A | 10/1993 | Goldberger et al. |
| 5,250,439 A | 10/1993 | Musho et al. |
| 5,262,305 A | 11/1993 | Heller et al. |
| 5,264,104 A | 11/1993 | Gregg et al. |

(56) References Cited

U.S. PATENT DOCUMENTS

| | | |
|---|---|---|
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,307,263 A | 4/1994 | Brown |
| 5,312,361 A | 5/1994 | Zadini et al. |
| 5,316,008 A | 5/1994 | Suga et al. |
| 5,322,063 A | 6/1994 | Allen et al. |
| 5,324,322 A | 6/1994 | Grill et al. |
| 5,331,555 A | 7/1994 | Hashimoto et al. |
| 5,334,681 A | 8/1994 | Mueller et al. |
| 5,337,747 A | 8/1994 | Neftel |
| 5,342,693 A | 8/1994 | Winters et al. |
| 5,352,348 A | 10/1994 | Young et al. |
| 5,352,351 A | 10/1994 | White |
| 5,354,449 A | 10/1994 | Band et al. |
| 5,372,133 A | 12/1994 | Hogen Esch |
| 5,376,070 A | 12/1994 | Purvis et al. |
| 5,376,400 A | 12/1994 | Goldberg et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,397,451 A | 3/1995 | Senda et al. |
| 5,411,647 A | 5/1995 | Johnson et al. |
| 5,411,866 A | 5/1995 | Luong |
| 5,426,158 A | 6/1995 | Mueller et al. |
| 5,428,123 A | 6/1995 | Ward et al. |
| 5,429,735 A | 7/1995 | Johnson et al. |
| 5,438,984 A | 8/1995 | Schoendorfer |
| 5,462,051 A | 10/1995 | Oka et al. |
| 5,466,356 A | 11/1995 | Schneider et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,482,008 A | 1/1996 | Stafford et al. |
| 5,482,473 A | 1/1996 | Lord et al. |
| 5,494,562 A | 2/1996 | Maley et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,521,273 A | 5/1996 | Yilgor et al. |
| 5,531,679 A | 7/1996 | Schulman et al. |
| 5,531,878 A | 7/1996 | Vadgama et al. |
| 5,541,305 A | 7/1996 | Yokota et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,575,930 A | 11/1996 | Tietje-Girault et al. |
| 5,582,184 A | 12/1996 | Erickson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,589,563 A | 12/1996 | Ward et al. |
| 5,593,852 A | 1/1997 | Heller et al. |
| 5,611,900 A | 3/1997 | Worden |
| 5,624,537 A | 4/1997 | Turner et al. |
| 5,640,954 A | 6/1997 | Pfeiffer |
| 5,660,163 A | 8/1997 | Schulman et al. |
| 5,665,222 A | 9/1997 | Heller et al. |
| 5,670,097 A | 9/1997 | Duan et al. |
| 5,676,820 A | 10/1997 | Wang et al. |
| 5,682,884 A | 11/1997 | Hill |
| 5,695,623 A | 12/1997 | Michel et al. |
| 5,700,559 A | 12/1997 | Sheu et al. |
| 5,703,359 A | 12/1997 | Wampler, III |
| 5,711,861 A | 1/1998 | Ward et al. |
| 5,741,330 A | 4/1998 | Brauker et al. |
| 5,743,262 A | 4/1998 | Lepper, Jr. et al. |
| 5,746,898 A | 5/1998 | Preidel |
| 5,749,832 A | 5/1998 | Vadgama et al. |
| 5,756,632 A | 5/1998 | Ward et al. |
| 5,760,155 A | 6/1998 | Mowrer et al. |
| 5,766,839 A | 6/1998 | Johnson et al. |
| 5,776,324 A | 7/1998 | Usala |
| 5,777,060 A | 7/1998 | Van Antwerp |
| 5,781,455 A | 7/1998 | Hyodo et al. |
| 5,786,439 A | 7/1998 | Van Antwerp et al. |
| 5,791,344 A | 8/1998 | Schulman et al. |
| 5,795,453 A | 8/1998 | Gilmartin |
| 5,800,420 A | 9/1998 | Gross |
| 5,804,048 A | 9/1998 | Wong et al. |
| 5,807,375 A | 9/1998 | Gross et al. |
| 5,807,636 A | 9/1998 | Sheu et al. |
| 5,814,599 A | 9/1998 | Mitragotri et al. |
| 5,820,570 A | 10/1998 | Erickson |
| 5,820,622 A | 10/1998 | Gross et al. |
| 5,822,715 A | 10/1998 | Worthington et al. |
| 5,834,583 A | 11/1998 | Hancock et al. |
| 5,837,377 A | 11/1998 | Sheu et al. |
| 5,837,454 A | 11/1998 | Cozzette et al. |
| 5,837,661 A | 11/1998 | Evans et al. |
| 5,840,148 A | 11/1998 | Campbell et al. |
| 5,843,069 A | 12/1998 | Butler et al. |
| 5,863,972 A | 1/1999 | Beckelmann et al. |
| 5,882,494 A | 3/1999 | Van Antwerp |
| 5,885,566 A | 3/1999 | Goldberg |
| 5,895,235 A | 4/1999 | Droz |
| 5,897,955 A | 4/1999 | Drumheller |
| 5,914,026 A | 6/1999 | Blubaugh, Jr. et al. |
| 5,914,182 A | 6/1999 | Drumheller |
| 5,931,814 A | 8/1999 | Alex et al. |
| 5,932,299 A | 8/1999 | Katoot |
| 5,933,136 A | 8/1999 | Brown |
| 5,945,498 A | 8/1999 | Hopken et al. |
| 5,947,127 A | 9/1999 | Tsugaya et al. |
| 5,954,643 A | 9/1999 | Van Antwerp et al. |
| 5,954,954 A | 9/1999 | Houck et al. |
| 5,955,066 A | 9/1999 | Sako et al. |
| 5,957,854 A | 9/1999 | Besson et al. |
| 5,959,191 A | 9/1999 | Lewis et al. |
| 5,961,451 A | 10/1999 | Reber et al. |
| 5,963,132 A | 10/1999 | Yoakum |
| 5,964,993 A | 10/1999 | Blubaugh et al. |
| 5,965,380 A | 10/1999 | Heller et al. |
| 5,969,076 A | 10/1999 | Lai et al. |
| 5,972,199 A | 10/1999 | Heller |
| 5,977,241 A | 11/1999 | Koloski et al. |
| 5,985,129 A | 11/1999 | Gough et al. |
| 6,001,067 A | 12/1999 | Shults et al. |
| 6,002,954 A | 12/1999 | Van Antwerp et al. |
| 6,007,845 A | 12/1999 | Domb |
| 6,011,984 A | 1/2000 | Van Antwerp et al. |
| 6,018,013 A | 1/2000 | Yoshida et al. |
| 6,018,033 A | 1/2000 | Chen et al. |
| 6,022,463 A | 2/2000 | Leader et al. |
| 6,036,924 A | 3/2000 | Simons et al. |
| 6,039,913 A | 3/2000 | Hirt et al. |
| 6,043,328 A | 3/2000 | Domschke et al. |
| 6,051,389 A | 4/2000 | Ahl et al. |
| 6,059,946 A | 5/2000 | Yukawa et al. |
| 6,066,448 A | 5/2000 | Wohlstadter et al. |
| 6,071,406 A | 6/2000 | Tsou |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,117,290 A | 9/2000 | Say |
| 6,119,028 A | 9/2000 | Schulman et al. |
| 6,121,009 A | 9/2000 | Heller et al. |
| 6,122,536 A | 9/2000 | Sun et al. |

(56) References Cited

U.S. PATENT DOCUMENTS

| | | |
|---|---|---|
| 6,134,461 A | 10/2000 | Say et al. |
| 6,030,827 A | 11/2000 | Davis et al. |
| 6,162,611 A | 12/2000 | Heller et al. |
| 6,169,155 B1 | 1/2001 | Alvarez et al. |
| 6,175,752 B1 | 1/2001 | Say et al. |
| 6,200,772 B1 | 3/2001 | Vadgama et al. |
| 6,212,416 B1 | 4/2001 | Ward et al. |
| 6,233,471 B1 | 5/2001 | Berner et al. |
| 6,248,067 B1 | 6/2001 | Causey, III et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,271,332 B1 | 8/2001 | Lohmann et al. |
| 6,275,717 B1 | 8/2001 | Gross et al. |
| 6,284,478 B1 | 9/2001 | Heller et al. |
| 6,303,670 B1 | 10/2001 | Fujino et al. |
| 6,306,594 B1 | 10/2001 | Cozzette |
| 6,312,706 B1 | 11/2001 | Lai et al. |
| 6,329,161 B1 | 12/2001 | Heller et al. |
| 6,329,488 B1 | 12/2001 | Terry et al. |
| 6,343,225 B1 | 1/2002 | Clark, Jr. |
| 6,358,557 B1 | 3/2002 | Wang et al. |
| 6,368,658 B1 | 4/2002 | Schwarz et al. |
| 6,387,379 B1 | 5/2002 | Goldberg et al. |
| 6,406,066 B1 | 6/2002 | Uegane |
| 6,407,195 B2 | 6/2002 | Sherman et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,461,496 B1 | 10/2002 | Feldman et al. |
| 6,464,849 B1 | 10/2002 | Say et al. |
| 6,466,810 B1 | 10/2002 | Ward et al. |
| 6,484,046 B1 | 11/2002 | Say et al. |
| 6,510,329 B2 | 1/2003 | Heckel |
| 6,512,939 B1 | 1/2003 | Colvin et al. |
| 6,514,718 B2 | 2/2003 | Heller et al. |
| 6,528,584 B2 | 3/2003 | Kennedy et al. |
| 6,534,711 B1 | 3/2003 | Pollack |
| 6,544,212 B2 | 4/2003 | Galley et al. |
| 6,551,496 B1 | 4/2003 | Moles et al. |
| 6,553,241 B2 | 4/2003 | Mannheimer et al. |
| 6,554,982 B1 | 4/2003 | Shin et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,565,509 B1 | 5/2003 | Say et al. |
| 6,579,498 B1 | 6/2003 | Eglise |
| 6,591,125 B1 | 7/2003 | Buse et al. |
| 6,596,294 B2 | 7/2003 | Lai et al. |
| 6,605,072 B2 | 8/2003 | Struys et al. |
| 6,612,984 B1 | 9/2003 | Kerr |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,642,015 B2 | 11/2003 | Vachon et al. |
| 6,654,625 B1 | 11/2003 | Say et al. |
| 6,670,115 B1 | 12/2003 | Zhang |
| 6,689,265 B2 | 2/2004 | Heller et al. |
| 6,692,528 B2 | 2/2004 | Ward et al. |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,741,877 B1 | 5/2004 | Shults et al. |
| 6,742,635 B2 | 6/2004 | Neel et al. |
| 6,773,565 B2 | 8/2004 | Kunimoto et al. |
| 6,784,274 B2 | 8/2004 | van Antwerp et al. |
| 6,789,634 B1 | 9/2004 | Denton |
| 6,793,789 B2 | 9/2004 | Choi et al. |
| 6,801,041 B2 | 10/2004 | Karinka et al. |
| 6,802,957 B2 | 10/2004 | Jung et al. |
| 6,809,653 B1 | 10/2004 | Mann et al. |
| 6,858,218 B2 | 2/2005 | Lai et al. |
| 6,862,465 B2 | 3/2005 | Shults et al. |
| 6,867,262 B1 | 3/2005 | Angel et al. |
| 6,881,551 B2 | 4/2005 | Heller et al. |
| 6,895,263 B2 | 5/2005 | Shin et al. |
| 6,895,265 B2 | 5/2005 | Silver |
| 6,908,681 B2 | 6/2005 | Terry et al. |
| 6,932,894 B2 | 8/2005 | Mao et al. |
| 6,965,791 B1 | 11/2005 | Hitchcock et al. |
| 6,969,451 B2 | 11/2005 | Shin et al. |
| 6,973,706 B2 | 12/2005 | Say et al. |
| 6,998,247 B2 | 2/2006 | Monfre et al. |
| 7,008,979 B2 | 3/2006 | Schottman et al. |
| 7,014,948 B2 | 3/2006 | Lee et al. |
| 7,025,743 B2 | 4/2006 | Mann et al. |
| 7,033,322 B2 | 4/2006 | Silver |
| 7,052,131 B2 | 5/2006 | McCabe et al. |
| 7,058,437 B2 | 6/2006 | Buse et al. |
| 7,060,059 B2 | 6/2006 | Keith et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,118,667 B2 | 10/2006 | Lee |
| 7,120,483 B2 | 10/2006 | Russell et al. |
| 7,136,689 B2 | 11/2006 | Shults et al. |
| 7,153,265 B2 | 12/2006 | Vachon |
| 7,157,528 B2 | 1/2007 | Ward |
| 7,172,075 B1 | 2/2007 | Ji |
| 7,192,450 B2 | 3/2007 | Brauker et al. |
| 7,225,535 B2 | 6/2007 | Feldman et al. |
| 7,226,978 B2 | 6/2007 | Tapsak et al. |
| 7,229,471 B2 | 6/2007 | Gale et al. |
| 7,241,586 B2 | 7/2007 | Gulati |
| 7,248,906 B2 | 7/2007 | Dirac et al. |
| 7,267,665 B2 | 9/2007 | Steil et al. |
| 7,279,174 B2 | 10/2007 | Pacetti et al. |
| 7,335,286 B2 | 2/2008 | Abel et al. |
| 7,336,984 B2 | 2/2008 | Gough et al. |
| 7,357,793 B2 | 4/2008 | Pacetti |
| 7,366,556 B2 | 4/2008 | Brister et al. |
| 7,379,765 B2 | 5/2008 | Petisce et al. |
| 7,417,164 B2 | 8/2008 | Suri |
| 7,423,074 B2 | 9/2008 | Lai et al. |
| 7,470,488 B2 | 12/2008 | Lee et al. |
| 7,519,408 B2 | 4/2009 | Rasdal et al. |
| 7,591,801 B2 | 9/2009 | Brauker et al. |
| 7,640,048 B2 | 12/2009 | Dobbles et al. |
| 7,651,596 B2 | 1/2010 | Petisce et al. |
| 7,657,297 B2 | 2/2010 | Simpson et al. |
| 8,364,229 B2 | 1/2013 | Simpson et al. |
| 10,028,683 B2 * | 7/2018 | Simpson ............ A61B 5/14532 |
| 2001/0016682 A1 | 8/2001 | Berner et al. |
| 2001/0041830 A1 | 11/2001 | Varalli et al. |
| 2001/0056232 A1 | 12/2001 | Lardo et al. |
| 2002/0018843 A1 | 2/2002 | Van Antwerp et al. |
| 2002/0042561 A1 | 4/2002 | Schulman et al. |
| 2002/0043471 A1 | 4/2002 | Shin et al. |
| 2002/0055673 A1 | 5/2002 | Van Antwerp et al. |
| 2002/0084196 A1 | 7/2002 | Liamos et al. |
| 2002/0099997 A1 | 7/2002 | Pi ret |
| 2002/0119711 A1 | 8/2002 | Van Antwerp et al. |
| 2002/0123087 A1 | 9/2002 | Vachon et al. |
| 2002/0128546 A1 | 9/2002 | Silver |
| 2002/0161288 A1 | 10/2002 | Shin et al. |
| 2002/0185384 A1 | 12/2002 | Leong et al. |
| 2002/0188185 A1 | 12/2002 | Sohrab |
| 2003/0009093 A1 | 1/2003 | Silver |
| 2003/0023317 A1 | 1/2003 | Brauker et al. |
| 2003/0032874 A1 | 2/2003 | Rhodes et al. |
| 2003/0059631 A1 | 3/2003 | Al-Lamee |
| 2003/0065254 A1 | 4/2003 | Schulman et al. |
| 2003/0069383 A1 | 4/2003 | Van Antwerp et al. |
| 2003/0088166 A1 | 5/2003 | Say et al. |
| 2003/0096424 A1 | 5/2003 | Mao et al. |
| 2003/0097082 A1 | 5/2003 | Purdy et al. |
| 2003/0104273 A1 | 6/2003 | Lee et al. |
| 2003/0125498 A1 | 7/2003 | McCabe et al. |
| 2003/0130616 A1 | 7/2003 | Steil et al. |
| 2003/0132227 A1 | 7/2003 | Geisler |
| 2003/0134100 A1 | 7/2003 | Mao et al. |

(56) References Cited

U.S. PATENT DOCUMENTS

| | | |
|---|---|---|
| 2003/0134347 A1 | 7/2003 | Heller et al. |
| 2003/0157409 A1 | 8/2003 | Huang et al. |
| 2003/0181794 A1 | 9/2003 | Rini et al. |
| 2003/0187338 A1 | 10/2003 | Say et al. |
| 2003/0188427 A1 | 10/2003 | Say et al. |
| 2003/0199745 A1 | 10/2003 | Burson et al. |
| 2003/0199878 A1 | 10/2003 | Pohjonen et al. |
| 2003/0203991 A1 | 10/2003 | Schottman et al. |
| 2003/0211050 A1 | 11/2003 | Majeti et al. |
| 2003/0211625 A1 | 11/2003 | Cohan |
| 2003/0212346 A1 | 11/2003 | Yuzhakov et al. |
| 2003/0212347 A1 | 11/2003 | Sohrab |
| 2003/0217966 A1 | 11/2003 | Tapsak et al. |
| 2003/0225324 A1 | 12/2003 | Anderson et al. |
| 2003/0228681 A1 | 12/2003 | Ritts et al. |
| 2003/0235817 A1 | 12/2003 | Bartkowiak et al. |
| 2004/0006263 A1 | 1/2004 | Anderson et al. |
| 2004/0011671 A1 | 1/2004 | Shults et al. |
| 2004/0045879 A1 | 3/2004 | Shults et al. |
| 2004/0063167 A1 | 4/2004 | Kaastrup et al. |
| 2004/0074785 A1 | 4/2004 | Holker |
| 2004/0078219 A1 | 4/2004 | Kaylor |
| 2004/0084306 A1 | 5/2004 | Shin et al. |
| 2004/0106741 A1 | 6/2004 | Kriesel et al. |
| 2004/0106857 A1 | 6/2004 | Gough |
| 2004/0111017 A1 | 6/2004 | Say et al. |
| 2004/0111144 A1 | 6/2004 | Lawin et al. |
| 2004/0120848 A1 | 6/2004 | Teodorczyk |
| 2004/0138543 A1 | 7/2004 | Russell et al. |
| 2004/0143173 A1 | 7/2004 | Reghabi et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0213985 A1 | 10/2004 | Lee et al. |
| 2004/0224001 A1 | 11/2004 | Pacetti et al. |
| 2004/0228902 A1 | 11/2004 | Benz |
| 2004/0234575 A1 | 11/2004 | Horres et al. |
| 2005/0013842 A1 | 1/2005 | Qiu et al. |
| 2005/0027180 A1 | 2/2005 | Goode et al. |
| 2005/0027182 A1 | 2/2005 | Siddiqui et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051440 A1 | 3/2005 | Simpson et al. |
| 2005/0056552 A1 | 3/2005 | Petisce et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |
| 2005/0044088 A1 | 5/2005 | Agus |
| 2005/0107677 A1 | 5/2005 | Ward et al. |
| 2005/0112169 A1 | 5/2005 | Brauker et al. |
| 2005/0112172 A1 | 5/2005 | Pacetti |
| 2005/0112358 A1 | 5/2005 | Potyrailo et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say |
| 2005/0124873 A1 | 6/2005 | Shults et al. |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0182451 A1 | 8/2005 | Griffin et al. |
| 2005/0184641 A1 | 8/2005 | Armitage et al. |
| 2005/0192557 A1 | 9/2005 | Brauker et al. |
| 2005/0196747 A1 | 9/2005 | Stiene |
| 2005/0197554 A1 | 9/2005 | Polcha |
| 2005/0203360 A1 | 9/2005 | Brauker et al. |
| 2005/0209665 A1 | 9/2005 | Hunter et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0261563 A1 | 11/2005 | Zhou et al. |
| 2005/0271546 A1 | 12/2005 | Gerber et al. |
| 2005/0274665 A1 | 12/2005 | Heilmann et al. |
| 2005/0282997 A1 | 12/2005 | Ward |
| 2006/0003398 A1 | 1/2006 | Heller et al. |
| 2006/0007391 A1 | 1/2006 | McCabe et al. |
| 2006/0008370 A1 | 1/2006 | Massaro et al. |
| 2006/0015020 A1 | 1/2006 | Neale et al. |
| 2006/0015024 A1 | 1/2006 | Brister et al. |
| 2006/0019327 A1 | 1/2006 | Brister et al. |
| 2006/0020186 A1 | 1/2006 | Brister et al. |
| 2006/0036140 A1 | 2/2006 | Brister et al. |
| 2006/0036141 A1 | 2/2006 | Kamath et al. |
| 2006/0036143 A1 | 2/2006 | Brister et al. |
| 2006/0036144 A1 | 2/2006 | Brister et al. |
| 2006/0047095 A1 | 3/2006 | Pacetti |
| 2006/0058868 A1 | 3/2006 | Gale et al. |
| 2006/0065527 A1 | 3/2006 | Samproni |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0086624 A1 | 4/2006 | Tapsak et al. |
| 2006/0134165 A1 | 6/2006 | Pacetti |
| 2006/0142523 A1 | 6/2006 | Lai et al. |
| 2006/0142525 A1 | 6/2006 | Lai et al. |
| 2006/0142526 A1 | 6/2006 | Lai et al. |
| 2006/0142651 A1 | 6/2006 | Brister et al. |
| 2006/0148985 A1 | 7/2006 | Karthauser |
| 2006/0155180 A1 | 7/2006 | Brister et al. |
| 2006/0159718 A1 | 7/2006 | Rathenow et al. |
| 2006/0171980 A1 | 8/2006 | Helmus et al. |
| 2006/0177379 A1 | 8/2006 | Asgari |
| 2006/0183178 A1 | 8/2006 | Gulati |
| 2006/0183871 A1 | 8/2006 | Ward et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0229512 A1 | 10/2006 | Petisce et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0257996 A1 | 11/2006 | Simpson et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0003588 A1 | 1/2007 | Chinn et al. |
| 2007/0007133 A1 | 1/2007 | Mang et al. |
| 2007/0027385 A1 | 2/2007 | Brister et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0042377 A1* | 2/2007 | Gao ............. B01D 69/141 435/6.11 |
| 2007/0045902 A1 | 3/2007 | Brauker et al. |
| 2007/0059196 A1 | 3/2007 | Brister et al. |

(56) References Cited

U.S. PATENT DOCUMENTS

| | | |
|---|---|---|
| 2007/0088208 A1 | 4/2007 | Yasuzawa et al. |
| 2007/0123963 A1 | 5/2007 | Krulevitch |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0155851 A1 | 7/2007 | Alli et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0200267 A1 | 8/2007 | Tsai |
| 2007/0202562 A1 | 8/2007 | Curry |
| 2007/0203410 A1 | 8/2007 | Say et al. |
| 2007/0203448 A1 | 8/2007 | Melker et al. |
| 2007/0203568 A1 | 8/2007 | Gale et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0233013 A1 | 10/2007 | Schoenberg |
| 2007/0235331 A1 | 10/2007 | Simpson et al. |
| 2007/0242215 A1 | 10/2007 | Schorzman et al. |
| 2007/0244379 A1 | 10/2007 | Boock et al. |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0001318 A1 | 1/2008 | Schorzman et al. |
| 2008/0021008 A1 | 1/2008 | Pacetti et al. |
| 2008/0027301 A1 | 1/2008 | Ward et al. |
| 2008/0031918 A1 | 2/2008 | Lawin et al. |
| 2008/0033269 A1 | 2/2008 | Zhang |
| 2008/0034972 A1 | 2/2008 | Gough et al. |
| 2008/0038307 A1 | 2/2008 | Hoffmann |
| 2008/0045824 A1 | 2/2008 | Tapsak et al. |
| 2008/0071027 A1 | 3/2008 | Pacetti |
| 2008/0076897 A1 | 3/2008 | Kunzler et al. |
| 2008/0081184 A1 | 4/2008 | Kubo et al. |
| 2008/0113207 A1 | 5/2008 | Pacetti et al. |
| 2008/0138497 A1 | 6/2008 | Pacetti et al. |
| 2008/0138498 A1 | 6/2008 | Pacetti et al. |
| 2008/0143014 A1 | 6/2008 | Tang |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0200788 A1 | 8/2008 | Brister et al. |
| 2008/0208025 A1 | 8/2008 | Shults et al. |
| 2008/0210557 A1 | 9/2008 | Heller et al. |
| 2008/0213460 A1 | 9/2008 | Benter et al. |
| 2008/0214915 A1 | 9/2008 | Brister et al. |
| 2008/0262469 A1 | 10/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294026 A1 | 11/2008 | Arbault et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312397 A1 | 12/2008 | Lai et al. |
| 2009/0004243 A1 | 1/2009 | Pacetti et al. |
| 2009/0012205 A1 | 1/2009 | Nakada et al. |
| 2009/0018418 A1 | 1/2009 | Markle et al. |
| 2009/0018426 A1 | 1/2009 | Markle et al. |
| 2009/0030294 A1 | 1/2009 | Petisce et al. |
| 2009/0045055 A1 | 2/2009 | Rhodes et al. |
| 2009/0061528 A1 | 3/2009 | Suri |
| 2009/0076356 A1 | 3/2009 | Simpson |
| 2009/0076360 A1 | 3/2009 | Brister et al. |
| 2009/0081803 A1 | 3/2009 | Gamsey et al. |
| 2009/0156924 A1 | 6/2009 | Shariati et al. |
| 2009/0177143 A1 | 7/2009 | Markle et al. |
| 2009/0192366 A1 | 7/2009 | Mensinger et al. |
| 2009/0192722 A1 | 7/2009 | Shariati et al. |
| 2009/0192751 A1 | 7/2009 | Kamath et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0247855 A1 | 10/2009 | Boock et al. |
| 2009/0247856 A1 | 10/2009 | Boock et al. |
| 2009/0264719 A1 | 10/2009 | Markle et al. |
| 2009/0287073 A1 | 11/2009 | Boock et al. |
| 2009/0299276 A1 | 12/2009 | Brauker et al. |
| 2010/0041971 A1 | 2/2010 | Goode, Jr. et al. |
| 2010/0049024 A1 | 2/2010 | Saint et al. |
| 2010/0076283 A1 | 3/2010 | Simpson et al. |
| 2012/0088993 A1 | 4/2012 | Buck et al. |
| 2013/0261417 A1 | 10/2013 | Simpson et al. |

FOREIGN PATENT DOCUMENTS

| | | |
|---|---|---|
| EP | 0 286 118 | 10/1988 |
| EP | 0 291 130 | 11/1988 |
| EP | 0 313 951 | 5/1989 |
| EP | 0 320 109 | 6/1989 |
| EP | 0 353 328 | 2/1990 |
| EP | 0 362 145 | 4/1990 |
| EP | 0 390 390 | 10/1990 |
| EP | 0 396 788 | 11/1990 |
| EP | 0 535 898 | 4/1993 |
| EP | 0 563 795 | 10/1993 |
| EP | 0 817 809 | 1/1998 |
| EP | 0 862 648 | 9/1998 |
| EP | 0 880 936 | 12/1998 |
| EP | 0 967 788 | 12/1999 |
| FR | 2656423 | 6/1991 |
| FR | 2760962 | 9/1998 |
| GB | 2149918 | 6/1985 |
| GB | 2209836 | 5/1989 |
| JP | 57156004 | 9/1982 |
| JP | 57156005 | 9/1982 |
| JP | 58163403 | 9/1982 |
| JP | 58163402 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59-211459 | 11/1984 |
| JP | 59209608 | 11/1984 |
| JP | 59209609 | 11/1984 |
| JP | 59209610 | 11/1984 |
| JP | 60245623 | 12/1985 |
| JP | 61238319 | 10/1986 |
| JP | 62074406 | 4/1987 |
| JP | 62083649 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 07-083871 | 3/1995 |
| JP | 8196626 | 8/1996 |
| JP | 2002-189015 | 7/2002 |
| WO | WO 1989-002720 | 4/1989 |
| WO | WO 1990-007575 | 7/1990 |
| WO | WO 1990-010861 | 9/1990 |
| WO | WO 1992-013271 | 8/1992 |
| WO | WO 1993-014185 | 7/1993 |
| WO | WO 1993-014693 | 8/1993 |
| WO | WO 1993-023744 | 11/1993 |
| WO | WO 1994-008236 | 4/1994 |

(56) References Cited

FOREIGN PATENT DOCUMENTS

| WO | WO 1996-014026 | 5/1996 |
|---|---|---|
| WO | WO 1996-025089 | 8/1996 |
| WO | WO 1996-030431 | 10/1996 |
| WO | WO 1997-001986 | 1/1997 |
| WO | WO 1997-006727 | 2/1997 |
| WO | WO 1997-011067 | 3/1997 |
| WO | WO 1997-028737 | 8/1997 |
| WO | WO 1998-003431 | 1/1998 |
| WO | WO 1998-024358 | 6/1998 |
| WO | WO 1999-056613 | 4/1999 |
| WO | WO 2000-019887 | 4/2000 |
| WO | WO 2000-032098 | 6/2000 |
| WO | WO 2000-033065 | 6/2000 |
| WO | WO 2000-059373 | 10/2000 |
| WO | WO 2000-074753 | 12/2000 |
| WO | WO 2001-021827 | 3/2001 |
| WO | WO 2002-053764 | 7/2002 |
| WO | WO 2005-045394 | 5/2005 |
| WO | WO 2005-057175 | 6/2005 |
| WO | WO 2005-026689 | 10/2005 |
| WO | WO 2006-018425 | 2/2006 |
| WO | WO 2007-114943 | 10/2007 |
| WO | WO 2007-147475 | 12/2007 |

OTHER PUBLICATIONS

Aalders et al. 1991, Development of a wearable glucose sensor; studies in healthy volunteers and in diabetic patients. Intl J Artificial Organs 14(2):102-108.
Abe et al, 1992. Characterization of glucose microsensors for intracellular measurements, Analytical Chemistry 64(18):2160-2163
Abel et al. 1984. Experience with an implantable glucose sensor as a prerequisite of an artificial beta cell. Biomedica Biochimica Acta 43(5):577-584.
Abel et al. 2002. Biosensors for in vivo glucose measurement: can we cross the experimental stage. Biosensors & Bioelectronics 17:1059-1070.
Alcock & Turner 1994. Continuous Analyte Monitoring to Aid Clinical Practice. IEEE Engineering in Med & Biol 13:319-325.
American Heritage Dictionary 4th Edition, 2000. Houghton Mifflin Company p. 82.
Amin et al. 2003. Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Miffling Company 2002. Answers.com Nov. 7, 2006 http:--www. Answers.com-topic-xenogenic.
Armour et al. Dec. 1990. Application of Chronic Intravascular Blood Glucose Sensor in Dogs. Diabetes 39:1519-1526.
Assolant-Vinet et al. 1986. New Immobilized Enzyme Membranes for Tailor-Made Biosensors. Analytical Letters 19(7&8): 875-885.
Atanasov et al. 1994, Biosensor for continuous glucose monitoring. Biotechnology & Bioengineering 43:262-266.
Atanasov et al. 1997. Implantation of a refillable glucose monitoring-telemetry device. Biosensors & Bioelectronics 12:669-680.
Aussedat et al. 1997. A user-friendly method for calibrating a subcutaneous glucose sensor-based hypoglycaemic alarm. Biosensors & Bioelectronics 12(11): 1061-1071.
Bailey et al. 2007, Reduction in hemoglobin A1c with real-time continuous glucose monitoring: results from a 12-week observational study. Diabetes Technology & Therapeutics 9(3):203-210.
Baker, 2008. Vapor and Gas Separation by Membranes. Chapter 21, pp. 559-580 in Advanced Membrane Technology and Applications, Eds. Li et al., John Wiley & Sons Inc., Hoboken, New Jersey.
Bard et al. 1980. Electrochemical Methods. John Wiley & Sons pp. 173-175.
Beach et al. 1999. Subminiature implantable potentiostat and modified commercial telemetry device for remote glucose monitoring. IEEE Trans Instrumentation & Measurement 48(6):1239-1245.
Bellueci et al. Jan. 1986. Electrochemical behaviour of graphite-epoxy composite materials (GECM) in aqueous salt solutions J. Applied Electrochemistry 16(1):15-22.
Bessman et al., 1973. Progress toward a glucose sensor for the artificial pancreas. Proceedings of a Workshop on Ion-Selective Microelectrodes Jun. 4-5, 1973 Boston MA 189-197.
Biermann et al. 2008. How would patients behave if they were continually informed of their blood glucose levels? A simulation study using a "virtual" patient. Diabetes Technology & Therapeutics 10:178-187.
Bindra et al. 1991. Design and In Vitro Studies of a Needle-Type Glucose Sensor for Subcutaneous Monitoring. Analytical Chemistry 63:1692-1696.
Bisenberger et al. 1995. A triple-step potential waveform at enzyme multisensors with thick-film gold electrodes for detection of glucose and sucrose. Sensors and Actuators B 28: 181-189.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats. J Biomedical Engineering 15:457-463.
Bode B. W. 2000. Clinical utility of the continuous glucose monitoring system. Diabetes Technology & Therapeutics 2(Suppl 1):S35-S41.
Bode et al. 1999. Continuous glucose monitoring used to adjust diabetes therapy improves glycosylated hemoglobin: A pilot study. Diabetes Research & Clinical Practice 46:183-190.
Bode et al. 2000. Using the continuous glucose monitoring system to improve the management of type 1 diabetes. Diabetes Technology & Therapeutics 2(Suppl 1):S43-S48.
Boedeker Plastics Inc. 2009. Polyethylene Specifications Data Sheet http:--www.boedeker.com-polyc_p.htm [Aug. 19, 2009 3:36:33 PM].
Boland et al. 2001. Limitations of conventional methods of self-monitoring of blood glucose. Diabetes Care 24(11):1858-1862.
Bowman L.; Meindl J. D. 1986. The packaging of implantable integrated sensors. IEEE Trans Biomed Eng (BME) 33(2):248-255.
Brauker et al. Jun. 27, 1996. Local Inflammatory Response Around Diffusion Chambers Containing Xenografts. Transplantation 61 (12):1671-1677.
Braunwald 2008. Biomarkers in heart failure. NEJM 358: 2148-2159.
Bremer et al. 2001. Benchmark data from the literature for evaluation of new glucose sensing technologies. Diabetes Technology & Therapeutics 3(3):409-418.
Brooks et al. 1987-88. Development of an on-line glucose sensors for fermentation monitoring. Biosensors 3:45-56.
Bruckel et al. 1989. In vivo measurement of subcutaneous glucose concentrations with an enzymatic glucose sensor and a wick method. Klin Wochenschr 67:491-495.
Cai et al. 2004. A wireless remote query glucose biosensor based on a pH-sensitive polymer, Analytical Chemistry 76(4):4038-4043.
Campanella et al. 1993. Biosensor for direct determination of glucose and lactate in undiluted biological fluids. Biosensors & Bioelectronics 8:307-314.
Candas et al. 1994. An adaptive plasma glucose controller based on a nonlinear insulin-glucose model. IEEE Trans Biomed Eng (BME) 41(2): 116-124.
Cass et al. 1984. Ferrocene-mediated enzyme electrodes for amperometric determination of glucose. Analytical Chemistry 36:667-671.
Cassidy et al. Apr. 1993. Novel electrochemical device for the detection of cholesterol or glucose. Analyst 118:415-418.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high H2S-CH4 selectivity. J Membrane Science 135:99-106.
Chia et al. 2004. Glucose sensors toward closed loop insulin delivery. Endocrinol Metab Clin North Am 33:175-195.
Ciba® Irgacure® 2959 Photoinitiator Product Description. Apr. 2, 1998. Ciba Specialty Chemicals Inc. Basel Switzerland (3 pages).

(56) References Cited

OTHER PUBLICATIONS

Claremont et al. 1986. Subcutaneous implantation of a ferrocene-mediated glucose sensor in pigs. Diabetologia 29:817-821.
Claremont et al. Jul. 1986. Potentially-implantable ferrocene-mediated glucose sensor. J Biomedical Engineering 8:272-274.
Clark et al. 1981. One-minute electrochemical enzymic assay for cholesterol in biological materials. Clinical Chemistry 27(12):1978-1982.
Clark et al. 1987. Configurational cyclic voltammetry: increasing the specificity and reliability of implanted electrodes. IEEE—Ninth Annual Conference of the Engineering in Medicine and Biology Society pp. 0782-0783.
Clark et al. 1988. Long-term stability of electroenzymatic glucose sensors implanted in mice. Trans American Society of Artificial Internal Organs 34:259-265.
CLSI, 2008, Performance metrics for continuous interstitial glucose monitoring; approved guideline CLSI document POCT05-A. Wayne PA. Clinical and Laboratory Standards Institute: 2008 28(33) 72 pp.
Colangelo et al. 1967. Corrosion rate measurements in vivo. J Biomedical Matls Research 1:405-414.
Colowick et al. 1976. Methods in Enzymology vol. XLIV Immobilized Enzymes. New York: Academic Press.
Cox et al. 1985. Accuracy of perceiving blood glucose in IDDM. Diabetes Care 8(6):529-536.
Csoregi et al. 1994. Design characterization and one-point in vivo calibration of a subcutaneously implanted glucose electrode. Analytical Chemistry 66(19):3131-3138.
Danielsson et al. 1988. Enzyme thermistors. Methods in Enzymology 137:181-197.
Dassau et al. 2009. In silica evaluation platform for artificial pancreatic β-cell development—a dynamic simulator for closed loop control with hardware-in-the-loop. Diabetes Technology & Therapeutics 11(3):1-8.
Davies et al. 1992: Polymer membranes in clinical sensor applications. I. An overview of membrane function. Biomaterials 13(14):971-978.
Davis et al. 1983. Bioelectrochemical fuel cell and sensor based on a quinoprotein alcohol dehydrogenase. Enzyme Microb Technol 5:383-388.
Decher et al. 1992. Buildup of ultrathin multilayer films by a self-assembly process: III. Consecutively alternating adsorption of anionic and cationic polyelectrolytes on charged surfaces. Thin Solid Films 210/211:831-835.
Dixon et al. 2002. Characterization in vitro and in vivo of the oxygen dependence of an enzyme-polymer biosensor for monitoring brain glucose. J. Neuroscience Methods 119:135-142.
DuPont[1] Dimension AR® (Catalog) 1998.
Durliat et al, 1976. Spectrophotometric and electrochemical determination of L(+)-lactate in blood by use of lactate dehydrogenase from yeast. Clinical Chemistry 22(11):1802-1805.
Edwards Lifesciences, 2002. Accuracy for your and your patients. Marketing materials (4 pages).
Ekinci et al. 2006. Preparation and Characterization of an Aromatic Polyimide and Its Use as a Selective Membrane for H2O2. Turk J Chem. 30:277-285.
El Degheidy et al. 1986. Optimization of an implantable coated wire glucose sensor. J Biomedical Engineering 8:121-129.
El-Khatib et al. 2007. Adaptive closed-loop control provides blood-glucose regulation using dual subcutaneous insulin and glucagon infusion in diabetic swine. J Diabetes Science & Technology 1(2):181-192.
El-Sa'ad et al. 1990. Moisture Absorption by Expoxy Resins: The Reverse Thermal Effect. J Matls Science 25:3577-3582.
Ernst et al. 2002. Reliable glucose monitoring through the use of microsystem technology. Analytical & Bioanalytical Chemistry 373:758-761.
Fahy et al. Mar. 2008. An analysis: hyperglycemic intensive care patients need continuous glucose monitoring-easier said than done. J Diabetes Science & Technology 2(2):201-204.

Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type I diabetes. Diabetes Technology & Therapeutics 5(5):769-779.
Fischer et al. 1987. Assessment of subcutaneous glucose concentration: validation of the wick technique as a reference for implanted electrochemical sensors in normal and diabetic dogs. Diabetologia 30:940-945.
Fischer et al. 1989. Oxygen Tension at the Subcutaneous Implantation Site of Glucose Sensors. Biomedica Biochimica Acta 11/12:965-972.
Fischer et al. 1995. Hypoglycaemia-warning by means of subcutaneous electrochemical glucose sensors: an animal study. Hormone Metabolism Research 27:53 [Abstract].
Freedman et al. 1991. Statistics Second Edition W.W. Norton & Company p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diabetes Technology & Therapeutics 10:188-193.
Ganesan et al. 2005. Gold layer-based dual crosslinking procedure of glucose oxidase with ferrocene monocarboxylic acid provides a stable biosensor. Analytical Biochemistry 343:188-191.
Ganesh et al. Mar. 2008. Evaluation of the VIA® blood chemistry monitor for glucose in healthy and diabetic volunteers. J Diabetes Science & Technology 2(2):182-193.
Gao et al. 1989. Determination of Interfacial parameters of cellulose acetate membrane materials by HPLC. J Liquid Chromatography 12(11):2083-2092.
Garg et al. 2004. Improved Glucose Excursions Using an Implantable Real-Time continuous Glucose Sensor in Adults with Type 1 Diabetes. Diabetes Care 27:734-738.
Gerritsen et al. 1999. Performance of subcutaneously implanted glucose sensers for continuous monitoring Netherlands J Medicine 54:167-179.
Gerritsan M. 2000. Problems associated with subcutaneousiy implanted glucose sensors, Diabetes Care 23(2):143-145.
Giliigan et al. 1994. Evaluation of a subcutaneous glucose sensor out to 3 months in a dog model. Diabetes Care 17(8):882-887.
Gilligan et al. 2004. Feasibility of continuous long-term glucose monitoring from a subcutaneous glucose sensor in humans. Diabetes Technology & Therapeutics 6:378-386.
Godsland et al. 2001. Maximizing the Success Rate of Minimal Model Insulin Sensitivity Measurement in Humans: The Importance of Basal Glucose Levels. Clinical Science 101:1-9.
Gouda et al. Jul. 4, 2003. Thermal inactivation of glucose oxidase. J Biological Chemistry 278(27):24324-24333.
Gough et al. 2000. Immobilized glucose oxidase in implantable glucose sensor technology, Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics 2(Suppl 1):S19-S26.
Gross et al. 2000. Performance evaluation of the MiniMed® continuous giucose monitoring system during patient home use. Diabetes Technology & Therapeutics 2(1):49-56.
Guerci et al. 2003. Clinical performance of CGMS in type I diabetic patients treated by continuous subcutaneous insulin infusion using insulin analogs. Diabetes Care 26:582-589.
Guo et al. 1998. Modification of cellulose acetate ultrafiltration membrane by gamma ray radiation. Shuichuli Jishi Bianji Weiyuanhui 23(6):315-318 [Abstract].

(56) References Cited

OTHER PUBLICATIONS

Hall et al. 1998. Electrochemical oxidation of hydrogen peroxide at platinum electrodes. Part I: An adsorption-controlled mechanism. Electrochimica Acta 43(5-6):579-588.

Hall et el. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III, Effect of temperature. Electrochimica Acta 44:2455-2462.

Hall et al. 1999. Electrochemical oxidation of hydrogen peroxide at platinum electrodes. Part IV: Phosphate buffer dependence. Electrochimica Acta 44:4573-4582.

Hall et al. 2000. Electrochemical oxidation of hydrogen peroxide at platinum electrodes. Part V: Inhibition by chloride. Electrochimica Acta 45:3573-3579.

Hamilton Syringe Selection Guide. 2006. Syringe Selection www.hamiltoncompany.com.

Harrison et el. 1988. Characterization of perfluorosulfonic acid polymer coated enzyme electrodes and a miniaturized integrated potentiostat for glucose analysis in whole blood. Analytical Chemistry 60:2002-2007.

Hashiguchi et al. 1994. Development of a miniaturized glucose monitoring by combining a needle-type glucose sensor with microdialysis sampling method: Long-term subcutaneous tissue glucose monitoring in ambulatory diabetic patients. Diabetes Care 17(5):387-396.

Heller 1990. Electrical wiring of redox enzymes, Acc. Chem. Res. 23:128-134.

Heller A. 1992. Electrical Connection of Enzyme Redox Centers to Electrodes. J Physical Chemistry 96:3579-3587.

Heller A. 1999. implanted electrochemical glucose sensors for the management of diabetes. Annual Review of Biomedical Engineering 1:153-175.

Heller A. 2003. Plugging metal connectors into enzymes. Nature Biotechnology 21:631-632.

Hicks 1985. In Situ Monitoring. Clinical Chemistry 31 (12)1931-1935.

Hitchman M. L. 1978. Measurement of Dissolved Oxygen. vol. 49, Chapter 3, pp. 34-49 and 59-123 in Elving et al.(Eds.), Chemical Analysis, John Wiley & Sons, New York, New York.

Hoel Paul G. 1976, Elementary Statistics Fourth Edition, John Wiley & Sons Inc.. pp. 113-114.

Hrapovic et al. 2003. Picoamperometric detection of glucose at ultrasmall platinum-based biosensors: preparation and characterization, Analytical Chemistry 75:3308-3315.

http:--www.merriam-webster.com-dictionary definition for "aberrant" Aug. 19, 2008 p. 1.

Hu et al. 1993. A needle-type enzyme-based lactate sensor for in vivo monitoring. Analytica Chimica Acta 281:503-511.

Huang et al. Aug. 1975. Electrochemical Generation of Oxygen. I: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce-NTIS pp. 1-116.

Huang et al. Sep. 1997, A 0.5mW Passive Telemetry IC for Biomedical Applications. Proceedings of the 23rd European Solid-State Circuits Conference (ESSCIRC '97) pp. 172-175 Southampton UK.

Hunter et al. Mar. 31 2000. Minimally Invasive Glucose Sensor and Insulin Delivery System. MIT Home Automation and Healthcare Consortium. Progress Report No. 2-5, 17 pages.

Ishikawa et al. 1998, Initial evaluation of a 290-mm diameter subcutaneous glucose sensor: Glucose monitoring with a biocompatible flexible-wire enzyme-based amperometric microsensor in diabetic and nondiabetic humans. J Diabetes & Its Complications 12:295-301.

Jaffari et al. 1995. Recent advances in amperometric glucose biosensors for in vivo monitoring. Physiological Meas 16:1-15.

Jensen et al. 1997. Fast wave forms for pulsed electrochemical detection of glucose by incorporation of reductive desorption of oxidation products. Analytical Chemistry 69(9): i776-1781.

Jeutter D. C. 1982. A transcuteneous implanted battery recharging and biotelemeter power switching system. IEEE Trans Biomed Eng (BME) 29:314-321.

Jobst et al. 1996. Thin-Film Microbiosensors for Glucose-Lactate Monitoring. Analytical Chemistry 68(18):3173-3179.

Johnson 1991. Reproducible electrodeposition of biomolecules for the fabrication of miniature electroenzymatic biosensors. Sensors and Actuators B 5:85-89.

Johnson et al. 1992. In vivo evaluation of an electroenzymatic glucose sensor implanted in subcutaneous tissue. Biosensors & Bioelectronics 7:709-714.

Jovanovic L. 2000. The role of continuous glucose monitoring in gestational diabetes mellitus. Diabetes Tochnology & Therapeutics 2(Suppl 1)S67-S71.

Kacaniklic et al. May-Jun. 1994. Amperometric Biosensors for Detection of L- and D-Amino Acids Based on Coimmoblized Peroxidase and L- and D-Amino Acid Oxidases in Carbon Paste Electrodes. Electroanalysis 6(5-6):381-390.

Kamath et al. 2008. Calibration of as continuous glucose monitor: effect of glucose rate of change. Eighth Annual Diabetes Technology Meeting Nov. 13-15, 2008, p. A88 [Abstract].

Kang et al. 2003. In vitro and short-term in vivo characteristics of a Kel-F thin film modified giucose sensor. Analytical Science 19:1481-1486.

Kaufman et al. 2001. A pilot study of the continuous glucose monitoring system. Diabetes Care 24(12):2030-2034.

Kaufman. 2000. Role of the continuous glucose monitoring system in pediatric patients. Diabetes Technology & Therapeutics 2(Suppl. 1):S49-S52.

Kawagoe et al. 1991. Enzyme-modified organic-conducting salt microelectrode. Analytical Chemistry 63:2961-2965.

Keedy et al. 1991. Determination of urate in undiluted whole blood by enzyme electrode. Biosensors & Bioelectronics 6:491-499.

Kerner et al. 1988. A potentially implantable enzyme electrode for amperometric measurement of glucose Horm Metab Res Suppl. 20:8-13.

Kerner et al. 1993. The function of a hydrogen peroxide-detecting electroenzymatic glucose electrode is markedly impaired in human sub-cutaneous tissue and plasma. Biosensors & Bioelectronics 8:473-482.

Klueh et al. 2003. Use of Vascular Endothelia Cell Growth Factor Gene Transfer to Enhance Implantable Sensor Function in Vivo. J Biomed Matls Res 67A:1072-1086.

Kondo et al. 1982. A miniature glucose sensor implantable in the blood stream. Diabetes Care 5(3):218-221.

Koschinsky et al. 1988. New approach to technical and clinical evaluation of devices for self-monitoring of blood glucose. Diabetes Care 11 (8):619-619.

Koschinsky et al. 2001. Sensors for glucose monitoring: Technical and clinical aspects. Diabetes Metabolism Research Review 37:113-123.

Kost et al. 1985. Glucose-sensitive membranes containing glucose oxidase: activity swelling and permeability studies. J Biomed Matls Res 19:1117-1133.

Koudelka et al, 1989. In vivo response of microfabricated glucose sensors to glycemia changes in normal rats. Biomedica Biochimica Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensor & Actuators A 91:266-277.

Kruger et al. 2000. Psychological motivation and patient education: A role for continuous glucose monitoring. Diabetes Technology & Therapeutics 2(Suppl 1):S93-97.

Kulys et al. 1994. Carbon-paste biosensors array for long-term glucose measurement. Biosensors & Bioelectronics 9:491-500.

Kunjan, et al. Mar. 2008. Automated blood sampling and glucose sensing in critical care settings. J. Diabetes Science & Technology 2(3):194-200.

(56) References Cited

OTHER PUBLICATIONS

Kurtz et al. 2005. Recommendations for blood pressure measurement in humans and experimental animals Part 2: Blood pressure measurement in experimental animals: A statement for professionals from the subcommittee of professional and public education of the American Heart Association Council on High Blood Pressure Research. Hypertension 45:299-310.

Ladd et al. 1996. Structure Determination by X-ray Crystallography 3rd ed. Plenum 1996 Ch. 1 pp. xxi-xxiv and 1-58.

Lehmann et al. May 1994. Retrospective validation of a physiological model of glucose-insuiin interaction in type 1 diabetes mellitus. Med. Eng. Phys. 16:193-202.

Lerner et al. 1984. An implantable electrochemical glucose sensor. Ann NY Acad Sci 428:263-278.

Lewandowski et al. 1988. Evaluation of a miniature blood glucose sensor. Trans American Society of Artificial Internal Organs 34:255-258.

Leypoldt et al. 1984. Model of a two-substrate enzyme electrode for glucose. Analytical Chemistry 56:2896-2904

Linke et al. 1994. Amperometric biosensor for in vivo glucose sensing based on glucose oxidase immobilized in a redox hydrogel. Biosensors & Bioelectronics 9:151-158.

Lowe 1984. Biosensors, Trends in Biotechnology 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. 2008. Progress toward an in vivo surface-enhanced raman spectroscopy glucose sensor. Diabetes Technology & Therapeutics 10(4):257-265.

Maidan et al. 1992, Elimination of Electrooxidizable Interferent-Produced Currents in Amperometric Biosensors. Analytical Chemistry 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45(9):1651-1658.

Maran et al. 2002. Continuous subcutaneous glucose monitoring in diabetic patients: A multicenter analysis. Diabetes Care 25(2):347-352.

March W. F. 2002. Dealing with the delay. Diabetes Technology & Therapeutics 4(1):49-50.

Marena et al. 1993. The artifical endocrine pancreas in clinical practice and research. Panminerva Medica 352):67-74.

Markwell Medical, 1990. Direct 30-30® Blood Glucose Sensor Catalog © 1990 ELCO Diagnostics Company (1 page).

Mascini et al. 1989. Glucose electrochemical probe with extended linearity for whole blood. J Pharm Biomed Anal 7(12): 1507-1512.

Mastrototaro et al. 1991. An electroenzymatic glucose sensor fabricated on a flexible substrate. Sensors & Actuators B 5:139-44.

Mastrototaro et al. 2003. Reproducibility of the continuous glucose monitoring system matches previous reports and the intended use of the product. Diabetes Care 26:256; author reply p. 257.

Mastrototaro J. J. 2000. The MiniMed continuous glucose monitoring system. Diabetes Technology & Therapeutics 2(Suppl. 1):S13-S18.

Matsumoto et al, 1998. A micro-planar amperometeric glucose sensor unsusceptible to interference species. Sensors & Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profiled analysis. Diabetes Technology & Therapeutics 10:149-159.

McCartney et al. 2001. Near-infrared fluorescence lifetime assay for serum glucose based on allophycocyanin-labeled concanavalin A. Analytical Biochemistry 292:216-221.

McGrath et al. 1995. The use of differential measurements with a glucose biosensor for interference compensation during glucose determinations by flow injection analysis. Biosensors & Bioelectronics 10:937-943.

McKean et al. Jul. 7, 1988. A Telemetry Instrumentation System for Chronically Implanted Glucose and Oxygen Sensors. Trans Biomed Eng (BME) 35:526-532.

Memoli et al. 2002. A comparison between different immobilised glucoseoxidase-based electrodes. J Pharm Biomed Anal 29:1045-1052.

Merriam-Webster Online Dictionary. Apr. 23, 2007. Definition of "nominal". http:--www.merriam-webster.com-dictionary-nominal.

Merriam-Webster Online Dictionary. Definition of "acceleration". http:--www.merriam-webster.com-dictionary-Acceleration Jan. 11, 2010.

Merriam-Webster Online Dictionary. Definition of "system". http:--www.merriam-webster.com-dictionary-System Jan. 11, 2010.

Meyerhoff et al. 1992, On line continuous monitoring or subcutaneous tissue glucose in men by combining portable glucosensor with microdialysis. Diabetologia 35:1087-1092.

Moatti-Sirat et al. 1994. Reduction of acetaminophen interference in glucose sensors by a composite Nafion membrane: demonstration in rats and man. Diabetologia 37(6)610-616.

Moatti-Sirat et al, 1992. Evaluating in vitro and in vivo the interference of ascorbate and acetaminophen on glucose detection by a needle-type glucose sensor. Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Morff et al. 1990. Microfabrication of reproducible economical electroenzymatic glucose sensors. Annual International Conference of the IEEE Engineering in Medicine and Biology Society 12(2):0483-0484.

Mosbach et al. 1975. Determination of heat changes in the proximity of immobiiized enzymes with an enzyme termistor and its use for the assay of metaboiites. Biochimica Biophysica Acta (Enzymology) 403:256-265.

Motonaka et al. 1993. Determination of cholesterol and cholesterol ester with novel enzyme microsensors. Analytical Chemistry 65:3258-3261.

Moussy et al. 1993. Performance of subcutaneously implanted needle-type glucose sensors employing a novel trilayer coating. Analytical Chemistry 85: 2072-2077.

Moussy Francis, Nov. 2002. Implantable Glucose Sensor: Progress and Problems. Sensors 1:270-273.

Murphy et al. 1992. Polymer membranes in clinical sensor applications. II. The design and fabrication of pennselective hydrogels for electrochemical devices. Biomaterials 13(14):979-990.

Muslu, 1991. Trickling filter performance. Applied Biochemistry & Biotechnology 37:211-224.

Nation® 117 Solution Product Description Product No. 70160 Sigma-Aldrich Corp. St. Louis MO. Downloaded from https:--www.signaaldrich.com-cgi-bin-hsrun-Suite7-Suite-HAHTpage-Suite.HsExternal Prod . . . on Apr. 7, 2005.

Ohara et al. 1994. "Wired" enzyme electrodes for amperometric determination of glucose or lactate in the presence of interfering substances. Analytical Chemistry 66:2451-2457.

Ohara et al. Dec. 1993. Glucose electrodes based on cross-linked bis(22'-bipyridine)chloroosmium(+-2+) complexed poly(1-vinylimidazole) films. Analytical Chemistry 65:3512-3517.

Okuda et al. 1971. Mutarotase effect on micro determinations of D-glucose and its anomers with p-D-glucose oxidase. Analytical Biochemistry 43:312-315.

Oxford English Dictionary Online. Definition of "impending". http:--www.askoxford.com-results-?view=dev dict&field-12668446 Impending&branch=Jan. 11, 2010.

Palmisano et al. 2000. Simultaneous monitoring of glucose and lactate by an interference and cross-talk free dual electrode amparometric biosensor based on electropolymerized thin films. Biosensors & Bioelectronics 15:531-539.

(56) References Cited

OTHER PUBLICATIONS

Park et al. 2002. Gas separation properties of polysiloxane-polyether mixed soft segment urethane urea membranes. J Membrane Science 204:257-269.
Patel et al. 2003. Amoerometric glucose sensors based on ferrocene containing polymeric electron transfer systems—a preliminary report. Biosensors & Bioelectronics 18:1073-1076.
Peacock et al. 2008. Cardiac troponin and outcome in acute heart failure. NEJM 358: 2117-2126.
Pegoraro et al. 1995. Gas transport properties of siloxane polyurethanes. J Applied Polymer Science 57:421-429.
Pfeiffer E.F. 1990. The glucose sensor: the missing link in diabetes therapy. Horm. Metabolism Research Suppl. 24:154-164.
Pfeiffer et al. 1992. On line continuous monitoring of subcutaneous tissue glucose is feasible by combining portable glucosensor with microdialysis. Horm. Metabolism Research 25:121-124.
Pichert et al. 2000. Issues for the coming age of continuous glucose monitoring. Diabetes Educator 26(6):969-980.
Pickup et al. 1987-88. Implantabie glucose sensors: choosing the appropriate sensing strategy. Biosensors 3:335-346.
Pickup et al. 1989. Potentially-implantable amperometric glucose sensors with mediated electron transfer: improving the operating stability. Biosensors 4:109-119.
Pickup et al. 1989. In vivo molecular sensing in diabetes mellitus: an implantable glucose sensor with direct electron transfer. Diabetologia 32:213-217.
Pickup et al. 1993. Developing glucose sensors for in vivo use. TIBTECH vol. 11: 285-291.
Pinner et al. 1959. Cross-linking of cellulose acetate by ionizing radiation. Nature 184:1303-1304.
Pishko et al. 1991. Amperometric giucose microelectrodes prepared through immobilization of glucose oxidase in redox hydrogels. Analytical Chemistry 63:2268-2272.
Pitzer et al. 2001. Detection of hypoglycemia with the GlucoWatch biographer. Diabetes Care 24(5):881-885.
Poitout et al. 1991. In Vitro and In Vivo Evaluation in Dogs of a Miniaturized Glucose Sensor ASAIO Transactions 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode. Electrochimica Acta 26(5):725-729.
Quinn et al. 1995, Kinetics of glucose delivery to subcutaneous tissue in rats measured with 0.3-mm amperometric microsensors. Am J Physiol 269(1 Pt 1):E155-E161.
Quinn et al. 1997. Biocompatible glucose-permeable hydrogel for in situ coating of implantable biosensors. Biomaterials 18:1665-1670.
Rabah et al. 1991. Electrochemical wear of graphite anodas during electrolysis of brine. Carbon 29(2):165-171.
Reach et al. 1986. A Method for Evaluating in vivo the Functional Characteristics of Glucose Sensors. Biosensors 2:211-220.
Reach et al. 1992, Can continuous glucose monitoring be used for the treatment of diabetes? Analytical Chemistry 64(5):381-386.
Reach C. 2001. Which threshold to detect hypoglycemia? Value of receiver-operator curve analysis to find a compromise between sensitivity and specificity. Diabetes Care 24(5):803-804.
Reach Gerard. 2001. Letters to the Editor Re: Diabetes Technology & Therapeutics 2009; 2:49-56. Diabetes Technology & Therapeutics 3(1):129-139.
Rebrin et al. 1989. Automated feedback control of subcutaneous glucose concentration in diabetic dogs. Diabetologia 32:573-576.
Rebrin et al. 1992. Subcutaneous glucose monitoring by means of electrochemical sensors: fiction or reality? J Biomed Eng 14:33-40.
Reusch. 2004. Chemical Reactivity. Organometallic Compounds. Virtual Textbook of Organic Chem. pp. 1-16 http:--www.cem.msu.edu—~reusch-VirtualText-orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008, Real-time continuous glucose monitoring together with telemedical assistance improves glycemic control and glucose stability in pump-treated patients. Diabetes Technology & Therapeutics 10:194-199.
Rivers et al. 2001. Central venous oxygen saturation monitoring in the critically ill patient. Current Opinion in Critical Care 7:204-211.
Sakakida et al. 1992, Development of Ferrocene-Mediated Needle-Type Glucose Sensor as a Measure of True Subcutaneous Tissue Glucose Concentrations. Artificial Organs Today 2(2): 145-158.
Sakakida et al. 1993. Fetrocene-Mediated Needle Type Glucose Sensor Covered with Newly Designed Biocompatible Membrane. Sensors & Actuators B 13-14:319-322.
Salardi et al. 2002. The glucose area under the profiles obtained with continuous glucose monitoring system relationships with HbA1c in pediatric type 1 diabetes patients. Diabetes Care 25(10):1840-1844.
Samuels. 2004. The effects of flight and altitude. Arch Dis Child. 89: 448-455.
San Diego Plastics Inc. 2009. Polyethylene Data Sheet http:--www.sdplastics.com-polyeth.html.
Sansen et al. 1985. Glucose sensor with telemetry system. Chapter 12, pp. 167-475 in Ko W. H. (Ed). Implantable Sensors for Closed Lamp Prosthetic Systems, Futura Publishing Company, Inc., Mt. Kisco, NY.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. 1998. Measurement and modeling of the transient difference between blood and subcutaneous glucose concentrations in the rat after injection of insulin. PNAS USA 95:294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990. Development of a potentially wearable glucose sensor for patients with diabetes mellitus: design and in-vitro evaluation. Biosensors & Bioelectronics 5:37-46.
Service et al. 1970. Mean amplitude of glycemic excursions a measure of diabetic instability. Diabetes 19:644-655.
Service et al. 1987. Measurements of glucose control. Diabetes Care 10: 225-237.
Service R. F. 2002. Can sensors make a home in the body? Science 297:962-963.
Sharkawy et al. 1996. Engineering the tissue which encapsulates subcutaneous implants. I. Diffusion properties. J Biomed Matls Research Res 37:401-412.
Shaw et al. 1991. In vitro testing of a simply constructed highly stable glucose sensor suitable for implantation in diabetic patients. Biosensors &. Bioelectronics 6:401-406.
Shichiri et al. 1982. Wearable artificial endocrine pancreas with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas. Implantable Sensors. Chapter 15, pp. 197-210 in Implantable Sensers for Closed-Loop prosthetic Systems, Wen H. Ko, Ed., Futura Publishing Company, Inc., Mt. Kisco, NY.
Shichiri et al. 1986. Telemetry Glucose Monitoring Device with Needle-Type Glucose Sensor: A Useful Tool for Blood Glucose Monitoring in Diabetic Individuals. Diabetes Care Inc. 9(3):298-301.

(56) References Cited

OTHER PUBLICATIONS

Shichiri et al. 1989. Membrane Design for Extending the Long-Life of an Implantable Glucose Sensor. Diabetes Nutrition & Metabolism 2:309-313.
Shults et al. 1994. A telemetry-instrumentation system for monitoring multiple subcutaneously implanted glucose sensors. IEEE Trans Biomed Eng (BME) 41(10):937-942.
Skyler J. S. 2000. The economic burden of diabetes and the benefits of improved glycemic control: The potential role of a continuous glucose monitoring system. Diabetes Technology & Therapeutics 2(Suppl 1):S7-S12.
Slater-Maclean et al, 2008. Accuracy of glycemic measurements in the critically ill. Diabetes Technology & Therapeutics 10:169-177.
Smith et al. 1991. A Comparison of Islet Transplantation and Subcutaneous Insulin Injections for the Treatment of Diabetes Mellitus. Comput Biol Med. 21(6):417-427.
Sokol et al. 1980. Immobilized-enzyme rate-determination method for glucose analysis. Clinical Chemistry 26(1):89-92.
Sriyudthsak et al. 1996. Enzyme-epoxy membranes based glucose analyzing system and medical applications. Biosensors & Bioelectronics 11:735-742.
Steil et al. 2003. Determination of plasma glucose excursions with a subcutaneous glucose sensor. Diabetes Technology & Therapeutics 5(1):27-31.
Stern et al. 1957. Electrochemical polarization: 1. A theoretical analysis of the shape of polarization curves. J Electrochemical Society 104(1):56-63.
Sternberg et al. 1988, Covalent enzyme coupling on cellulose acetate membranes for glucose sensor development. Analytical Chemistry 60: 2781-2786.
Sternberg et al. 1988. Study and Development of Multilayer Needle-type Enzyme-based Glucose Mlorosensors. Biosensors 4:27-40.
Street et al. Dec. 2004. Islet Graft Assessment in the Edmonton Protocol: Implications for Predicting Long-Term Clinical Outcome Diabetes 53: 3107-3114.
Sumino T et al. 1998. Preliminary study of continuous glucose monitoring with a microdiaiysis technique. Proceedings of the IEEE Eng in Med Biol Soc 20(4):1775-1778.
Takegami et al. 1992. Pervaporatlon of ethanol water mixtures using novel hydrophobic membranes containing polydimethylsiloxane. J Membrane Science 75:93-105.
Tanenberg et al. 2000. Continuous glucose monitoring system: A new approach to the diagnosis of diabetic gastroparesis. Diabetes Technology & Therapeutics 2(Suppl 1):S73-S80.
Tatsuma et al. 1991. Oxidase-peroxidase bilayer-modified electrodes as sensors for lactate pyruvnte cholesteral and uric acid. Analytica Chimica Acta 242:85-39.
Thome et al. 1995 Can the decrease in subcutaneous glucose concentration precede the decrease in blood glucose level? Proposition for a push-pull kinetics hypothesis. Horm. Metabolism Research 27:53 [Abstract].
Thome-Duret et all 1996. Modification of the sensitivity of glucose sensor implanted into subcutaneous tissue. Diabetes Metabolism 22:174-178.
Thome-Duret et al. 1996. Use of a subcutaneous glucose sensor to detect decreases in glucose concentration prior to observation in blood. Analytical Chemistry 68:3822-3826.
Thome-Duret et al. 1998. Continuous glucose monitoring in the free-moving rat. Metabolism 47:799-803.
Thompson et al. 1986. In Vivo Probes: Problems and Perspectives, Clinical Biochemistry 19(5):255-261.
Tierney et al. 2000. Effect of acetaminophen on the accuracy of glucose measurements obtained with the GlucoWatch biographer. Diabetes Technology & Therapeutics 2:199-207.
Tierney et al. 2000, The GluoWatch® biographer: A frequent automatic and noninvasive glucose monitor. Ann. Med. 32:632-641.
Torjman et al. 2008. Glucose monitoring in acute care: technologies on the horizon. Journal of Diabetes Science and Technology 2(2):173-181.
Trecroci D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnology & Bioengineering 29:705-713.
Turner and Pickup 1985. Diabetes mellitus: biosensors for research and management. Biosensors 1:85-115.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta 163:161-174.
Unger et al. 2004. Glucose control in the hospitalized patient. Emergency Medicine 36(9):12-18.
Updike et al. 1967. The enzyme electrode. Nature 214:986-988.
Updike et al. 1988. Laboratory Evaluation of New Reusable Blood Glucose Sensor. Diabetes Care 11:801-807.
Updike et al. 1994. Enzymatic glucose sensor: Improved long-term performance in vitro and in vivo. ASAIO Journal 40(2):157-163.
Updike et al. 1997. Principles of long-term fully implanted sensors with emphasis on radiotelemetric monitoring of blood glucose form inside a subcutaneous foreign body capsule (FBC). Chapter 4, pp. 117-137 in Fraser ed. Biosensors in the Body, New York. John Wiley & Sons.
Updike et al. 2000, A subcutaneous glucose sensor with improved longevity dynamic range and stability of calibration. Diabetes Care 23(2):208-214.
Utah Medical Products Inc., 2003. Blood Pressure Transducers product specification (6 pages).
Vadgama P. Nov. 1981. Enzyme electrodes as practical biosensors. J Medical Engineering & Technology 5(6):293-298.
Vadgama, 1988. Diffusian limited enzyme electrodes. NATO ASI Series: Series C Math and Phys. Sci. 226:359-377.
Van den Berghe 2004. Tight biood glucose control with insulin in "real-life" intensive cares. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomedica Biochimica Acta 48(11-12):957-964.
Von Woedtke et al. 1989. In situ calibration of implanted electrochemical glucose sensors. Biomedica Biochimica Acta 48(11-12):943-952.
Wagner et al. 1998. Continuous amperometric monitoring of glucose in a brittle diabetic chimpanzee with a miniature subcutaneous electrode. PNAS USA 95:6379-6382.
Wang et al. 1994. Highly Selective Membrane-Free Mediator-Free Glucose Biosensor. Analytical Chemistry 66:3600-3603.
Wang et al. 1997. Improved ruggedness for membrane-based amperometric sensors using a pulsed amperometric method. Analytical Chemistry 69:4482-4489.
Wang. 2007. Electrochemical Glucose Biosensors. American Chemical Society Chemical Reviews Published on Web Dec. 23, 2007 p. est. 11.1 pp. 1-12; 10.1021-cr068123a.
Ward et al. 2000. Rise in background current overtime in a subcutaneous glucose sensor in the rabbit: Relevance to calibration and accuracy. Biosensors & Bioelectronics 15:53-61.
Ward et al. 2000. Understanding Spontaneous Output Fluctuations of an Amperometric Glucose Sensor: Effect of Inhalation Anesthesia and use of a Nonenzyme Containing Electrode. ASAIO J 46:540-546.
Ward et al. 2002. A new amperometric glucose microsensor: In vitro and short-term in vivo evaluation. Biosensors & Bioelectronics 17:181-189.
Ward et al. 2004. A wire-based dual-analyte sensor for Glucose and Lactate: In Vitro and In Vivo Evaluation Diabetes Technoiogy & Therapeutics 6(3):389-401.
Wientjes K. J. C. 2000. Development of a glucose sensor for diabetic patients (PhD. Thesis).
Wikipedia 2006. "Intravenous therapy" http:--en.wikipedia.org-wiki-Intravenous_therapy Aug. 15, 2006 (6 pages).
Wiley Electrical and Electronics Engineering Dictionary, 2004. John Wiley & Sons Inc. pp. 141-142, 548-549.

(56) References Cited

OTHER PUBLICATIONS

Wilkins et al. 1988. The coated wire electrode glucose sensor. Horm. MetabResearch Suppl. 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosensors & Bioelectronics 10:485-494.
Wiison et al. 1992. Progress toward the development of an implantable sensor for glucose. Clinical Chemistry 38(9):1613-1617.
Wilson et al. 2000. Enzyme-based biosensors for in vivo measurements. Chem. Rev. 100:2693-2704.
Wood W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor, Diabetes Care 5:278-281.
Worsley et al. 2008. Measurement of glucose in blood with a phenylboronic acid optical sensor. J Diabetes Science & Technology 2(2):213-220.
Wright et al. 1999. Bioelectrochemical dehalogenations via direct electrochemistry of poly(ethylene oxide)-modified myoglobin. Electrochemistry Comm 1:603-611.
Wu et al. 1999. In situ electrochemical oxygen generation with an immunoisolation device. Ann NY Acad Sci 875:105-125.
Yamasaki et al. 1989. Direct measurement of whole blood glucose by a needle-type sensor. Ciinica Chimica Acta 93:93-98.
Yamasaki Yoshimitsu. Sep. 1984. The development of a needle-type glucose sensor for wearable artificial endocrine pancreas. Medicai J Osaka University 35(1-2):25-34.
Yang et al. 1996. A glucose biosenser based on an oxygen electrode: In-vitro performances in a model buffer solution and in blood plasma. Biomedical Instrumentation & Technology 30:55-61.
Yang et al. 1997. Polyelectrolyte and molecular host ion self-assembly to multilayer thin films: An approach to thin film chemical sensors. Sensors and Actuators B 45:87-92.
Yang et al. 1998. Development of needle-type glucose sensor with high selectivity. Sensors & Actuators B 46:249-256.
Yang et al. 2004. A Comparison of Physical Properties and Fuel Cell Performance of Nafion and Zirconium Phosphate-Nation Composite Membrane. J Membrane Science 237:145-161.
Ye et al. 1993. High Current Density 'Wired' Quinoprotein Glucose Dehydrogenase Electrode. Analytical Chemistry 65:238-241.
Zamzow et al. 1990. Development and evaluation of a wearable blood glucose monitor. ASAIO Transa 36:M588-M591.
Zethelius et al. 2008. Use of multiple biomarkers to improve the prediction of death from cardiovascular causes. NEJM 358:2107-2116.
Zhang et al 1993. Electrochemical oxidation of H202 on Pt and Pt + Ir electrodes in physiological buffer and its applicability to H202-based biosensors. J Electroanalytical Chemistry 345:253-271.
Zhang et al. 1993. In vitro and in vivo evaluation of oxygen effects on a glucose oxidase based implantable glucose sensor. Analytica Chimica Acta 281:513-520.
Zhang et al. 1994. Elimination of the acetaminophen interference in an implantable glucose sensor. Analytical Chemistry 66(7):1183-1188.
Zhu et al. 1994. Fabrication and characterization of glucose sensors based on a microarray H202 electrode. Biosensors & Bioelectronics 9:295-300.
Zhu et al. 2002. Planar amperometric glucose sensor based on glucose oxidase immobilized by chitosan film on prussian blue layer. Sensors 2:127-136.
PCT-US2009-057347, filed Sep. 17, 2009: International Preliminary Report on Patentability dated Mar. 22, 2011.
PCT-US2009-057347, filed Sep. 17, 2009: International Search Report and Written Opinion dated Apr. 1, 2010.
U.S. Appl. No. 09/447,227: Office Action dated Aug. 15, 2001.
U.S. Appl. No. 09/447,227: Office Action dated Jan. 17, 2002.
U.S. Appl. No. 09/447,227: Office Action dated Jul. 15, 2002.
U.S. Appl. No. 09/447,227: Office Action dated Jan. 16, 2003.
U.S. Appl. No. 09/447,227: Office Action dated Nov. 28, 2003.
U.S. Appl. No. 09/447,227: Office Action dated Jul. 9, 2003.
U.S. Appl. No. 09/447,227: Office Action dated Sep. 22, 2005.
U.S. Appl. No. 09/447,227: Office Action dated Aug. 1, 2006.
U.S. Appl. No. 09/447,227: Office Action dated Apr. 4, 2006.
U.S. Appl. No. 09/447,227: Office Action dated Mar. 9, 2007.
U.S. Appl. No. 09/447,227: Office Action dated Jul. 17, 2007.
U.S. Appl. No. 09/447,227: Office Action dated Jan. 23, 2008.
U.S. Appl. No. 09/447,227: Office Action dated Jun. 12, 2008.
U.S. Appl. No. 09/447,227: Office Action dated Dec. 11, 2008.
U.S. Appl. No. 09/447,227: Office Action dated May 26, 2009.
U.S. Appl. No. 09/447,227: Office Action dated Dec. 8, 2009.
U.S. Appl. No. 09/447,227: Office Action dated Jan. 14, 2010.
U.S. Appl. No. 09/636,369: Office Action dated Sep. 30, 2002.
U.S. Appl. No. 09/916,711: Office Action dated Sep. 24, 2003.
U.S. Appl. No. 09/916,711: Office Action dated Feb. 11, 2004.
U.S. Appl. No. 09/916,711: Office Action dated Jul. 23, 2004.
U.S. Appl. No. 09/916,711: Office Action dated Dec. 23, 2004.
U.S. Appl. No. 09/916,711: Office Action dated Jul. 1, 2005.
U.S. Appl. No. 09/916,711: Office Action dated Feb. 14, 2006.
U.S. Appl. No. 09/916,711: Office Action dated Sep. 5, 2006.
U.S. Appl. No. 10/153,356: Office Action dated Feb. 17, 2004.
U.S. Appl. No. 10/153,356: Office Action dated Aug. 12, 2004.
U.S. Appl. No. 10/153,356: Office Action dated Mar. 15, 2005.
U.S. Appl. No. 10/153,356: Office Action dated Oct. 6, 2005.
U.S. Appl. No. 10/153,356: Office Action dated Mar. 10, 2006.
U.S. Appl. No. 10/153,356: Office Action dated Aug. 29, 2006.
U.S. Appl. No. 10/153,356: Office Action dated Mar. 7, 2007.
U.S. Appl. No. 10/695,636: Office Action dated Dec. 6, 2005.
U.S. Appl. No. 10/695,636: Office Action dated May 22, 2006.
U.S. Appl. No. 10/695,636: Office Action dated Mar. 14, 2007.
U.S. Appl. No. 10/789,359: Office Action dated Mar. 20, 2008.
U.S. Appl. No. 10/789,359: Office Action dated Oct. 3, 2008.
U.S. Appl. No. 10/789,359: Office Action dated Nov. 27, 2008.
U.S. Appl. No. 10/838,658: Office Action dated Dec. 15, 2008.
U.S. Appl. No. 10/838,658: Office Action dated Jul. 30, 2009.
U.S. Appl. No. 10/838,909: Office Action dated Jun. 5, 2008.
U.S. Appl. No. 10/838,909: Office Action dated Mar. 16, 2009.
U.S. Appl. No. 10/885,476: Office Action dated Dec. 24, 2008.
U.S. Appl. No. 10/885,476: Office Action dated Jun. 23, 2009.
U.S. Appl. No. 10/896,639: Office Action dated Sep. 23, 2005.
U.S. Appl. No. 10/896,639: Office Action dated Apr. 6, 2006.
U.S. Appl. No. 10/896,639: Office Action dated Aug. 22, 2006.
U.S. Appl. No. 10/896,639: Office Action dated Apr. 11, 2007.
U.S. Appl. No. 10/896,639: Office Action dated Oct. 5, 2007.
U.S. Appl. No. 10/896,772: Office Action dated Jan. 11, 2005.
U.S. Appl. No. 10/896,772: Office Action dated Jul. 19, 2005.
U.S. Appl. No. 10/896,772: Office Action dated Dec. 14, 2005.
U.S. Appl. No. 10/896,772: Office Action dated May 22, 2006.
U.S. Appl. No. 10/991,966: Office Action dated Nov. 28, 2007.
U.S. Appl. No. 10/991,966: Office Action dated Jul. 22, 2008.
U.S. Appl. No. 10/991,353: Office Action dated Sep. 12, 2008.
U.S. Appl. No. 10/991,353: Office Action dated Mar. 4, 2009.
U.S. Appl. No. 10/991,353: Office Action dated Jul. 31, 2009.
U.S. Appl. No. 10/991,353: Office Action dated Jan. 14, 2010.
U.S. Appl. No. 11/007,635: Office Action dated Jan. 27, 2006.
U.S. Appl. No. 11/034,344: Office Action dated Jan. 15, 2008.
U.S. Appl. No. 11/077,693: Office Action dated Jun. 27, 2008.
U.S. Appl. No. 11/007,693: Office Action dated Dec. 26, 2008.
U.S. Appl. No. 11/007,693: Office Action dated Sep. 4, 2009.
U.S. Appl. No. 11/077,713: Office Action dated May 5, 2008.
U.S. Appl. No. 11/077,713: Office Action dated Feb. 10, 2009.
U.S. Appl. No. 11/077,713: Office Action dated Sep. 2, 2009.
U.S. Appl. No. 11/077,713: Office Action dated Jan. 20, 2010.
U.S. Appl. No. 11/077,714: Office Action dated Oct. 11, 2006.
U.S. Appl. No. 11/077,714: Office Action dated Apr. 10, 2007.
U.S. Appl. No. 11/077,714: Office Action dated Jul. 27, 2007.
U.S. Appl. No. 11/077,714: Office Action dated Jan. 10, 2008.
U.S. Appl. No. 11/077,714: Office Action dated Sep. 16, 2008.
U.S. Appl. No. 11/077,714: Office Action dated Apr. 16, 2009.
U.S. Appl. No. 11/077,714: Office Action dated Dec. 31, 2009.
U.S. Appl. No. 11/077,714: Office Action dated Jan. 27, 2010.
U.S. Appl. No. 11/077,759: Office Action dated May 17, 2007.

(56) References Cited

OTHER PUBLICATIONS

U.S. Appl. No. 11/077,759: Office Action dated Mar. 31, 2008.
U.S. Appl. No. 11/077,759: Office Action dated Jul. 10, 2008.
U.S. Appl. No. 11/077,759: Office Action dated May 26, 2009.
U.S. Appl. No. 11/078,072: Office Action dated Sep. 2, 2009.
U.S. Appl. No. 11/078,072: Office Action dated Feb. 18, 2010.
U.S. Appl. No. 11/078,232: Office Action dated May 5, 2008.
U.S. Appl. No. 11/078,232: Office Action dated Nov. 12, 2008.
U.S. Appl. No. 11/078,232: Office Action dated Mar. 5, 2009.
U.S. Appl. No. 11/078,232: Office Action dated Jul. 21, 2009.
U.S. Appl. No. 11/078,232: Office Action dated Jan. 5, 2010.
U.S. Appl. No. 11/157,365: Office Action dated Jun. 26, 2008.
U.S. Appl. No. 11/157,365: Office Action dated Jan. 7, 2009.
U.S. Appl. No. 11/157,365: Office Action dated Jul. 21, 2009.
U.S. Appl. No. 11/157,365: Office Action dated Jan. 21, 2010.
U.S. Appl. No. 11/280,672: Office Action dated Dec. 10, 2008.
U.S. Appl. No. 11/280,672: Office Action dated Jun. 2, 2009.
U.S. Appl. No. 11/280,672: Office Action dated Oct. 29, 2009.
U.S. Appl. No. 11/280,672: Office Action dated Mar. 11, 2010.
U.S. Appl. No. 11/333,837: Office Action dated Nov. 28, 2008.
U.S. Appl. No. 11/333,837: Office Action dated Jun. 29, 2009.
U.S. Appl. No. 11/334,876: Office Action dated Oct. 4, 2006.
U.S. Appl. No. 11/334,876: Office Action dated Sep. 25, 2007.
U.S. Appl. No. 11/334,876: Office Action dated May 2, 2008.
U.S. Appl. No. 11/334,876: Office Action dated Aug. 25, 2009.
U.S. Appl. No. 11/334,876: Office Action dated Aug. 26, 2008.
U.S. Appl. No. 11/335,879: Office Action dated Jun. 26, 2008.
U.S. Appl. No. 11/335,879: Office Action dated Jan. 13, 2009.
U.S. Appl. No. 11/335,879: Office Action dated Jun. 16, 2009.
U.S. Appl. No. 11/360,252: Office Action dated Jun. 30, 2008.
U.S. Appl. No. 11/360,252: Office Action dated Jan. 29, 2009.
U.S. Appl. No. 11/360,252: Office Action dated Jul. 23, 2009.
U.S. Appl. No. 11/360,262: Office Action dated Jun. 22, 2009.
U.S. Appl. No. 11/360,819: Office Action dated Aug. 11, 2008.
U.S. Appl. No. 11/360,819: Office Action dated Dec. 26, 2008.
U.S. Appl. No. 11/360,819: Office Action dated Oct. 29, 2009.
U.S. Appl. No. 11/404,417: Office Action dated Jan. 23, 2009.
U.S. Appl. No. 11/404,481: Office Action dated Jul. 23, 2009.
U.S. Appl. No. 11/404,481: Office Action dated Jan. 29, 2010.
U.S. Appl. No. 11/411,656: Office Action dated Jul. 26, 2007.
U.S. Appl. No. 11/675,063: Office Action dated Dec. 3, 2008.
U.S. Appl. No. 11/675,063: Office Action dated Feb. 19, 2009.
U.S. Appl. No. 11/675,063: Office Action dated Jun. 10, 2009.
U.S. Appl. No. 11/692,154: Office Action dated Jan. 22, 2009.
U.S. Appl. No. 11/692,154: Office Action dated Jul. 8, 2009.
U.S. Appl. No. 12/113,508: Office Action dated Feb. 23, 2010.
U.S. Appl. No. 12/139,305: Office Action dated Jan. 13, 2010.

* cited by examiner

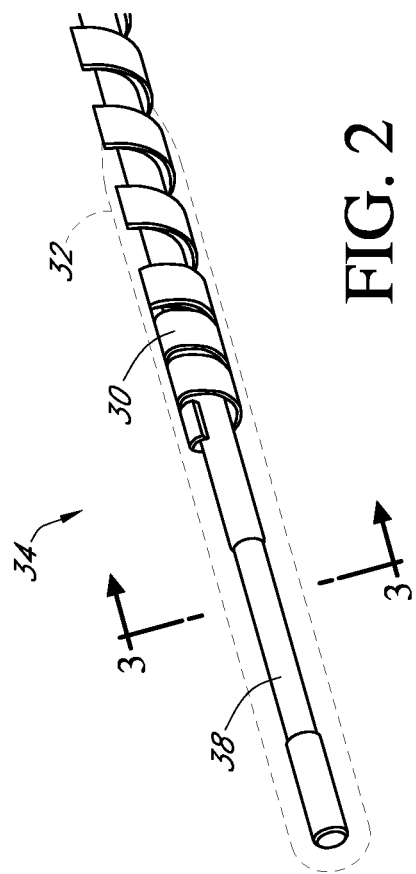
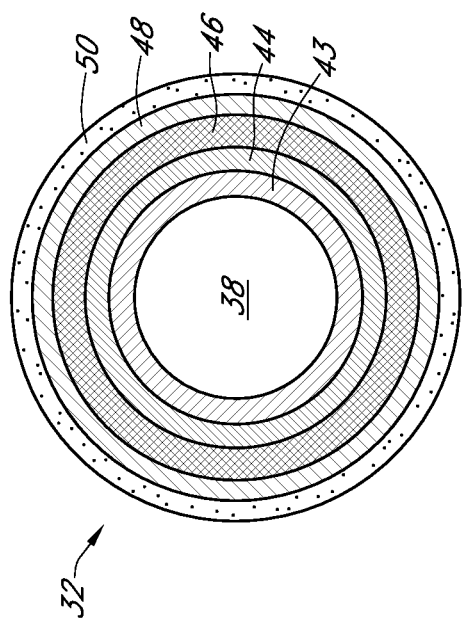
FIG. 2
FIG. 3

PARTICLE-CONTAINING MEMBRANE AND PARTICULATE ELECTRODE FOR ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/711,863, filed Sep. 21, 2017, which is a continuation of U.S. application Ser. No. 14/887,232, filed Oct. 19, 2015, now abandoned, which is a continuation of U.S. application Ser. No. 13/907,507, filed May 31, 2013, now U.S. Pat. No. 9,339,222, which is a continuation of U.S. application Ser. No. 12/562,011, filed Sep. 17, 2009, now U.S. Pat. No. 8,560,039, which claims the benefit of priority under 35 U.S.C. § 119(e) to U.S. Provisional Application No. 61/098,667, filed Sep. 19, 2008. Each of the aforementioned applications is incorporated by reference herein in its entirety, and each is hereby expressly made a part of this specification.

FIELD OF THE INVENTION

The preferred embodiments relate generally to analyte sensors and methods for measuring an analyte and/or a drug compound in a sample, such as a bodily fluid or tissue.

BACKGROUND OF THE INVENTION

It is routine, as part of today's medical practice, to detect and/or measure levels of a wide variety of analytes in biological samples (e.g., fluids, tissues and the like collected from patients) during the process of diagnosing, monitoring, and/or prognosticating a patient's medical status. Such tests are routinely conducted in a variety of medical settings (e.g., doctor's office, clinic, hospital, etc.) and in the home by the host and/or a caretaker.

Diabetes mellitus, a disorder in which the pancreas cannot create sufficient insulin (Type I or insulin dependent) and/or in which insulin is not effective (Type 2 or non-insulin dependent), is one medical condition, in which the standard of care involves routine testing of bodily fluid samples (e.g., blood, interstitial fluid) in order to ascertain the patient's (e.g., host's) glucose status, often by the host or a caretaker. In the diabetic state, the patient suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will typically only measure his or her glucose levels two to four times per day. Unfortunately, these time intervals may be spread so far apart that the diabetic will often find out too late a hyperglycemic or hypoglycemic episode, thereby potentially incurring dangerous side effects associated with a hyperglycemic or hypoglycemic condition. In fact, not only is it unlikely that a diabetic will take a timely SMBG value, but the diabetic will not know if his or her blood glucose value is rising or falling based on conventional methods, and thus inhibit his or her ability to make educated insulin therapy decisions.

SUMMARY OF THE INVENTION

In a first aspect, an analyte detection system for continuous in vivo detection of an analyte is provided, the system comprising: a continuous analyte sensor comprising a working electrode configured for implantation in a host, wherein the working electrode comprises an electroactive surface, the continuous analyte sensor further comprising a membrane located over the working electrode, wherein the membrane comprises an enzyme domain and a particle-containing domain, wherein the particle-containing domain comprises a conductive component dispersed in a non-conductive component, wherein the conductive component comprises a plurality of conductive particles, wherein the particle-containing domain is located more distal to the electroactive surface than the enzyme domain, and wherein the particle-containing domain is configured to electrochemically react with at least one interfering species; and sensor electronics configured to generate a signal associated with an analyte in the host.

In an embodiment of the first aspect, the conductive component comprises at least one material selected from the group consisting of platinum, platinum-iridium, iridium, palladium, graphite, gold, silver, silver chloride, carbon, and conductive polymers.

In an embodiment of the first aspect, particles comprise from about 10 wt. % to about 40 wt. % of the particle-containing domain.

In an embodiment of the first aspect, the non-conductive component comprises a polymer.

In an embodiment of the first aspect, the polymer comprises an analyte-permeable polymer.

In an embodiment of the first aspect, the analyte-permeable polymer comprises a hydrophilic polymer.

In an embodiment of the first aspect, the analyte-permeable polymer comprises at least one of polyurethane or silicone.

In an embodiment of the first aspect, the sensor electronics are configured to apply a potential to the particle-containing domain.

In an embodiment of the first aspect, the particle-containing domain is configured to electrochemically oxidize the one interfering species.

In an embodiment of the first aspect, the particle-containing domain is configured to electrochemically reduce the one interfering species.

In an embodiment of the first aspect, the particle-containing domain is configured to electrochemically react with an amount of interfering species, such that an interference component of the signal is less than about 20% of a total signal.

In an embodiment of the first aspect, the interference component of the signal is less than about 10% of the total signal.

In an embodiment of the first aspect, the interference component of the signal is less than about 5% of the total signal.

In an embodiment of the first aspect, the plurality of conductive particles comprise a plurality of positive particles and a plurality of negative particles, wherein the positive particles and negative particles are configured such that a positive particle and a negative particle form an electrochemical cell having a potential sufficient to render a interfering species molecule substantially unable to electrochemically react with the electroactive surface.

In an embodiment of the first aspect, the particles comprise between about 1-wt % and about 60-wt % of the particle-containing domain.

In an embodiment of the first aspect, the applied potential is from about 0.1V to about 0.8V.

In an embodiment of the first aspect, the applied potential is from about 0.6V to about 0.7V.

In an embodiment of the first aspect, the applied potential is oscillated between at least two potentials.

In an embodiment of the first aspect, the applied potential is pulsed.

In an embodiment of the first aspect, the applied potential is constant.

In an embodiment of the first aspect, the sensor is configured for implantation in a host.

In an embodiment of the first aspect, the particle-containing domain is disposed coaxially or coplanar with the working electrode.

In an embodiment of the first aspect, the enzyme domain comprises an enzyme configured to detect the analyte.

In an embodiment of the first aspect, the enzyme comprises glucose oxidase.

In an embodiment of the first aspect, the system further comprises a second working electrode configured to detect at least one of a non-analyte-related signal or another analyte.

In an embodiment of the first aspect, the conductive particles have an average weight between about $1 \times 10^{-17}$ grams and about $1 \times 10^{-10}$ grams.

In an embodiment of the first aspect, the conductive particles have an average surface area greater than about 20 $m^2/g$.

In a second aspect, a sensor system for measurement of a species in a host is provided, the sensor system comprising: an electrode configured for implantation in a host, the electrode comprising an electroactive surface; a membrane disposed over the electrode, the membrane comprising a particle-containing domain, wherein the particle-containing domain comprises a sensor element configured to measure a concentration of a species; and sensor electronics configured to generate a signal associated with a concentration of the species in the host.

In an embodiment of the second aspect, the membrane further comprises an enzyme-containing domain located adjacent to the particle-containing domain.

In an embodiment of the second aspect, the membrane further comprises an oxygen permeable domain located between the electroactive surface and the particle-containing domain.

In an embodiment of the second aspect, the electroactive surface is configured for generating oxygen.

In an embodiment of the second aspect, the particle-containing domain is a first sensor element configured to measure a concentration of a first species, and wherein the electrode is a second sensor element configured to measure a concentration of a second species.

In an embodiment of the second aspect, the first species and the second species each comprise at least one of an analyte or a drug.

In an embodiment of the second aspect, the particle-containing domain substantially reduces flow therethrough of at least one of the first species or the second species.

In an embodiment of the second aspect, the sensor electronics are configured to apply a first bias potential to the first sensor element and to apply a second bias potential to the second sensor element, and wherein the first bias potential and the second bias potential are different.

In a third aspect, a method for detecting a signal associated with an analyte is provided, the method comprising: providing a continuous analyte sensor configured for implantation into a tissue of a host, the continuous analyte sensor comprising a working electrode and a membrane located over the working electrode, wherein the membrane comprises an enzyme domain and a particle-containing domain, wherein the particle-containing domain is located more distal to the working electrode than the enzyme domain; electrochemically reacting the particle-containing domain with at least one interfering species; and detecting a signal from the continuous analyte sensor, wherein the signal is indicative of a concentration of an analyte.

In an embodiment of the third aspect, the continuous analyte sensor is configured to contact a biological sample.

In an embodiment of the third aspect, the membrane is configured to allow the analyte to diffuse therethrough.

In an embodiment of the third aspect, electrochemically reacting comprises applying a potential to the particle-containing domain.

In an embodiment of the third aspect, the particle-containing domain is configured to electrochemically oxidize with at least one interfering species.

In an embodiment of the third aspect, the particle-containing domain is configured to electrochemically reduce with at least one interfering species.

In an embodiment of the third aspect, the biological sample is from the host's circulatory system.

In an embodiment of the third aspect, the biological sample is from the host's extracellular fluid.

In an embodiment of the third aspect, electrochemically reacting comprises allowing at least one interfering species to diffuse at least partially through the particle-containing domain.

In an embodiment of the third aspect, electrochemically reacting comprises electrochemically reacting an amount of interfering species, such that an interference component of the signal is less than about 20% of the total signal.

In an embodiment of the third aspect, the interference component of the signal is less than about 10% of the total signal.

In an embodiment of the third aspect, the interference component of the signal is less than about 5% of the total signal.

In a fourth aspect, an analyte detection device is provided, comprising: a sensor configured for continuous in vivo detection of an analyte, the sensor comprising an electrode comprising at least one of a non-analyte-permeable or analyte-permeable material and a plurality of conductive particles distributed throughout the material, and a sensor membrane; and sensor electronics configured to generate a signal associated with the analyte.

In an embodiment of the fourth aspect, the material comprises a polymer.

In an embodiment of the fourth aspect, the polymer comprises a water-permeable polymer.

In an embodiment of the fourth aspect, the conductive particles comprise between about 1 wt % and about 60 wt % of the electrode.

In an embodiment of the fourth aspect, the conductive particles comprise at least one material selected from the group consisting of platinum, platinum-iridium, iridium, palladium, graphite, gold, silver, silver chloride, carbon, conductive polymers, and mixtures, alloys or nanocomposites thereof.

In an embodiment of the fourth aspect, the electrode comprises a configuration selected from the group consisting of a wire, a fiber, a string, a rod, an orb, a sphere, a ball, an egg, a pyramid, a cone, a cube, a rectangle, a polygon, and a polyhedron.

In an embodiment of the fourth aspect, the sensor further comprises a support and wherein the electrode is disposed on the support.

In an embodiment of the fourth aspect, the electrode comprises a film comprising the material and the plurality of conductive particles.

In an embodiment of the fourth aspect, the membrane system is disposed coaxially on the electrode.

In an embodiment of the fourth aspect, the sensor is configured for implantation in a host.

In an embodiment of the fourth aspect, the conductive particles have an average weight between $1 \times 10^{-17}$ grams and about $1 \times 10^{-10}$ grams.

In an embodiment of the fourth aspect, the conductive particles have an average surface area greater than about 20 $m^2/g$.

In an embodiment of the fourth aspect, the conductive particles have a concentration that is sufficient for the particle-containing domain to function as conductive film.

In an embodiment of the fourth aspect, the concentration of the conductive particles within the particle-containing domain, in volume percentage, is between about 15% and about 45% of a total volume of the particle-containing domain.

In an embodiment of the fourth aspect, an effective surface area of the particle-containing domain is more than about 3 times greater than an effective surface of a corresponding domain without conductive particles.

In an embodiment of the fourth aspect, the particle-containing domain has a glucose diffusion coefficient greater than about $1 \times 10^{-13}$ $m^2/s$.

In an embodiment of the fourth aspect, the particle-containing domain has an oxygen diffusion coefficient greater than about $1 \times 10^{-9}$ $m^2/s$.

In a fifth aspect, a method for manufacturing a continuous analyte detection device is provided, comprising: blending a plurality of conductive particles and a liquid polymer to form an electrode material; forming an electrode from the electrode material; and applying a membrane to the electrode.

In an embodiment of the fifth aspect, forming an electrode comprises extruding the electrode material.

In an embodiment of the fifth aspect, the electrode material is on a support.

In an embodiment of the fifth aspect, forming an electrode comprises molding the electrode material.

In an embodiment of the fifth aspect, blending comprises blending a plurality particles comprising at least one material selected from the group consisting of platinum, platinum-iridium, iridium, palladium, graphite, gold, silver, silver chloride, carbon, and a conductive polymer.

In an embodiment of the fifth aspect, blending comprises blending the plurality of conductive particles throughout a water-permeable liquid polymer.

In an embodiment of the fifth aspect, blending comprises blending the plurality of conductive particles throughout a water-impermeable liquid polymer.

In an embodiment of the fifth aspect, applying a membrane comprises applying an enzyme.

In a sixth aspect, a sensor system for measurement of a concentration of a first species and a concentration of a second species in a host is provided, the sensor system comprising: an electrode configured for implantation in a host, the electrode comprising a first sensor element configured to measure a concentration of a first species; a membrane, with a particle-containing domain, disposed over the electrode, wherein the membrane comprises a second sensor element configured to measure a concentration of a second species; and sensor electronics configured to generate a first signal associated with the first species in the host and configured to generate a second signal associated with the second species in the host.

In an embodiment of the sixth aspect, the first species comprises a drug and the second species comprises an analyte.

In an embodiment of the sixth aspect, the first species comprises an analyte and the second species comprises a drug.

In an embodiment of the sixth aspect, the first species comprises a first analyte and the second species comprises a second analyte.

In an embodiment of the sixth aspect, the particle-containing domain comprises the second sensor element.

In an embodiment of the sixth aspect, the particle-containing domain is located between the first sensor element and the second sensor element.

In an embodiment of the sixth aspect, the particle-containing domain substantially reduces flow therethrough of at least one of the first species or the second species.

In an embodiment of the sixth aspect, a first bias potential is applied to the first sensor element and a second bias potential is applied to the second sensor element, and wherein the first bias potential and the second bias potential are different.

BRIEF DESCRIPTION OF THE DRAWINGS

FIG. 2 is a perspective view of an in vivo portion of an analyte sensor, in one embodiment.

FIG. 3 is a cross-sectional view of the analyte sensor of FIG. 2, taken along line 3-3.

DETAILED DESCRIPTION OF THE PREFERRED EMBODIMENTS

Figure 1:
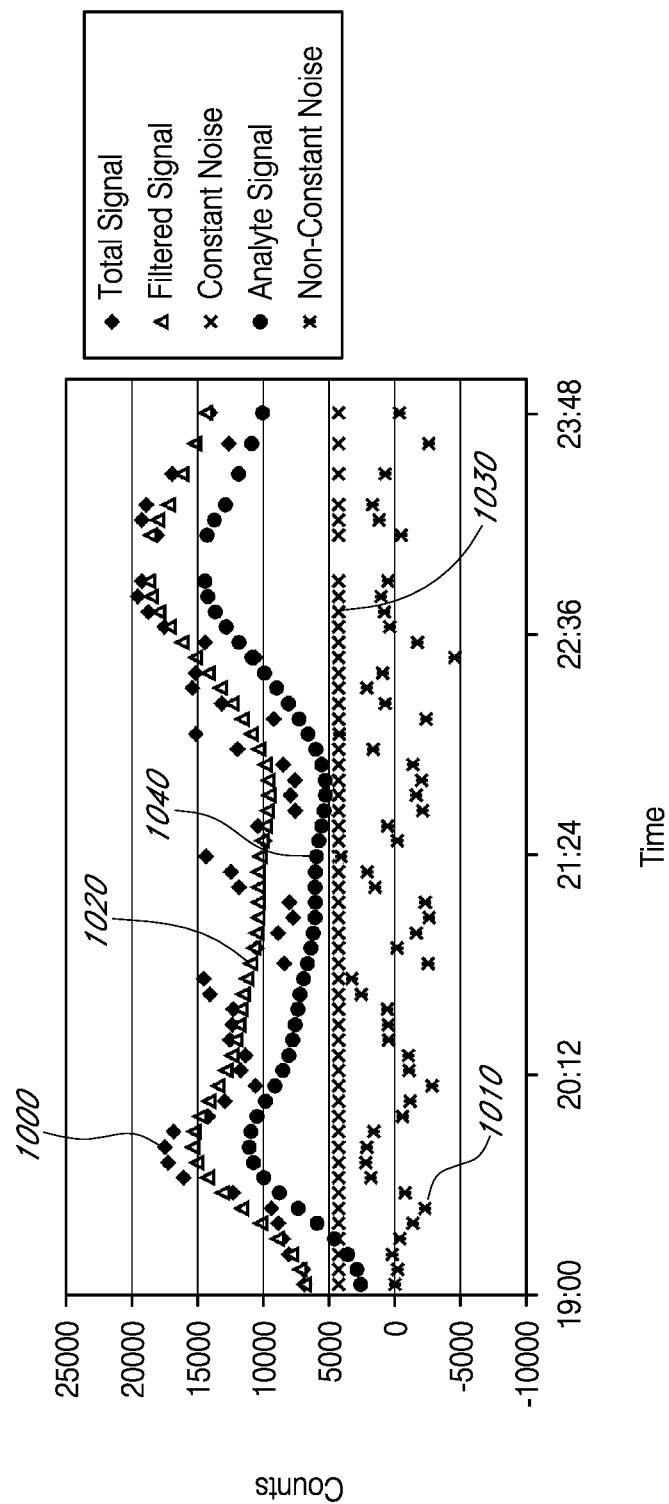
FIG. 1 is a graph illustrating the components of a signal measured by a transcutaneous glucose sensor (after sensor break-in was complete), implanted in a non-diabetic, human volunteer host.

The following description and examples describe in detail some exemplary embodiments. It should be understood that there are numerous variations and modifications of the devices, systems, and methods described herein that are encompassed by the present invention. Accordingly, the description of a certain exemplary embodiment should not be deemed to limit the scope of the present invention.

Definitions

In order to facilitate an understanding of the preferred embodiments, a number of terms are defined below.

The terms "physiological parameters" and "physiological boundaries" as used herein are broad terms, and are to be given their ordinary and customary meaning to a person of ordinary skill in the art (and are not to be limited to a special or customized meaning), and refer without limitation to the parameters obtained from continuous studies of physiological data in humans and/or animals. For example, a maximal sustained rate of change of glucose in humans of about 4 to 6 mg/dL/min and a maximum acceleration of the rate of change of about 0.1 to 0.2 mg/dL/min$^2$ are deemed physiologically feasible limits; values outside of these limits are considered non-physiological. As another example, it has been observed that the best solution for the shape of the curve at any point along a glucose signal data stream over a certain time period (for example, about 20 to 30 minutes) is a straight line, which can be used to set physiological limits. These terms are broad enough to include physiological parameters for any analyte.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); glucagon; ketones (e.g., acetone); ephedrine; terbutaline; $O_2$; $CO_2$; potassium; $PCO_2$; $PO_2$; sodium, hematocrit; reactive oxygen species; nitric oxide; diols; pyruvate dehydroxgenase; NADPH oxidase; xanthine oxidase; acyl CoA oxidase; plasma amine oxidase; bilirubin; cholesterol; creatinine; gentisic acid; ibuprofen; L-Dopa; methyl Dopa; salicylate; tetracycline; tolazamide; tolbutamide; human chorionic gonadotropin; anesthetic drugs (e.g., lidocaine); acetyl CoA; intermediaries in the Kreb's cycle (e.g., citrate, cis-aconitate, D-isocitrate, succinate, fumarate; malate, etc.); anti-seizure drugs (e.g., ACTH, lorazepam, carbamezepine, carnitine, Acetazolamide, Phenytoin sodium, depakote, divalproex sodium, tiagabine hydrochloride, levetiracetam, clonazepam, lamotrigine, nitrazepam, primidone, gabapentin, paraldehyde, phenobarbital, carbamazepine, topiramate, clorazepate dipotassium, oxcarbazepine, diazepam, Ethosuximide, Zonisamide); glutamine; cytochrome oxidase, heparin andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alcohol oxidase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (e.g., Immunoglobulin M, Immunoglobulin M, IgG adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "continuous analyte sensor" as used herein is a broad term, and is to be given its ordinary and customary meaning to a person of ordinary skill in the art (and is not to be limited to a special or customized meaning), and refers without limitation to a device that continuously or continually measures analyte concentration (e.g., glucose), for example, at time intervals ranging from fractions of a second up to, for example, about 1, 2, 5, 9, 10 minutes, or longer. It should be understood that continuous analyte sensors can continually measure glucose concentration without requiring user initiation and/or interaction for each measurement, such as described with reference to glucose in U.S. Pat. No. 6,001,067, for example.

The phrase "continuous glucose sensing" as used herein is a broad term, and is to be given its ordinary and customary meaning to a person of ordinary skill in the art (and is not to be limited to a special or customized meaning), and refers without limitation to the period in which monitoring of glucose concentration is continuously or continually performed, for example, at time intervals ranging from fractions of a second up to, for example, about 1, 2, 5, 9, 10 minutes, or longer.

The term "biological sample" as used herein is a broad term, and is to be given its ordinary and customary meaning to a person of ordinary skill in the art (and is not to be limited to a special or customized meaning), and refers without limitation to a sample of a host body, for example, blood, serum, plasma, interstitial fluid, cerebral spinal fluid, lymph fluid, ocular fluid, saliva, oral fluid, urine, sweat, excretions, or exudates; swabbed bodily samples, including oral, throat, genital and wound swabs; and solid or semi-solid bodily samples, including fecal samples, tissue, organs, suspension and/or cultures thereof, including cell and/or bacterial cultures thereof, and the like. The sample can be macerated, frozen, thawed, heated, dissolved, diluted, concentrated, amplified, extracted, filtered, separated/divided, cultured and the like, to produce a sample to be analyzed.

The term "host" as used herein is a broad term, and is to be given its ordinary and customary meaning to a person of ordinary skill in the art (and is not to be limited to a special or customized meaning), and refers without limitation to plants or animals, for example humans.

The term "biointerface membrane" as used herein is a broad term, and is to be given its ordinary and customary meaning to a person of ordinary skill in the art (and is not to be limited to a special or customized meaning), and refers without limitation to a membrane that interfaces with the host, such as but not limited to by physical contact with host blood, tissue, bodily fluid, and the like.

The term "membrane" as used herein is a broad term, and is to be given its ordinary and customary meaning to a person of ordinary skill in the art (and is not to be limited to a special or customized meaning), and refers without limitation to a thin layer of permeable or semi-permeable material applied to the sensor. A membrane can be comprised of one or more domains (e.g., layers) and is typically constructed of materials of a few microns thickness or more, which may be permeable to oxygen and are optionally permeable to glucose. In some embodiments, a membrane is formed of one layer having regions (e.g., stratifications), such as but not limited to functional regions, therein and/or thereon. In other embodiments, a membrane is formed of two or more layers, wherein one or more of the layers may be formed of different materials and/or have different functions. In one example, the membrane comprises an immobilized glucose oxidase enzyme, which enables an electrochemical reaction to occur to measure a concentration of glucose.

The term "domain" as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane. In one exemplary embodiment, a particle-containing domain is disposed more distal to a sensor's electroactive surface than the enzyme and is configured to electrochemically oxidize/reduce noise-causing species, such that the signal from the noise-causing species does not substantially contribute to the total signal detected by an analyte sensor.

The term "copolymer" as used herein is a broad term, and is to be given its ordinary and customary meaning to a person of ordinary skill in the art (and is not to be limited to a special or customized meaning), and refers without limitation to polymers having two or more different repeat units and includes copolymers, terpolymers, tetrapolymers, and the like.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of one or more analytes. In one example, the sensing region generally comprises a working electrode (anode), a reference electrode (optionally remote from the sensing region), an insulator disposed therebetween, and a membrane affixed to the body and covering the electrochemically reactive surfaces of the working and optionally reference electrode.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In one embodiment, a working electrode measures hydrogen peroxide creating a measurable current.

The term "electrochemical cell" as used herein is a broad term, and is to be given its ordinary and customary meaning to a person of ordinary skill in the art (and is not to be limited to a special or customized meaning), and refers without limitation to a device in which chemical energy is converted to electrical energy.

The term "co-analyte" as used herein is a broad term, and is to be given its ordinary and customary meaning to a person of ordinary skill in the art (and is not to be limited to a special or customized meaning), and refers without limitation to a molecule required in an enzymatic reaction to react with the analyte and the enzyme to form the specific product being measured. In one exemplary embodiment of a glucose sensor, an enzyme, glucose oxidase (GOX) is provided to react with glucose and oxygen (the co-analyte) to form hydrogen peroxide.

The term "constant analyte" as used herein is a broad term, and is to be given its ordinary and customary meaning to a person of ordinary skill in the art (and is not to be limited to a special or customized meaning), and refers without limitation to an analyte wherein the concentration remains relatively constant over a time period, for example over an hour to a day as compared to other variable analytes. For example, in a person with diabetes, oxygen and urea may be relatively constant analytes in particular tissue compartments relative to glucose concentration, which can oscillate between about 40 mg/dL and about 400 mg/dL. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The term "proximal" as used herein is a broad term, and is to be given its ordinary and customary meaning to a person of ordinary skill in the art (and is not to be limited to a special or customized meaning), and refers without limitation to the property of being near to a point of reference such as an origin or a point of attachment. For example, in some embodiments of a membrane that covers an electrochemically reactive surface, an electrolyte domain is located more proximal to an electrochemically reactive surface than a resistance domain.

The term "distal" as used herein is a broad term, and is to be given its ordinary and customary meaning to a person of ordinary skill in the art (and is not to be limited to a special or customized meaning), and refers without limitation to the property of being spaced relatively far from a point of reference, such as an origin or a point of attachment. For example, in some embodiments of a membrane that covers an electrochemically reactive surface, a particle-containing domain is located more distal to an electrochemically reactive surface than an enzyme domain.

The terms "computer" and "computer system" as used herein are broad terms, and are to be given their ordinary and customary meanings to a person of ordinary skill in the art (and are not to be limited to a special or customized meaning), and refer without limitation to a machine that can be programmed to manipulate data.

The terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, and the like designed to perform arithmetic and logic operations using logic circuitry that responds to and processes the basic instructions that drive a computer.

The term "ROM" as used herein is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter" as used herein is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "RF transceiver" as used herein is a broad term, and is to be given its ordinary and customary meaning to a person of ordinary skill in the art (and is not to be limited to a special or customized meaning), and refers without limitation to a radio frequency transmitter and/or receiver for transmitting and/or receiving signals.

The terms "raw data stream" and "data stream" as used herein are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer. In some embodiments, raw data includes one or more values (e.g., digital value) representative of the current flow integrated over time (e.g., integrated value), for example, using a charge counting device, and/or the like.

The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "potentiostat" as used herein is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. Typically, the potentiostat forces whatever current is necessary to flow between the working and reference or counter electrodes to keep the desired potential, as long as the needed cell voltage and current do not exceed the compliance limits of the potentiostat.

The terms "operatively connected," "operably connected," "operatively linked" and "operably linked" as used herein are broad terms, and are to be given their ordinary and customary meaning to a person of ordinary skill in the art (and are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity. In some embodiments, these terms are broad enough to include transmission of energy from one component to another, such as but not limited to powering the component receiving the energy via inductive coupling.

The term "smoothing" and "filtering" as used herein are broad terms, and are to be given their ordinary and customary meaning to a person of ordinary skill in the art (and are not to be limited to a special or customized meaning), and refer without limitation to modification of a set of data to make it smoother and more continuous and remove or diminish outlying points, for example, by performing a moving average of the raw data stream.

The term "algorithm" as used herein is a broad term, and is to be given its ordinary and customary meaning to a person of ordinary skill in the art (and is not to be limited to a special or customized meaning), and refers without limitation to the computational processes (for example, programs) involved in transforming information from one state to another, for example using computer processing.

The term "regression" as used herein is a broad term, and is to be given its ordinary and customary meaning to a person of ordinary skill in the art (and is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "pulsed amperometric detection" as used herein is a broad term, and is to be given its ordinary and customary meaning to a person of ordinary skill in the art (and is not to be limited to a special or customized meaning), and refers without limitation to an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "calibration" as used herein is a broad term, and is to be given its ordinary and customary meaning to a person of ordinary skill in the art (and is not to be limited to a special or customized meaning), and refers without limitation to the relationship and/or the process of determining the relationship between sensor data and corresponding reference data, which may be used to convert sensor data into meaningful values substantially equivalent to the reference. In some embodiments, namely in continuous analyte sensors, calibration may be updated or recalibrated over time if changes in the relationship between the sensor and reference data occur, for example due to changes in sensitivity, baseline, transport, metabolism, and the like.

The term "sensor analyte values" and "sensor data" as used herein are broad terms, and are to be given their ordinary and customary meaning to a person of ordinary skill in the art (and are not to be limited to a special or customized meaning), and refer without limitation to data received from a continuous analyte sensor, including one or more time-spaced sensor data points.

The term "reference analyte values" and "reference data" as used herein are broad terms, and are to be given their ordinary and customary meaning to a person of ordinary skill in the art (and are not to be limited to a special or customized meaning), and refer without limitation to data from a reference analyte monitor, such as a blood glucose meter, and the like, including one or more reference data points. In some embodiments, the reference glucose values are obtained from a self-monitored blood glucose (SMBG) test (for example, from a finger or forearm blood test) or an YSI (Yellow Springs Instruments) test, for example.

The term "matched data pairs" as used herein is a broad term, and is to be given its ordinary and customary meaning to a person of ordinary skill in the art (and is not to be limited to a special or customized meaning), and refers without limitation to reference data (for example, one or more reference analyte data points) matched with substantially time corresponding sensor data (for example, one or more sensor data points).

The terms "noise-causing species" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor so as to produce a signal that does not accurately represent the analyte measurement. In one example of an electrochemical sensor, noise-causing species are compounds with an oxidation potential that overlaps with that of the analyte to be measured, and can produce a false positive signal. In another example of an electrochemical sensor, noise-causing species are substantially non-constant compounds (e.g., the concentration of an interfering species fluctuates over time). Noise-causing species can be separated into two classes, those that are internally derived and those that are externally derived. In general, internally derived noise-causing species are produced by the body as a result of daily metabolism, wound healing, a disease process and the like, and include but are not limited to compounds with electroactive acidic, amine or sulfhydryl groups, urea, lactic acid, phosphates, citrates, peroxides, amino acids, amino acid precursors or breakdown products, nitric oxide (NO), NO-donors, NO-precursors, bilirubin, cholesterol, creatinine, dopamine, and uric acid electroactive species produced during cell metabolism and/or wound healing, electroactive species that arise during body pH changes and the like. In general, externally derived noise-causing species are compounds taken into the body (e.g., by injection, ingestion, inhalation and the like) such as drugs and vitamins, and include but are not limited to compounds with electroactive acidic, amine or sulfhydryl groups, phosphates, citrates, peroxides, amino acids, acetaminophen, ascorbic acid, dopamine, ephedrine, ibuprofen, L-dopa, methyl dopa, salicylate, tetracycline, tolazamide, tolbutamide, triglycerides and the like. Electroactive species that cause constant and/or non-constant noise are included in the definitions of "noise-causing species" and "interfering species."

The term "conductive component" as used herein is a broad term, and is to be given its ordinary and customary meaning to a person of ordinary skill in the art (and is not to be limited to a special or customized meaning) and refers without limitation to materials that have a tendency to behave as an electrical conductor. In some embodiments, an electrical conductor contains movable charges (e.g., electrical charges), which can be forced to move when an electric potential is applied in accordance with Ohm's law. In some embodiments, the term refers to a sufficient amount of electrical conductance (e.g., material property) to provide a necessary function (electrical conduction). In some embodiments, a conductive component can electrochemically interact with another compound of opposite charge, such that the other compound is oxidized or reduced. In some embodiments, an electrical conductor facilitates a charge transfer (e.g., uses electrical energy) to initiate a chemical reaction at a catalyst.

The term "non-conductive component," as used herein is a broad term, and is to be given its ordinary and customary meaning to a person of ordinary skill in the art (and is not to be limited to a special or customized meaning) and refers without limitation to materials that have a tendency to act as an electrical insulator. In one exemplary embodiment, a non-conductive component can be placed between two electrically conductive materials, to prevent movement of electricity between the two electrically conductive materials. In some embodiments, the term refers to a sufficient amount of insulative property (e.g., of a material) to provide a necessary function (electrical insulation). The terms "electrical insulator," "insulator" and "non-conductive material" can be used interchangeably herein.

The terms "particulate" and "particle" as used herein are broad terms, and are to be given its ordinary and customary meaning to a person of ordinary skill in the art (and is not to be limited to a special or customized meaning), and refers without limitation to a particle of any shape or size. Particle size can be measured in angstroms (Å), nanometers (nm), microns (µm), and the like. In some embodiments, a plurality of particles can have a range of particle sizes. In some embodiments, particles can be characterized by an ability to pass through one or more defined mesh/screen sizes, by weight, and the like. As a non-limiting example, in some embodiments, the conductive component includes a plurality of particles, such as but not limited to conductive metal particles or conductive polymer particles. The particle-containing domain may comprise particulates that are physically separated, particulates that physically contact other particulates, or a combination of both.

The term "dispersion" as used herein is a broad term, and is to be given its ordinary and customary meaning to a person of ordinary skill in the art (and is not to be limited to a special or customized meaning), and refers without limitation to a stable or unstable chemical system of fine particles distributed in a medium (e.g., gas, liquid, or colloid). For example, in some embodiments, dispersion comprises a plurality of fine particles formed of a conductive material, which are distributed in a non-conductive material, such as but not limited to a polymer.

The term "coaxial" as used herein is a broad term, and is to be given its ordinary and customary meaning to a person of ordinary skill in the art (and is not to be limited to a special or customized meaning), and refers without limitation to having a common axis, having coincident axes or mounted on concentric shafts.

The term "coplanar" as used herein is a broad term, and is to be given its ordinary and customary meaning to a person of ordinary skill in the art (and is not to be limited to a special or customized meaning), and refers without limitation to lying in the same plane.

The term "in vivo portion" as used herein is a broad term, and is to be given its ordinary and customary meaning to a person of ordinary skill in the art (and is not to be limited to a special or customized meaning), and refers without limitation to a portion of a device that is to be implanted or inserted into the host. In one exemplary embodiment, an in vivo portion of a transcutaneous sensor is a portion of the sensor that is inserted through the host's skin and resides within the host.

The term "sensor break-in" as used herein is a broad term, and is to be given its ordinary and customary meaning to a person of ordinary skill in the art (and is not to be limited to a special or customized meaning), and refers without limitation to the time required for the sensor's output signal to provide a substantially linear response to the analyte concentration (e.g., glucose level). In some embodiments, sensor break-in can include electrochemical break-in and/or membrane break-in.

The term "membrane break-in" as used herein is a broad term, and is to be given its ordinary and customary meaning to a person of ordinary skill in the art (and is not to be limited to a special or customized meaning), and refers without limitation to a time necessary for the membrane to equilibrate to its surrounding environment (e.g., physiological environment in vivo).

The term "electrochemical break-in" as used herein is a broad term, and is to be given its ordinary and customary meaning to a person of ordinary skill in the art (and is not to be limited to a special or customized meaning), and refers without limitation to a time, after sensor insertion in vitro and/or in vivo, at which the current output from the sensor settles to a stable function (e.g., a linear response) following the application of the potential to the sensor. Numerous methods of accelerating electrochemical break-in can be used, such as, but not limited to, configuring the sensor electronics to aid in decreasing the break-in time of the sensor by applying different voltage settings (for example, starting with a higher voltage setting and then reducing the voltage setting). Additional methods of accelerating sensor break-in time are described in U.S. Pat. No. 5,411,647, for example, which is incorporated herein by reference in its entirety.

The term "noise" as used herein is a broad term, and is to be given its ordinary and customary meaning to a person of ordinary skill in the art (and is not to be limited to a special or customized meaning), and refers without limitation to a component of an analyte sensor signal that is not related to the analyte concentration. In one example of a glucose sensor, the noise is composed substantially of signal contribution due to factors other than glucose (for example, noise-causing species, non-reaction-related hydrogen peroxide, or other electroactive species with an oxidation potential that overlaps with that of hydrogen peroxide). In general, noise comprises components related to constant and non-constant factors (e.g., constant noise and non-constant noise), including endogenous and exogenous interfering species.

The terms "constant noise" and "constant background" as used herein are broad terms, and are to be given their ordinary and customary meaning to a person of ordinary skill in the art (and is not to be limited to a special or customized meaning), and refer without limitation to the component of the noise signal that remains relatively constant over time. In some embodiments, constant noise may be referred to as "background" or "baseline." For example, certain electroactive compounds found in the human body are relatively constant factors (e.g., baseline of the host's physiology). In some circumstances, constant background noise can slowly drift over time (e.g., increase or decrease), however this drift need not adversely affect the accuracy of a sensor, for example, because a sensor can be calibrated and re-calibrated and/or the drift measured and compensated for.

The terms "non-constant noise" and "non-constant background" as used herein are broad terms, and are to be given their ordinary and customary meaning to a person of ordinary skill in the art (and is not to be limited to a special or customized meaning), and refer without limitation to a component of the background signal that is relatively non-constant, for example, transient and/or intermittent. For example, certain electroactive compounds, are relatively non-constant (e.g., intermittent interferents due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The term "GOX" as used herein is a broad term, and is to be given its ordinary and customary meaning to a person of ordinary skill in the art (and is not to be limited to a special or customized meaning), and refers without limitation to the enzyme Glucose Oxidase (e.g., GOX or GOx is an abbreviation/acronym).

The term "mechanism" as used herein is a broad term, and is to be given its ordinary and customary meaning to a person of ordinary skill in the art (and is not to be limited to a special or customized meaning), and refers without limitation to a process, technique, or system for achieving a result. The term is not limited by the processes, techniques or systems described herein, but also includes any process, technique, or system that can achieve a stated result.

The term "redox" as used herein is a broad term, and is to be given its ordinary and customary meaning to a person of ordinary skill in the art (and is not to be limited to a special or customized meaning), and refers without limitation to "oxidation/reduction," which describes all chemical reactions in which atoms have their oxidation number (oxidation state) changed. The term "oxidation" describes the loss of electrons by a molecule, atom or ion. In contrast, the term "reduction" describes the gain of electrons by a molecule, atom or ion. For example, hydrogen peroxide reduces to hydroxide in the presence of an acid:

$$H_2O_2 + 2e^- \rightarrow 2OH^-$$

The term "redox potential" as used herein is a broad term, and is to be given its ordinary and customary meaning to a person of ordinary skill in the art (and is not to be limited to a special or customized meaning), and refers without limitation to the tendency of a chemical species to acquire electrons and thereby be reduced. Each species has its own intrinsic reduction potential, the more positive the potential, the greater the species' affinity for electrons and tendency to be reduced.

The term "hydrophilic" as used herein is a broad term, and is to be given its ordinary and customary meaning to a person of ordinary skill in the art (and is not to be limited to a special or customized meaning), and refers without limitation to the property of having affinity for water. For example, a hydrophilic polymer (e.g., having a hydrophilic component) is primarily soluble in water or has a tendency to absorb water. In general, the more hydrophilic a polymer is, the more that polymer tends to dissolve in, mix with, or be wetted by water. In one exemplary embodiment, the hydrophilic component of a hydrophilic polymer promotes the movement of water (e.g., by diffusion or other means) through a membrane formed of the hydrophilic polymer, such as by lowering the thermodynamic barrier to movement of water through the membrane. In some embodiments, a hydrophilic polymer includes a hydrophilic-hydrophobic or hydrophobic-hydrophilic polymer.

The terms "hydrophilic-hydrophobic" and "hydrophobic-hydrophilic" as used herein are broad terms, and are to be given their ordinary and customary meaning to a person of ordinary skill in the art (and are not to be limited to a special or customized meaning), and refer without limitation to the property of having both hydrophilic and hydrophobic substituents and/or characteristics, such as, for example, a polymer. The terms hydrophilic-hydrophobic and hydrophobic-hydrophilic are used interchangeably herein, and are not meant to imply if either the hydrophilic or the hydrophobic substituents are the major component of the polymer.

The term "hydrophobic" as used herein is a broad term, and is to be given its ordinary and customary meaning to a person of ordinary skill in the art (and is not to be limited to a special or customized meaning), and refers without limitation to the property of lacking affinity for, or even repelling, water. For example, the more hydrophobic a polymer, the more that polymer tends to not dissolve in, not mix with, or not be wetted by water. Hydrophilicity and hydrophobicity can be spoken of in relative terms, such as but not limited to a spectrum of hydrophilicity/hydrophobicity within a group of compounds. In some embodiments wherein two or more polymers are being discussed, the term "hydrophobic polymer" can be defined based on the polymer's relative hydrophobicity when compared to another, more hydrophilic polymer. In some embodiments, a hydrophobic polymer includes a hydrophobic-hydrophilic or a hydrophilic-hydrophobic polymer.

The term "clinical acceptability" as used herein is a broad term, and is to be given its ordinary and customary meaning to a person of ordinary skill in the art (and is not to be limited to a special or customized meaning), and refers without limitation to determination of the risk of an inaccuracy to a patient. Clinical acceptability considers a deviation between time corresponding analyte measurements (for example, data from a glucose sensor and data from a reference glucose monitor) and the risk (for example, to the decision making of a person with diabetes) associated with that deviation based on the analyte value indicated by the sensor and/or reference data. An example of clinical acceptability can be 85% of a given set of measured analyte values within the "A" and "B" region of a standard Clarke Error Grid when the sensor measurements are compared to a standard reference measurement.

The term "comprising" as used herein is synonymous with "including," "containing," or "characterized by," and is inclusive or open-ended and does not exclude additional, unrecited elements or method steps.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, a membrane interference domain of some embodiments is configured to resist a sufficient amount of interfering species such that tracking of analyte levels (e.g., glucose levels) can be achieved, which may include an amount greater than 50 percent, an amount greater than 60 percent, an amount greater than 70 percent, an amount greater than 80 percent, and an amount greater than 90 percent of interfering species. In some preferred embodiments, the phrase "substantially accurate" means that the calibrated analyte level is sufficiently accurate to be displayed to the host, for example, due to its clinical acceptability or statistical accuracy. For example, the data meet the ±20% accuracy standard (e.g., wherein the data are compared to a "gold standard" for glucose measurement, such as a YSI glucose analyzer) for blood glucose meters (BGM) established by the U.S. Food and Drug Administration (FDA).

Overview

The following description and examples describe in detail some exemplary embodiments of devices and methods for providing continuous measurement of an analyte concentration, including a sensor having a membrane domain configured to oxidize and/or reduce noise-causing species. It is to be understood that there are numerous variations and modifications of the devices and methods described herein that are encompassed by the present invention. Accordingly, the description of a certain exemplary embodiment should not be deemed to limit the scope of the present invention.

Although the description that follows is primarily directed at glucose monitoring devices, these sensor configurations are not limited to use in devices that measure or monitor glucose in a biological fluid. Rather, these sensor configurations can be applied to a variety of devices, including for example, those that detect and quantify other analytes present in biological samples (including, but not limited to, cholesterol, amino acids lactate, calcium, pH, sodium, potassium, oxygen, carbon dioxide/bicarbonate, blood nitrogen urea (BUN), creatinine, albumin, total protein, alkaline phosphatase, alanine amino transferase, aspartate amino transferase, bilirubin, and/or hematocrit), especially those analytes that are substrates for oxidase enzymes (see, e.g., U.S. Pat. No. 4,703,756).

Noise

Generally, implantable sensors measure a signal related to an analyte of interest in a host. For example, an electrochemical sensor can measure at least one of glucose, calcium, pH, sodium, potassium, oxygen, carbon dioxide/bicarbonate, blood nitrogen urea (BUN), creatinine, albumin, total protein, alkaline phosphatase, alanine amino transferase, aspartate amino transferase, bilirubin, and/or hematocrit in a host, such as an animal (e.g., a human). Generally, the signal is converted mathematically to a numeric value indicative of analyte status, such as analyte concentration. The signal detected by the sensor can be broken down into its component parts. For example, in an enzymatic electrochemical analyte sensor, after sensor break-in is complete, the total signal can be divided into an "analyte component," which is representative of analyte (e.g., glucose, calcium, pH, sodium, potassium, oxygen, carbon dioxide/bicarbonate, blood nitrogen urea (BUN), creatinine, albumin, total protein, alkaline phosphatase, alanine amino transferase, aspartate amino transferase, bilirubin, and/or hematocrit) concentration, and a "noise component," which is caused by non-analyte-related species that have a redox potential that substantially overlaps with the redox potential of the analyte (or measured species, e.g., $H_2O_2$) at an applied voltage. The noise component can be further divided into its component parts, e.g., constant and non-constant noise. It is not unusual for a sensor to experience a certain level of noise. In general, "constant noise" (also referred to as constant background or baseline) is caused by non-analyte-related factors that are relatively stable over time, including but not limited to electroactive species that arise from generally constant (e.g., daily) metabolic processes. Constant noise can vary widely between hosts. In contrast, "non-constant noise" (also referred to as non-constant background) is caused by non-constant, non-analyte-related species (e.g., non-constant noise-causing electroactive species) that arise during transient events, such as during host metabolic processes (e.g., wound healing or in response to an illness), or due to ingestion of certain compounds (e.g., certain drugs). In some circumstances, noise can be caused by a variety and/or plurality of noise-causing electroactive species.

FIG. 1 is an exemplary graph illustrating the components of a signal measured by a glucose sensor (after sensor break-in was complete) in a non-diabetic volunteer host. The X-axis indicates time. The Y-axis indicates the signal amplitude (in counts) detected by the sensor. The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The total signal collected by the sensor is represented by line 1000, which includes components related to glucose, constant noise, and non-constant noise, which are described in more detail elsewhere herein. In some embodiments, the total signal is a raw data stream, which can include an averaged or integrated signal, for example, by using a charge-counting device.

The non-constant noise component of the total signal is represented by line 1010. The non-constant noise component 1010 of the total signal 1000 can be obtained by filtering the total signal 1000 to obtain a filtered signal 1020 using any of a variety of known filtering techniques, and then subtracting the filtered signal 1020 from the total signal 1000. In some embodiments, the total signal can be filtered using linear regression analysis of the n (e.g., 10) most recent sampled sensor values. In some embodiments, the total signal can be filtered using non-linear regression. In some embodiments, the total signal can be filtered using a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set) and then regresses the remaining measurements to estimate the glucose value. In some embodiments, the total signal can be filtered using a non-recursive filter, such as a finite impulse response (FIR) filter. An FIR filter is a digital signal filter, in which every sample of output is the weighted sum of past and current samples of input, using only some finite number of past samples. In some embodiments, the total signal can be filtered using a recursive filter, such as an infinite impulse response (IIR) filter. An IR filter is a type of digital signal filter, in which every sample of output is the weighted sum of past samples of input and output and current samples of input. In some embodiments, the total signal can be filtered using a maximum-average (max-average) filtering algorithm, which smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes. To overcome these downward trending signal artifacts, the max-average calculation tracks with the highest sensor values, and discards the bulk of the lower values. Additionally, the max-average method is designed to reduce the contamination of the data with unphysiologically high data from the high spikes. The max-average calculation smoothes data at a sampling interval (e.g., every 30 seconds) for transmission to the receiver at a less frequent transmission interval (e.g., every 5 minutes), to minimize the effects of low non-physiological data. First, the microprocessor finds and stores a maximum sensor counts value in a first set of sampled data points (e.g., 5 consecutive, accepted, thirty-second data points). A frame shift time window finds a maximum sensor counts value for each set of sampled data (e.g., each 5-point cycle length) and stores each maximum value. The microprocessor then computes a rolling average (e.g., 5-point average) of these maxima for each sampling interval (e.g., every 30 seconds) and stores these data. Periodically (e.g., every $10^{th}$ interval), the sensor outputs to the receiver the current maximum of the rolling average (e.g., over the last 10 thirty-second intervals as a smoothed value for that time period (e.g., 5 minutes)). In some embodiments, the total signal can be filtered using a "Cone of Possibility Replacement Method," which utilizes physiological information along with glucose signal values in order to define a "cone" of physiologically feasible glucose signal values within a human. Particularly, physiological information depends upon the physiological parameters obtained from continuous studies in the literature as well as our own observations. For example, in some embodiments of a glucose sensor, a first physiological parameter uses a maximal sustained rate of change of glucose in humans (e.g., about 4 to 5 mg/dL/min) and a maximum sustained acceleration of that rate of change (e.g., about 0.1 to 0.2 mg/min/min). A second physiological parameter uses the knowledge that rate of change of glucose is lowest at the maxima and minima, which are the areas of greatest risk in patient treatment. A third physiological parameter uses the fact that the best solution for the shape of the curve at any point along the curve over a certain time period (e.g., about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate change can be lower when the subject is lying down or sleeping; on the other hand, the maximum per minute rate change can be higher when the subject is exercising, for example. In some embodiments, the total signal can be filtered using reference changes in electrode potential to estimate glucose sensor data during positive detection of signal artifacts from an electrochemical glucose sensor, the method hereinafter referred to as reference drift replacement. In these embodiments, the electrochemical glucose sensor comprises working, counter, and reference electrodes. This method exploits the function of the reference electrode as it drifts to compensate for counter electrode limitations during oxygen deficits, pH changes, and/or temperature changes. In alternative implementations of the reference drift method, a variety of algorithms can therefore be implemented based on the changes measured in the reference electrode. Linear algorithms, and the like, are suitable for interpreting the direct relationship between reference electrode drift and the non-glucose rate limiting signal noise such that appropriate conversion to signal noise compensation can be derived. Additional descriptions of signal filtering can be found in U.S. Patent Application Publication No. US-2005-0043598-A1 and U.S. Patent Application Publication No. US-2007-0235331-A1, each of which is incorporated herein by reference in its entirety.

Referring again to FIG. 1, in some embodiments, the constant noise signal component 1030 can be obtained by calibrating the sensor signal using reference data, such as one or more blood glucose values obtained from a hand-held blood glucose meter, from which the baseline "b" of a regression can be obtained, representing the constant noise signal component 1030. In some embodiments, noise is also baseline. Other methods for calibrating the signal include those described in U.S. Patent Application Publication No. US-2005-0027463-A1, U.S. Patent Application Publication No. US-2005-0187720-A1, U.S. Patent Application Publication No. US-2005-0021666-A1, U.S. Patent Application Publication No. US-2005-0027180-A1, U.S. Patent Application Publication No. US-2005-0203360-A1, U.S. Patent Application Publication No. US-2005-0043598-A1, U.S. Patent Application Publication No. US-2007-0032706-A1, U.S. Patent Application Publication No. US-2007-0016381-A1, U.S. Patent Application Publication No. US-2008-0033254-A1, U.S. Patent Application Publication No. US-2005-0143635-A1, U.S. Patent Application Publication No. US-2007-0027385-A1, U.S. Patent Application Publication No. US-2007-0213611-A1, U.S. Patent Application Publication No. US-2008-0083617-A1, U.S. Patent Application Publication No. US-2006-0020187-A1, U.S. Patent Application Publication No. US-2006-0270923-A1, U.S. Patent Application Publication No. US-2007-0027370-A1, U.S. Patent Application Publication No. US-2006-0258929-A1, U.S. Patent Application Publication No. US-2008-0119703-A1, U.S. Patent Application Publication No. US-2008-0108942-A1, U.S. Patent Application Publication No. US-2007-0235331-A1, U.S. Patent Application Publication No. US-2008-0194936-A1, U.S. Patent Application Publication No. US-2008-0183061-A1, U.S. Patent Application Publication No. US-2008-0200789-A1, U.S. Patent Application Publication No. 2009-0192366-A1, U.S. Patent Application Publication No. 2009-0192722-A1, and U.S. Patent Application Publication No. 2009-0156924-A1, each of which is incorporated herein by reference in its entirety.

In this embodiment, the analyte signal component 1040 was obtained by subtracting the constant noise signal component 1030 from the filtered signal 1020.

Noise is clinically important because it can induce error and can reduce sensor performance, such as by providing a signal that causes the analyte concentration to appear higher or lower than the actual analyte concentration. For example, upward or high noise (e.g., noise that causes the signal to increase) can cause the host's glucose concentration to appear higher than it truly is, which can lead to improper treatment decisions. Similarly, downward or low noise (e.g., noise that causes the signal to decrease) can cause the host's glucose concentration to appear lower than it is, which can also lead to improper treatment decisions. Accordingly, noise reduction is desirable.

Noise can be caused by a variety of factors, ranging from mechanical factors to biological factors. For example, it is known that macro- or micro-motion, ischemia, pH changes, temperature changes, pressure, stress, or even unknown mechanical, electrical, and/or biochemical sources can cause noise, in some embodiments. Noise-causing species, which are known to cause non-constant noise, can be compounds, such as drugs that have been administered to the host (e.g., externally derived), or intermittently produced products (e.g., internally derived) of various host metabolic processes. Exemplary noise-causing species include but are not limited to a variety of drugs (e.g., acetaminophen), $H_2O_2$ from exterior sources (e.g., produced outside the sensor membrane), and reactive metabolic species (e.g., reactive oxygen and nitrogen species, some hormones, etc.). Some known noise-causing species for a glucose sensor include but are not limited to acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. In some embodiments, the membrane includes a particle-containing domain located more distal to the electroactive surface than the enzyme and configured to electrochemically oxidize or electrochemically reduce noise-causing species, such as but not limited to noise causing species having an electrical potential that substantially overlaps with that of the measured compound (e.g., $H_2O_2$).

In some experiments of implantable glucose sensors, it was observed that noise increased when some hosts were intermittently sedentary, such as during sleep or sitting for extended periods. When the host began moving again, the noise quickly dissipated. Noise that occurs during intermittent, sedentary periods (also referred to as intermittent sedentary noise) can occur during relatively inactive periods, such as sleeping. Non-constant, non-analyte-related factors can cause intermittent sedentary noise, such as was observed in one exemplary study of non-diabetic individuals implanted with enzymatic-type glucose sensors built without enzyme. These sensors (without enzyme) could not react with or measure glucose and therefore provided a signal due to non-glucose effects only (e.g., constant and non-constant noise). During sedentary periods (e.g., during sleep), extensive, sustained signal was observed on the sensors. Then, when the host got up and moved around, the signal rapidly corrected. As a control, in vitro experiments were conducted to determine if a sensor component might have leached into the area surrounding the sensor and caused the noise, but none was detected. From these results, it is believed that a host-produced non-analyte related reactant was diffusing to the electrodes and producing the unexpected non-constant noise signal.

While not wishing to be bound by theory, it is believed that a concentration increase of noise-causing electroactive species, such as electroactive metabolites from cellular metabolism and wound healing, can interfere with sensor function and increase the level of noise observed during host sedentary periods. For example, local lymph pooling, which can occur when a part of the body is compressed or when the body is inactive, can cause, in part, this local build up of interferents (e.g., electroactive metabolites). Similarly, a local accumulation of wound healing metabolic products (e.g., at the site of sensor insertion) tends to increase the level of noise on the sensor. Noise-causing electroactive species can include, but are not limited to, compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example. For a more complete discussion of noise and its sources, see U.S. Patent Application Publication No. US-2007-0027370-A1, which is incorporated herein by reference in its entirety.

Noise can be recognized and/or analyzed in a variety of ways. For example, in some circumstances, non-constant noise changes faster than the analyte signal and/or does not follow an expected analyte signal pattern; and lasts for a period of about 10 hours or more, 8 hours, 6 hours, 4 hours, 2 hours, 60 minutes, 30 minutes, or 10 minutes or less. In some embodiments, the sensor data stream can be monitored, signal artifacts detected, and data processing performed based at least in part on whether or not a signal artifact has been detected, such as described in U.S. Patent Application Publication No. US-2005-0043598-A1, which is incorporated herein by reference in its entirety. Additional discussion of noise recognition and analysis can also be found in U.S. Patent Application Publication No. US-2007-0032706-A1, which is incorporated herein by reference in its entirety.

A signal component's percentage of the total signal can be determined using a variety of methods of quantifying an amplitude of signal components and total signal, from each components percent contribution can be calculated. In some embodiments, the signal component(s) can be quantified by comparing the peak-to-peak amplitudes of each signal component for a time period, whereby the peak-to-peak amplitudes of each component can be compared to the peak-to-peak amplitude of the total signal to determine it's percentage of the total signal. In some embodiments, the signal component(s) can be quantified by determining the Root Mean Square (RMS) of the signal component for a time period. In one exemplary of Root Mean Square analysis of signal components, the signal component(s) can be quantified using the formula:

$$RMS = \sqrt{\frac{\sum (x_1^2 + x_2^2 + x_3^2 + x_n^2)}{n}}$$

wherein there are a number (n) of data values (x) for a signal (e.g., analyte component, non-constant noise component, constant noise component, and/or total signal) during a predetermined time period (e.g., about 1 day, about 2 days, about 3 days, etc). Once the signal components and/or total signal are quantified, the signal components can be compared to the total signal to determine a percentage of each signal component within the total signal.

In some conventional analyte sensors, non-constant noise can be a significant component of the total signal, such as 30%, 40%, 50%, 60% or more of the total signal. Additionally, non-constant noise can occur for durations of minutes or hours, in some circumstances. In some circumstances, non-constant noise can be equivalent to an analyte signal associated with a glucose concentration of about 400 mg/dL or more. Noise can induce error in the sensor reading, which can reduce sensor accuracy and clinically useful data. However, a high level of sensor accuracy is critical for successful patient care and desirable clinical outcomes. In some embodiments, as described in greater detail elsewhere herein, the particle-containing domain, such as an electrode and/or membrane domain, is formed of conductive particles dispersed in a non-conductive polymer or polymer blend, such that the negative effects of noise are substantially reduced and clinically useful data are provided to the user.

Analyte Sensors

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, intravascular, or extracorporeal device. In some embodiments, the analyte sensor may analyze a plurality of intermittent biological samples. The analyte sensor may use any method for analyte-measurement, including enzymatic, chemical, physical, electrochemical, spectrophotometric, polarimetric, calorimetric, radiometric, and the like.

In general, electrochemical analyte sensors provide at least one working electrode and at least one reference electrode, which are configured to measure a signal associated with a concentration of the analyte in the host, such as described in more detail below. The output signal is typically a raw data stream that is used to provide a useful value of the measured analyte concentration in a host to the patient or doctor, for example.

In general, continuous analyte sensors define a relationship between sensor-generated measurements (for example, current in pA, nA, or digital counts after A/D conversion)

and a reference measurement (for example, glucose concentration mg/dL or mmol/L) that are meaningful to a user (for example, patient or doctor). In the case of an implantable diffusion-based glucose oxidase electrochemical glucose sensor, the sensing mechanism generally depends on phenomena that are linear with glucose concentration, for example: (1) diffusion of glucose through a membrane (e.g., biointerface membrane) situated between implantation site and/or the electrode surface, (2) an enzymatic reaction within the membrane, and (3) diffusion of the $H_2O_2$ to the sensor. Because of this linearity, calibration of the sensor can be understood by solving an equation:

$$y=mx+b$$

wherein y represents the sensor signal (e.g., counts), x represents the estimated glucose concentration (e.g., mg/dL), m represents the sensor sensitivity to glucose (e.g., counts/mg/dL), and b represents the baseline signal (e.g., counts). When both sensitivity m and baseline (background) b change over time in vivo, calibration has generally requires at least two independent, matched data pairs ($x_1$, $y_1$; $x_2$, $y_2$) to solve for m and b and thus allow glucose estimation when only the sensor signal, y, is available. Matched data pairs can be created by matching reference data (for example, one or more reference glucose data points from a blood glucose meter, and the like) with substantially time corresponding sensor data (for example, one or more glucose sensor data points) to provide one or more matched data pairs, such as described in co-pending U.S. Patent Application Publication No. US-2005-0027463-A1, which is incorporated herein by reference in its entirety. In some implantable glucose sensors, such as described in more detail in U.S. Pat. No. 6,329,161 to Heller et al., the sensing layer utilizes immobilized mediators (e.g., redox compounds) to electrically connect the enzyme to the working electrode, rather than using a diffusional mediator. In some implantable glucose sensors, such as described in more detail in U.S. Pat. No. 4,703,756, the system has two oxygen sensors situated in an oxygen-permeable housing, one sensor being unaltered and the other contacting glucose oxidase allowing for differential measurement of oxygen content in bodily fluids or tissues indicative of glucose levels. A variety of systems and methods of measuring glucose in a host are known, all of which may benefit from some of all of the preferred embodiments to provide a sensor having a signal that is not substantially affected by non-constant noise.

Additional description of analyte sensor configurations can be found in U.S. Patent Application Publication No. US-2008-0083617-A1, U.S. Patent Application Publication No. US-2007-0213611-A1, U.S. Patent Application Publication No. US-2007-0027385-A1, and U.S. Patent Application Publication No. US-2005-0143635-A1, each of which is incorporated herein by reference in its entirety.

Sensor Components Overview

In some embodiments, an analyte sensor includes a sensing mechanism 34 with a small structure (e.g., small-structured, micro- or small diameter sensor), for example, a needle-type sensor, in at least a portion thereof (see FIG. 2). As used herein the term "small-structured" preferably refers to an architecture with at least one dimension less than about 1 mm. The small structured sensing mechanism can be wire-based, substrate based, or any other architecture. In some alternative embodiments, the term "small-structured" can also refer to slightly larger structures, such as those having their smallest dimension being greater than about 1 mm, however, the architecture (e.g., mass or size) is designed to minimize the foreign body response (FBR) due to size and/or mass. In some embodiments, a biointerface membrane (e.g., membrane or sensing membrane) is formed onto the sensing mechanism 34 as described in more detail below. In some alternative embodiments, the sensor is configured to be wholly implanted in a host, such as in the host abdomen; such is described in U.S. Patent Application Publication No. US-2006-0020187-A1. In still other embodiments, the sensor is configured to be implanted in a host vessel or extracorporeally, such as is described in U.S. Patent Application Publication No. US-2007-0027385-A1, U.S. Patent Application Publication No. US-2008-0108942-A1, and U.S. Patent Application Publication No. US-2007-0197890-A1, and U.S. Patent Application Publication No. US-2008-0119703-A1, each of which is incorporated herein by reference in its entirety.

In the illustrated embodiments, the sensor is an enzyme-based electrochemical sensor, wherein the working electrode 38 measures the hydrogen peroxide ($H_2O_2$) produced by the enzyme catalyzed reaction of glucose being detected and creates a measurable electronic current (for example, detection of glucose utilizing glucose oxidase produces hydrogen peroxide as a by-product, $H_2O_2$ reacts with the surface of the working electrode producing two protons ($2H^+$), two electrons ($2e^-$) and one molecule of oxygen ($O_2$) which produces the electronic current being detected), such as described in more detail herein. Preferably, one or more potentiostat(s) is employed to monitor the electrochemical reaction at the electroactive surface of the working electrode(s). The potentiostat applies a potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrode. The output signal is typically a raw data stream that is used to provide a useful value of the measured analyte concentration in a host to the host or doctor, for example. In some alternative embodiments, the sensing mechanism includes electrodes deposited on a planar substrate, wherein the thickness of the implantable portion is less than about 1 mm. See, for example, U.S. Pat. Nos. 6,175,752 and 5,779,665.

Some alternative analyte sensors that can benefit from the systems and methods of some embodiments include U.S. Pat. Nos. 5,711,861, 6,642,015, 6,654,625, 6,565,509, 6,514,718, 6,465,066, 6,214,185, 5,310,469, 5,683,562, 6,579,690, 6,484,046, 6,512,939, and 6,424,847, for example. These patents are not inclusive of all applicable analyte sensors; in general, it should be understood that the disclosed embodiments are applicable to a variety of analyte sensor configurations.

Any of a variety of electrodes and/or electrode configurations can be employed for the analyte sensor. FIG. 2 is a perspective view of the in vivo portion of an exemplary embodiment of a continuous analyte sensor 34, also referred to as a transcutaneous analyte sensor, or needle-type sensor, particularly illustrating the sensing mechanism. Preferably, the sensing mechanism comprises a small structure as defined herein and is adapted for insertion under the host's skin, and the remaining body of the sensor (e.g., electronics, etc.) can reside ex vivo. In other embodiments (not shown), the analyte sensor is configured for exposure to the host's circulatory system, extracorporeal and/or wholly implantable. In the illustrated embodiment, the analyte sensor 34 includes two electrodes, i.e., a working electrode 38 and at least one additional electrode 30, which may function as a counter and/or reference electrode, hereinafter referred to as the reference electrode 30.

In some exemplary embodiments, each electrode is formed from a fine wire with a diameter of from about 0.001 or less to about 0.01 inches or more, for example, and is formed from, e.g., a plated insulator, a plated wire, or bulk electrically conductive material. Although the illustrated electrode configuration and associated text describe one preferred method for forming a transcutaneous sensor, a variety of known transcutaneous sensor configurations can be employed with the transcutaneous analyte sensor system of some embodiments, such as are described in U.S. Pat. No. 6,695,860 to Ward et al., U.S. Pat. No. 6,565,509 to Say et al., U.S. Pat. No. 6,248,067 to Causey III et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, and the like. Although the electrodes can by formed by a variety of manufacturing techniques (bulk metal processing, deposition of metal onto a substrate, and the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination. In some circumstances, as discussed elsewhere herein, and electrode can be formed of a plurality of conductive particles distributed throughout a non-conductive component, such as but not limited to a polymer or a polymer blend. Such "particulate electrodes" have the advantage of reduced material costs, moldability/conformability, and material properties, such as strength and fatigue resistance due to the non-conductive (e.g., polymer) component.

The working electrode 38 is configured to measure the concentration of an analyte, such as but not limited to glucose, uric acid, cholesterol, lactate and the like. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase (GOX) produces hydrogen peroxide as a byproduct, $H_2O_2$ reacts with the surface of the working electrode producing two protons (2H+), two electrons ($2e^-$) and one molecule of oxygen ($O_2$), which produces the electronic current being detected.

The working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, and the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

Preferably, the reference electrode 30, which may function as a reference electrode alone, or as a dual reference and counter electrode, is formed from silver, silver/silver chloride and the like. Preferably, the electrodes are juxtapositioned and/or twisted (e.g., coaxial) with or around each other; however other configurations are also possible. In one example, the reference electrode 30 is helically wound around the working electrode 38 as illustrated in FIG. 2. The assembly of wires may then be optionally coated together with an insulating material, similar to that described above, in order to provide an insulating attachment (e.g., securing together of the working and reference electrodes). Additional description of sensor electrodes can be found in U.S. Patent Application Publication No. US-2006-0015024-A1 and U.S. Patent Application Publication No. US-2006-0020187-A1, each of which is incorporated herein by reference in its entirety.

In some embodiments, a radial window is formed through the insulating material to expose a circumferential electroactive surface of the working electrode, using known methods. Additionally, sections of electroactive surface of the reference electrode are exposed. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). For example, in some embodiments, the sensor includes a first working electrode, which is configured to detect a signal comprising analyte-related signal and non-analyte related signal (e.g., noise-causing species) components, and a second working electrode, which is configured to detect only the non-analyte related signal component, wherein the signal detected via the second working electrode can be used to determine the component of the total signal related to only the analyte. In other embodiments, the sensor is configured and arranged to detect two or more analytes, and can include two or more working electrodes (e.g., a glucose-detecting working electrode and a potassium-detecting working electrode), a reference electrode and/or a counter electrode, for example, U.S. Pat. Nos. 7,081,195, 7,366,556 and 7,310,544, U.S. Patent Application Publication No. US-2005-0143635-A1, U.S. Patent Application Publication No. US-2007-0027385-A1, U.S. Patent Application Publication No. US-2007-0027385-A1, U.S. Patent Application Publication No. US-2007-0027284-A1, U.S. Patent Application Publication No. US-2008-0086042-A1, U.S. Patent Application Publication No. US-2008-0119703-A1, U.S. Patent Application Publication No. US-2007-0235331-A1, and U.S. Patent Application Publication No. US-2009-0018424-A1 each of which is incorporated by reference herein in its entirety, describe some systems and methods for implementing and using additional working, counter, and/or reference electrodes.

In some embodiments, the sensing region may include reference and/or other electrodes associated with the glucose-measuring working electrode and/or separate reference and/or counter electrodes associated with optional auxiliary working electrode(s). In yet another embodiment, the sensing region may include a glucose-measuring working electrode, an auxiliary working electrode, two counter electrodes (one for each working electrode), and one shared reference electrode. In yet another embodiment, the sensing region may include a glucose-measuring working electrode, an auxiliary working electrode, two reference electrodes, and one shared counter electrode. However, a variety of electrode materials and configurations can be used with the implantable analyte sensor of the preferred embodiments.

In general, a membrane 32 is disposed over the sensor's electrodes and provides one or more of the following functions: 1) protection of the exposed electrode surface from the biological environment (e.g., cell impermeable domain); 2) diffusion resistance (limitation) of the analyte (e.g., resistance domain); 3) a catalyst for enabling an enzymatic reaction (e.g., enzyme domain); 4) limitation or blocking of interfering species (e.g., particle-containing domain and optional interference domain); and/or 5) hydrophilicity at the electrochemically reactive surfaces of the sensor interface (e.g., electrolyte domain). However, it is understood that a sensing membrane modified for other sensors, for example, by including fewer or additional domains is within the scope of some embodiments. The membrane can be located over the sensor body by mechanical or chemical methods such as described in U.S. Patent Application Publication Nos. 2006/0015020 and 2005/0245799, each of which is incorporated herein by reference in their entirety. Additional description of the membrane 32 can be found in U.S. Patent Application Publication No. US-2005-0245799-A1 and U.S. Patent Application Publication No. US-2005-0242479-A1 (which describes biointerface and sensing membrane configurations and materials that may be applied to some embodiments), each of which is incorporated herein by reference in its entirety.

FIG. 3 is a cross-sectional view through the sensor of FIG. 2 on line 3-3, illustrating the membrane 32 in one embodiment. In this embodiment, the membrane includes an electrode domain 43, an interference domain 44, and enzyme domain 46, a diffusion resistance domain 48, and a particle-containing domain 50 wrapped around the platinum wire working electrode 38. In some embodiments, this membrane can include additional domains, as described herein. In some embodiments, the transcutaneous wire sensor is configured for short-term implantation (e.g., from about 1 to 30 days). In some embodiments, the sensor is configured for intravascular or extracorporeal implantation (see, e.g., U.S. Patent Application Publication No. US-2005-0143635-A1, U.S. Patent Application Publication No. US-2007-0027385-A1, U.S. Patent Application Publication No. US-2007-0213611-A1, and U.S. Patent Application Publication No. US-2008-0083617-A1, each of which is incorporated by reference herein in its entirety). In some embodiments, the sensor is configured for long-term implantation, such as a wholly implantable sensor, for example. The membrane 32 (e.g., sensing membrane) of some embodiments includes an enzyme domain 46, a resistance domain 48, and a particle-containing domain 50, and may include additional domains, such as an electrode domain 43, and interference domain 44, a cell impermeable domain (also referred to as a bioprotective layer), and/or an oxygen domain (not shown). The membrane 32 is disposed over the electroactive surfaces of the electrode system and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (particle-containing domain and optional interference domain); and/or 5) hydrophilicity at the electrochemically reactive surfaces of the sensor interface (electrolyte domain). However, it is understood that a sensing membrane modified for other sensors, for example, by including fewer or additional domains is within the scope of some embodiments. The membrane can be located over the sensor body by mechanical or chemical methods such as described in U.S. Patent Application Publication No. US-2006-0015020-A1 and U.S. Patent Application Publication No. US-2005-0245799-A1, which are incorporated herein by reference in their entirety. Additional description of the membrane 32 can be found in U.S. Patent Application Publication No. US-2005-0245799-A1 and U.S. Patent Application Publication No. US-2005-0242479-A1 (which describes biointerface and sensing membrane configurations and materials that may be applied to some embodiments) each of which is incorporated herein by reference in its entirety.

In some embodiments, the sensing membrane can be deposited on the electroactive surfaces of the electrode material using known thin or thick film techniques (for example, spraying, electro-depositing, dipping, casting separately from the sensor and then wrapped around it, printing, and the like). It is noted that the sensing membrane that surrounds the working electrode does not have to be the same structure as the sensing membrane that surrounds a reference electrode, etc. For example, the enzyme domain deposited over the working electrode does not necessarily need to be deposited over the reference and/or counter electrodes.

Figure 4A:
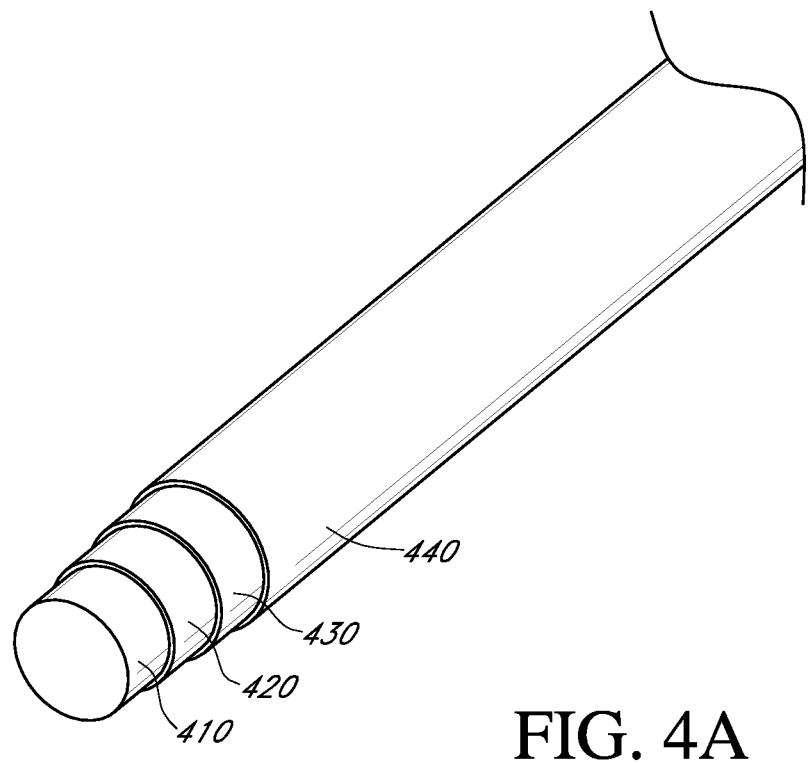
FIG. 4A illustrates one embodiment of the analyte sensor.
Figure 4B:
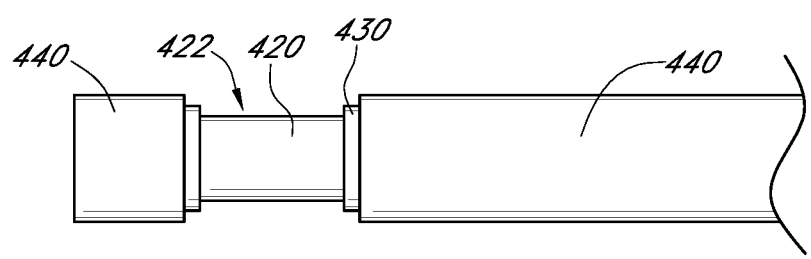
FIG. 4B illustrates the embodiment of FIG. 4A after it has undergone an ablation treatment.

FIG. 4A illustrates another embodiment of an electrode. In this particular embodiment, the electrode comprises a conductive core 410, a first layer 420 that at least partially surrounds the core 410, a second layer 430 that at least partially surrounds the first layer 420, and a third layer 440 that at least partially surrounds the second layer 430. These layers, which collectively form an elongated body, can be deposited onto the conductive core by any of a variety of techniques, such as, for example, by employing dip coating, plating, extrusion, or spray coating processes. In some embodiments, the first layer 420 can comprise a conductive material, such as, for example, platinum, platinum-iridium, gold, palladium, iridium, graphite, carbon, a conductive polymer, an alloy, and/or the like, configured to provide suitable electroactive surfaces for one or more working electrodes. In certain embodiments, the second layer 430 can correspond to an insulator and comprise an insulating material, such as a non-conductive (e.g., dielectric) polymer (e.g., polyurethane, polyimide, or parylene). In some embodiments, the third layer 440 can correspond to a reference electrode and comprise a conductive material, such as, a silver-containing material, including, but not limited to, a polymer-based conducting mixture. FIG. 4B illustrates one embodiment of the electrode of FIG. 4A, after it has undergone laser ablation treatment. As shown, a window region 422 is formed when the ablation removes the second and third layers 430, 440, to expose an electroactive surface of the first conductive layer 420, wherein the exposed electroactive surface of the first conductive layer 420 correspond to a working electrode.

Figure 5A:
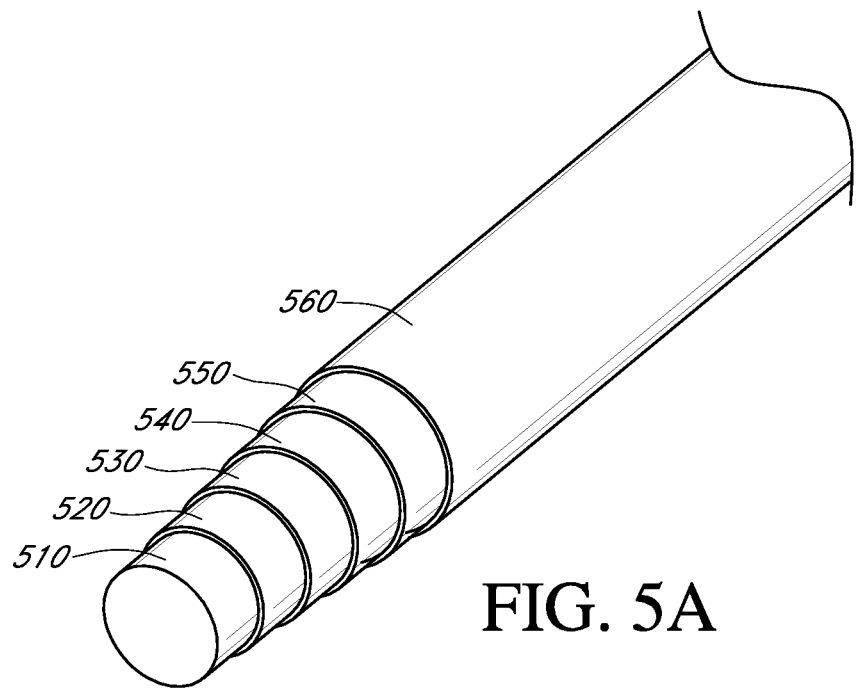
FIG. 5A illustrates another embodiment of the analyte sensor.
Figure 5B:
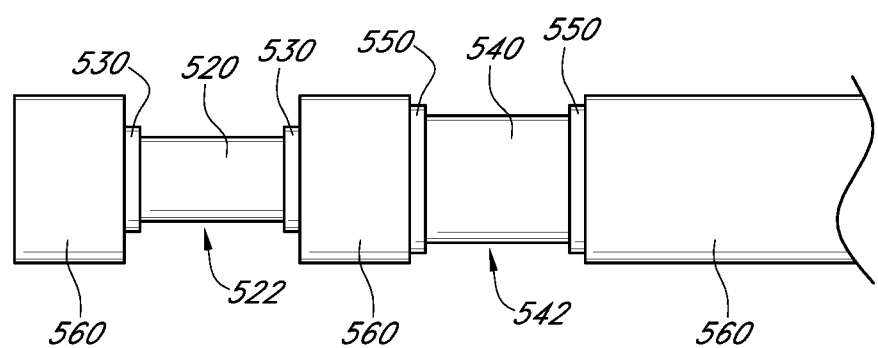
FIG. 5B illustrates the embodiment of FIG. 5A after it has undergone an ablation treatment.

FIG. 5A illustrates another embodiment of an electrode. In this embodiment, in addition to an conductive core 510, a first layer 520, a second layer 530, and a third layer 540, the electrode further comprises a fourth layer 550 and a fifth layer 570. In a further embodiment, the first layer 520 and the second layer 530 can be formed of a conductive material and an insulating material, respectively, similar to those described in the embodiment of FIG. 4A. However, in this particular embodiment, the third layer 540 can be configured to provide the sensor with a second working electrode, in addition to the first working electrode provided by the first layer 520. The fourth layer 550 can comprise an insulating material and provide insulation between the third layer 540 and the fifth layer 560, which can correspond to a reference electrode and comprise the aforementioned silver-containing material. It is contemplated that other similar embodiments are possible. For example, in alternative embodiments, the electrode can have 6, 7, 8, 9, 10, or more layers, each of which can be formed of conductive or non-conductive material. FIG. 5B illustrates one embodiment of the electrode of FIG. 5A, after it has undergone laser ablation treatment. Here, two window regions, a first window region 522 and a second window region 542, are formed, with each window region having a different depth and corresponding to a working electrode distinct from the other.

Particle-Containing Membrane Domain

Referring again to FIG. 3, in preferred embodiments, the continuous analyte sensor includes a particle-containing domain 50 that is capable of reducing noise derived from noise-causing species, such as non-constant noise and/or constant noise. In preferred embodiments, the particle-containing domain 50 is capable of scavenging certain compounds (e.g., interfering species, non-reaction-related hydrogen peroxide, or other electroactive species with an oxidation potential that overlaps with that of hydrogen peroxide) that contribute to non-glucose related signal before they reach the working electrode. Preferably, the particle-containing domain is located more distal to (e.g., radially outward) the sensor's electroactive surface than the enzyme (e.g., enzyme domain). FIG. 3 shows the particle-containing domain 50 as being the most distal membrane domain. However, the particle-containing domain can be located adjacent to the enzyme domain, or between the enzyme domain and a more distal domain. The membrane of FIG. 3 is depicted as being composed of several membrane layers or domains. However, in some embodiments, the membrane can be formed of a single layer that comprises structural and/or functional regions (e.g., the layer can be stratified, as in a gradient). For example, in one embodiment, the single layer can comprise three regions, a proximal region containing the enzyme, an intermediate region configured to restrict diffusion of excess analyte, and a distal region containing the conductive particles dispersed in the material of which the layer is formed and functioning as a particle-containing domain. In other embodiments, for example, the membrane can be formed of two layers, such as a proximal enzyme domain/layer and a distal domain/layer that contains structural and/or functional regions, such as a region that contains the conductive particles and functions as a particle-containing domain. Accordingly, interfering species, non-reaction-related hydrogen peroxide, and/or other electroactive species with an oxidation potential that overlaps with hydrogen peroxide are oxidized/reduced at a location other than the working (measuring) electrode. Thus, sensor baseline is reduced and stabilized, break-in time is reduced, and sensor accuracy is improved.

A variety of noise-causing species can be reduced at a potential of from about ±0.1V to about ±1.2V or more/less; for example, acetaminophen is reduced at a potential of about +0.4 V. In some embodiments, the particle-containing domain is configured to electrochemically oxidize or electrochemically reduce (e.g., electrochemically oxidize/reduce) at least one noise-causing species having a potential within this range, such that the noise-causing species does not substantially interact with the electroactive surface, or contribute to the total signal, as described elsewhere herein. In preferred embodiments, the particle-containing domain is configured and arranged to electrochemically oxidize or electrochemically reduce an amount of non-constant noise-causing species, such that the non-constant noise component of the signal is less than about 20% of the total signal. In more preferred embodiments, the non-constant noise component of the signal is less than about 10% of the total signal. In still more preferred embodiments, the non-constant noise component of the signal is less than about 5% of the total signal.

In some embodiments, no potential is applied to the particle-containing domain (e.g., a "non-powered" particle-containing domain). Non-powered particle-containing domains can be less complicated and less expensive to manufacture, as compared to other types of particle-containing domains described herein. In other embodiments, described elsewhere herein, a potential is applied to the particle-containing domain (a "powered" particle-containing domain). Applying power to the particle-containing domain (e.g., the powered particle-containing domain) can increase the range of noise-causing species that can be electrochemically oxidized/reduced, such as to species having a redox potential outside of the ±0.1V to about ±1.2V range of the non-powered particle-containing domain. In other embodiments, a particle-containing domain is configured to be alternately powered and non-powered for periods of time. In still other embodiments, a non-powered particle-containing domain is configured to generate a potential (e.g., self-powered particle-containing domain). Self-powered particle-containing domains can be less expensive/complicated to manufacture than the powered particle-containing domains but can oxidize/reduce a wider range of interfering compounds than a non-powered particle-containing domain. In some embodiments, a sensor includes two or more particle-containing domains, such as, powered and non-powered domains, powered and self-powered domains, non-powered and self-powered domains, or two different types of non-powered domains, for example.

In preferred embodiments, the particle-containing domain 50 may comprise a non-conductive component with a conductive component dispersed therein, for example, wherein the conductive component comprises a plurality of conductive particles having a sufficient concentration such that current can be transferred between particles, such that the membrane domain is conductive. In some embodiments, the non-conductive component of the particle-containing domain comprises a polymer. In some embodiments, the polymer is analyte-permeable, for example, wherein an analyte, such as glucose, can diffuse through the polymer. In some embodiments, the polymer comprises a hydrophilic polymer. In some preferred embodiments, the polymer comprises at least one of polyurethane or silicone. A variety of hydrophilic polymers, which find use in the preferred embodiments, are described elsewhere herein.

As described above, the particle-containing domain may include a conductive component dispersed throughout a non-conductive component. For example, in some embodiments, the conductive component comprises a plurality of conductive particles. The conductive particles can have a variety of shapes such as but not limited to spherical shapes, irregular, three-dimensional shapes, fibers, micro-laminates of conductive materials and the like, including blends, amalgams, laminates, and the like. The conductive particles may have any appropriate size. For example, in the embodiments wherein the conductive particles have a substantially spherical shape, the particles may be on average from about 0.01 microns to about 2 microns in diameter, preferably from about 0.03 microns to about 1 micron in diameter, and more preferably from about 0.05 microns to about 0.5 microns in diameter. In certain embodiments, the particles may have an average weight of from about $1\times10^{-17}$ grams to about $1\times10^{-10}$ grams, preferably from about $1\times10^{-15}$ grams to about $1\times10^{-11}$ grams, and more preferably from about $1\times10^{-13}$ grams to about $1\times10^{-12}$ grams. The conductive particles can be of any suitable material. In some embodiments, the conductive component is a metal, such as but not limited to platinum, iridium, platinum-iridium, palladium, ruthenium, rhodium, osmium, carbon, graphite, platinum-coated carbon, platinum-coated graphite, gold, and the like. In some embodiments, the conductive component is a conductive polymer, such as but not limited to polyacetylene, polypyrrole, polythiophene, polyaniline, polyfluorene, poly (3-alkylthiophene), polytetrathiafulvalene, polynaphthalenes, poly(p-phenylene sulfide), and poly(para-phenylene vinylene). In some embodiments, the conductive component includes a blend of metals and/or conductive polymers. The conductive particles can be substantially homogeneous or heterogeneous in shape, size, surface area, or composition.

In some embodiments, the conductive particles have a concentration that is sufficient for the particle-containing domain to function as conductive film. In certain embodiments, the concentration of the conductive particles within the particle-containing domain, in volume percentage, is from about 0.1% to about 99.9% of the total volume of the particle-containing domain, preferably from about 0.5% to about 5%, more preferably from about 15% to about 45%, most preferably from about 50% to about 80%. In some embodiments, the particle-containing domain contains from about 1 wt. % or less to about 90 wt. % or more conductive component dispersed in the non-conductive component. In some embodiments, the particle-containing domain contains from about 10 wt. % to about 60 wt. % or more conductive particles dispersed in the non-conductive component, for example, from about 1, 2, 3, 4, 5, 10, 15, 20, 25 or 30% to about 60, 65, 70, 75, 80, 85, or 90%. In preferred embodiments, the particle-containing domain contains from about 20 wt. % to about 40 wt. % or more conductive particles dispersed in the non-conductive component. Increasing the number and/or volume of conductive particles tends to increase the surface area of the particles that are present on the surface of the particle-containing domain. In some embodiments, the effective surface area of the particle-containing domain is more than about 2 times greater than an effective surface of a corresponding domain without conductive particles, preferably more than about 3 times greater, more preferably more than about 5 times greater, more preferably more than about 7 times greater, more preferably more than about 10 times greater, more preferably more than about 20 times greater, more preferably more than about 25 times greater, and most preferably more than about 25 times greater. In embodiments wherein the particle-containing domain is disposed most distal to the sensor's electroactive surface, such as in the embodiment illustrated in FIG. 3, an increase in the effective surface area of the particle-containing domain tends to also increase the effective surface area of the interface between the particle-containing domain and the biological sample (e.g., interstitial fluid, blood, etc.) being tested. In turn, greater amounts of analytes and oxygen can diffuse through the membrane, thereby providing amplification of the analyte signal, as compared to a signal of a corresponding domain without particles. Additionally, with some sensors, electrochemical reactions involving the analyte occurs substantially at the top surface of the domain or of the electroactive surface of the electrode, and the material (e.g., AgCl) used to form the electrode may be consumed during the lifetime of the sensor. Thus, by providing an increased effective surface area, the lifetime for the sensor may be lengthened. In certain embodiments, particles are incorporated into the particle-containing domain to create an uneven and/or irregular surface, such that the effective surface area of the particle-containing domain increases by more than about 20 times, compared to a corresponding domain without the particles and with a substantially evened surface, preferably by more than about 15 times, more preferably by more than about 10 times, more preferably by more than about 3 times, more preferably by more than about 2 times, more preferably by more than about 85 percent, more preferably by more than about 50 percent, and more preferably by more than about 20 percent. The surface area of the particle-containing domain can also be increased by increasing the surface area of the particles, some of which are present on the surface of the particle-containing domain. In some embodiments, the average surface area of the particles is greater than about 20 $m^2/g$, preferably greater than about 50 $m^2/g$, more preferably greater than about 100 $m^2/g$, more preferably greater than about 200 $m^2/g$ and most preferably greater than about 400 $m^2/g$, as determined by the BET (Brunauer, Emmett, Teller) method for determining surface area by physical adsorption of gas molecules.

In certain embodiments the particle-containing domain is configured and arranged to electrochemically oxidize or electrochemically reduce an amount of non-constant noise-causing species, such that the non-constant noise component of the signal is less than about 20% of the total signal. In some embodiments, the non-constant noise component of the signal is less than about 18%, 15%, 10%, 8%, 5%, 3%, or 1% of the total signal for a time period of about 1, 3, 5, 7 or more days.

In preferred embodiments, the conductive component has a sufficiently low reduction/oxidation potential so that a noise-causing (e.g., background-causing) species can be oxidized/reduced, such that the negative effects of noise are substantially reduced, and clinically useful data are provided to the user.

In preferred embodiments, the non-conductive component, in which the conductive component (e.g., conductive particles) is dispersed, is a polymer. In preferred embodiments, the polymer is analyte-permeable. Analyte-permeable polymers that may be used include but are not limited to, hydrophilic and hydrophobic polymer blends that are sufficiently hydrophilic such that the analyte (e.g., glucose) can pass therethrough. These analyte-permeable polymers include but not limited to polyurethanes, polyurethane ureas having about 5% to about 45% hydrophile (e.g., PEO, PVD, or Pluronics) content, silicones, silicone blends (e.g., silicone polymer/hydrophobic-hydrophilic polymer blend; including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers). Additional description of hydrophilic and hydrophobic material blends can be found U.S. Patent Application Publication No. US-2006-0270923-A1, U.S. Patent Application Publication No. US-2007-0027370-A1, U.S. Patent Application Publication No. US-2007-0244379-A1, U.S. Patent Application Publication No. US-2007-0197890-A1, U.S. Patent Application Publication No. US-2008-0045824-A1, and U.S. Patent Application Publication No. US-2006-0258761-A1, each of which is incorporated by reference herein in its entirety.

In one exemplary embodiment, the particle-containing domain comprises a blend of a silicone polymer with a hydrophilic polymer. By "hydrophilic polymer," it is meant that the polymer has an affinity for water, due to the presence of one or more hydrophilic substituents, and generally is primarily soluble in water or has a tendency to absorb water. In one example, the hydrophilic component of a hydrophilic polymer promotes the movement of water and/or compounds in the water (e.g., by diffusion or other means) through a membrane formed of the hydrophilic polymer, such as by lowering the thermodynamic barrier to movement of compounds in the water into the membrane.

Some polymers, such as certain hydrophilic polymers, include both hydrophilic and hydrophobic substituents. The hydrophilic and hydrophobic substituents of a polymer can affect the polymer's behavior in certain circumstances, as seen, for example, in silicone/hydrophilic-hydrophobic blend materials and micellar jackets, which are discussed elsewhere herein. Using PEO-PPO-PEO as an exemplary polymer, the polymer's major component (PEO) is hydrophilic and can provide an overall hydrophilic character to the molecule (e.g., the molecule generally behaves in a hydrophilic manner). However, the hydrophobic component (PPO) of the polymer makes it possible for the polymer to have some hydrophobic character (e.g., for portions of the molecule to behave in the manner of a hydrophobic molecule), in some situations. In some circumstances, such as formation of micellar jackets in a silicone/hydrophilic-hydrophobic blend material, the polymer self-organizes, relative to the silicone (e.g., silicone globule(s)) such that the hydrophobic PPO is adjacent to the silicone (which is hydrophobic) and the two PEO groups project away from the silicone (e.g., due to thermodynamic forces). Depending upon the circumstance (e.g., the polymer selected), variations of the micellar jacket structure described above (e.g., opposite orientations) are possible. For example, it is believed that in a mixture of PPO-PEO-PPO and silicone, the PPO groups self-orient toward the silicone and the PEO center is oriented away from the silicone.

In some embodiments, the non-conductive component includes at least one polymer containing a surface-active group (see U.S. patent application Ser. No. 12/413,231, filed Mar. 27, 2009 and entitled "Polymer Membranes for Continuous In Vivo Analyte Sensors" and U.S. patent application Ser. No. 12/413,166, filed Mar. 27, 2009 and entitled "Polymer Membranes for Continuous In Vivo Analyte Sensors," each of which is incorporated by reference herein in its entirety). In some embodiments, the surface-active group-containing polymer is a surface-active end group-containing polymer. In some embodiments, the surface-active end group-containing polymer is a polymer having covalently bonded surface-active end groups. However, other surface-active group-containing polymers can be formed by: modification of fully-reacted base polymers via the grafting of side chain structures; surface treatments or coatings applied after membrane fabrication (e.g., via surface-modifying additives); blending of a surface-modifying additive to a base polymer before membrane fabrication; immobilization of by physical entrainment during synthesis; and/or the like. Base polymers useful for the preferred embodiments include any linear and/or branched polymer on the backbone structure of the polymer. Suitable base polymers include epoxies, polyolefins, polysiloxanes, polyethers, acrylics, polyesters, carbonates, and polyurethanes, wherein polyurethanes include polyurethane copolymers such as polyether-urethane-urea, polycarbonate-urethane, polyether-urethane, silicone-polyether-urethane, silicone-polycarbonate-urethane, polyester-urethane, and/or the like. Advantageous base polymers of the preferred embodiments are selected for their bulk properties, for example, tensile strength, flex life, modulus, and/or the like, for example, polyurethanes are known to be relatively strong and provide numerous reactive pathways, which properties are advantageous as bulk properties for a membrane domain of the preferred embodiments. Preferred linear base polymers include biocompatible segmented block polyurethane copolymers comprising hard and soft segments. Preferably, the hard segment of the copolymer has a molecular weight of from about 160 to about 10,000, and more preferably from about 200 to about 2,000; while the preferred molecular weight of the soft segment is from about 200 to about 1,000,000, and more preferably from about 400 to 9,000. Preferred polyisocyanates for the preparation of the hard segment of the copolymer are aromatic or aliphatic diisocyanates. The soft segment used in the preparation of the polyurethane is preferably a polyfunctional aliphatic polyol, a polyfunctional aliphatic or aromatic amine, and/or the like useful for creating permeability of the analyte (e.g., glucose) therethrough, for example, polyvinyl acetate (PVA), poly (ethylene glycol) (PEG), polyacrylamide, acetates. polyethylene oxide (PEO), polyethylacrylate (PEA), polyvinylpyrrolidone (PVP), and variations thereof (e.g., PVP vinyl acetate), wherein PVP and variations thereof are be preferred for their hydrolytic stability in some embodiments.

The term "surface-active group" and "surface-active end group" as used herein are broad terms and are used in their ordinary sense, including, without limitation, surface-active oligomers or other surface-active moieties having surface-active properties, such as alkyl groups, which preferentially migrate towards a surface of a membrane formed there from. Surface active groups preferentially migrate towards air (e.g., driven by thermodynamic properties during membrane formation). In some embodiments, the surface-active groups are covalently bonded to the base polymer during synthesis. In some preferred embodiments, surface-active groups include silicone, sulfonate, fluorine, polyethylene oxide, hydrocarbon groups, and the like. The surface activity (e.g., chemistry, properties) of a membrane domain including a surface-active group-containing polymer, reflects the surface activity of the surface-active groups rather than that of the base polymer. In other words, surface-active groups control the chemistry at the surface (e.g., the biological contacting surface) of the membrane without compromising the bulk properties of the base polymer. The surface-active groups of the preferred embodiments are selected for desirable surface properties, for example, non-constant noise-blocking ability, break-in time (reduced), ability to repel charged species, cationic or anionic blocking, and/or the like. In some preferred embodiments, the surface-active groups are located on one or more ends of the polymer backbone, and referred to as surface-active end groups, wherein the surface-active end groups are believed to more readily migrate the surface of the biointerface domain/layer formed from the surface-active group-containing polymer in some circumstances. Additional description of surface-modified polymers and/or membranes can be found in U.S. patent application Ser. No. 12/413,231, filed Mar. 27, 2009 and entitled "Polymer Membranes for Continuous In Vivo Analyte Sensors" and U.S. patent application Ser. No. 12/413,166, filed Mar. 27, 2009 and entitled "Polymer Membranes for Continuous In Vivo Analyte Sensors," each of which is incorporated by reference herein in its entirety.

In some embodiments, one or more domains of the membrane are formed from materials such as silicone, polytetrafluoroethylene, polyethylene-co-tetrafluoroethylene, polyolefin, polyester, polycarbonate, bio stable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. U.S. Patent Application Publication No. US-2005-024579912-A1, which is incorporated herein by reference in its entirety, describes biointerface and sensing membrane configurations and materials that may be applied to some embodiments.

In some embodiments, the particle-containing domain 50 includes a polyurethane (or polyurethane urea) membrane with both hydrophilic and hydrophobic regions to control the diffusion of glucose and oxygen to an analyte sensor, the membrane being fabricated easily and reproducibly from commercially available materials. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer. The material that forms the particle-containing domain can be any of those known in the art as appropriate for use in membranes in sensor device and as having sufficient permeability to allow relevant compounds to pass through it, for example, to allow an oxygen molecule to pass through the membrane from the sample under examination in order to reach the active enzyme or electrochemical electrodes. In some embodiments, the particle-containing domain can be configured from non-polyurethane type materials including but not limited to vinyl polymers, polyethers, polyesters, polyamides, inorganic polymers such as polysiloxanes and polycarbosiloxanes, natural polymers such as cellulosic and protein based materials, and mixtures of combinations thereof. Additional description of polyurethane membranes can be found in PCT International Publication No. WO1992/013271.

In some preferred embodiments, the particle-containing domain is deposited on to the enzyme domain, such as, but not limited to, one that is part of a membrane system comprising as one or more planar and/or concentric layers. The deposition may yield a domain thickness from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5, or 3 microns to about 3.5, 4, 4.5, or 5 microns. The particle-containing domain may be deposited by any of variety of techniques, such as, vapor deposition, spray coating, spin coating, or dip coating, for example. In one preferred embodiment, dipping is the preferred deposition technique.

As described elsewhere herein, some of the particle-containing domains described herein may have a conductive particles concentration that is sufficient for the particle-containing domains to function as conductive films. In addition to being capable of functioning as conductive films, some of these particle-containing domains are capable of allowing for diffusion of certain analytes (e.g., glucose) and gases (e.g., oxygen) therethrough. In some embodiments, the particle-containing domain has a glucose diffusion coefficient greater than about $1\times10^{-15}$ m$^2$/s in vivo, preferably greater than about $1\times10^{-13}$ m$^2$/s, and more preferably greater than about $1\times10^{-10}$ m$^2$/s. In some embodiments, the particle-containing domain has an oxygen diffusion coefficient greater than about $1\times10^{-11}$ m$^2$/s, preferably greater than about $1\times10^{-9}$ m$^2$/s, and more preferably greater than about $1\times10^{-7}$ m$^2$/s.

The use of conductive particles dispersed in a non-conductive polymer to form the particle-containing domain provides a number of advantages with respect to noise reduction. Namely, by oxidizing/reducing noise-causing species at a location other than the working electrode, the non-glucose related signal (e.g., constant and/or non-constant noise) can be reduced or eliminated, thereby increasing sensor accuracy. Advantageously, known thin-film, printing or molding methods (e.g., dip, spray, mold, print, and the like; onto a support or self-supporting) can be used in formation of the particle-containing domain.

The particle-containing domain can be used to serve a variety of functions other than noise reduction. For example, in some embodiments, the particle-containing domain can be used in an oxygen-generating membrane. There typically exists a molar excess of glucose relative to the amount of oxygen in blood and interstitial fluid. For every free oxygen molecule in extracellular fluid, there can be more than 100 glucose molecules present (see Updike et al., *Diabetes Care* 5:207-21(1982)). When a glucose-monitoring reaction becomes oxygen-limited, linearity of glucose measurement response cannot be achieved above minimal glucose concentrations. While the use of a semipermeable membrane (e.g., a diffusion resistance domain) situated over the enzyme domain to control the flux of glucose and oxygen can increase the level of glucose concentration at which linearity can be achieved, the use of a layer capable of generating oxygen can further increase the aforementioned level of oxygen, and/or allow for a reduction in the thickness of the diffusion resistance domain, or even entirely eliminate the need for a diffusion resistance domain. In turn, this allows for the design of a glucose sensor with very high sensitivity. In some embodiments, the electroactive surface of the working electrode can be biased at first potential (e.g., 1.2V), to electrolytically break down water, through which a sufficient amount of oxygen can be generated to ensure that oxygen is in excess of glucose, so that glucose is the limiting factor in the measurement process, instead of oxygen. The oxygen generated from this process then diffuses through to the particle-containing layer, which can be biased at a second potential lower than the first potential, and to an enzyme layer that is adjacent (distal or proximal) to the particle-containing layer. Optionally, an oxygen permeable layer, such as one comprising PTFE or Teflon®, can be disposed between the particle-containing layer and the electroactive surface. In these embodiments, the particle-containing layer can serve as a sensor element to measure glucose concentration.

In other embodiments, one or more particle-containing domains can be used to create a layered sensor comprising multiple sensor elements that are layer-separated. For instance, the membrane system may comprise multiple (e.g., two, three, four, or more) enzyme layers interspersed with particle-containing domains configured to selectively allow certain analytes to pass therethrough and configured to block or reduce the flow therethrough of other analytes and/or products (e.g., $H_2O_2$) of electrochemical reactions involving analytes. As an example, in one embodiment, the membrane system may comprise a first enzyme layer configured to catalyze the electrochemical reaction of a first analyte, a second enzyme layer configured to catalyze the electrochemical reaction of a second analyte, and a third enzyme layer configured to catalyze the electrochemical reaction of a third analyte. Associated with the three enzyme layers are three sensor elements in the form of particle-containing domains and/or the electrode electroactive surface configured to measure products of the afore-mentioned electrochemical reactions. In alternative embodiments, one or more of the particle-containing domains and/or the electrode electroactive surface may directly measure the analyte, instead of the product of the analyte's reaction with a co-reactant. As another example, the multiple sensor elements of the sensor can each be configured to detect glucose, with each configured to measure glucose using a different mechanism or setting. For instance, the plurality of sensor elements may each be configured to measure glucose using a different bias potential. Alternatively or additionally, the plurality of sensor elements may each be tuned to measure a specific glucose concentration range that differs from that of the other sensor elements. In still another embodiment, the membrane system may comprise a sensor element configured to measure an analyte and another sensor element configured to measure a drug of interest. In this particular embodiment, the particle-containing domain may be used to preferentially screen out the drug of interest from the analyte-sensing sensor element.

The particle-containing domain may also be used to serve as cover layer, i.e., a layer that is most distal with respect to the electrode electroactive surface, to physically protect the other membrane layers proximal to the cover layer, and to serve as an electrical connector. For example, in one embodiment, the reference electrode may comprise a Ag/AgCl layer disposed over an electrode surface, and a particle-containing domain may be provided to cover the Ag/AgCl layer, so as to prevent silver-containing particulates from coming off the membrane system and into host tissue, all the while still allowing an electrical connection to the reference electrode.

In some embodiments, the membrane applied to an analyte sensor includes a particle-containing domain 50 including a dispersion of a plurality of conductive particles in an analyte-permeable polymer material. In one exemplary embodiment, the dispersion is applied to the sensor after enzyme domain formation (e.g., such that the particle-containing domain is more distal to the electroactive surface than the enzyme domain). The dispersion can be applied either directly on the enzyme domain, or additional membrane domains and/or layers (e.g., interference domain, resistance domain, and the like) can be applied to the sensor (before/after enzyme domain formation) prior to application of the dispersion. In some embodiments, the dispersion is applied directly on the enzyme domain. The dispersion can be applied by any thin film technique known in the art, such as but not limited to dipping, spraying, spin-coating, molding, vapor deposition, and the like. In some embodiments, one or more layers of the dispersion are applied by dipping the sensor into the particle-containing domain material, followed by curing. In some embodiments, the particle-containing domain is formed of a single layer of the material. In other embodiments, the particle-containing domain is formed of two or more layers (e.g., two or more dips, with curing following each dip) of the dispersion. In preferred embodiments, the particle-containing domain is formed of about 2, 3, 5, 10, 15, 20 or 30 layers of the cured dispersion. In some embodiments, the particle-containing domain can be formed separately from the sensor (e.g., as a film) and subsequently applied thereto (e.g., by wrapping the film around at least a portion of the in vivo portion of a completed sensor). In some embodiments, a particle-containing domain can be applied to the sensor as one or more layers by applying the non-conductive component to the sensor, followed by rolling the sensor in the conductive component, followed by curing. For example, in one embodiment, alternating layers of conductive and non-conductive components can be applied to the sensor to form the particle-containing domain (e.g., by sequentially applying the non-conductive component and rolling the sensor in the conductive component one or more times).

While the above embodiments of the particle-containing domain are described in the context of being non-powered, in some embodiments, the particle-containing domain is powered, such as by applying a potential thereto. For example, the voltage setting necessary to react with noise-causing species depends on the target noise-causing species, for example, from about ±0.1 V to about ±1.2 V for noise-causing species of $H_2O_2$—detecting electrochemical sensor. In some circumstances, such as with a sensor configured to detect another analyte, for example, higher and/or lower voltages (e.g., less than −1.2 V and greater than +1.2 V) may be necessary to react with noise-causing species. In some embodiments, an external potentiostat or other sensor electronics is/are operably connected to the particle-containing domain, such that a bias potential can be applied thereto, thereby enabling the electrochemical oxidation/reduction of the noise-causing species. In some embodiments, wherein the powered particle-containing domain is set at a potential of from about ±0.6 to about ±1.2 V, both oxygen-generation and noise-causing species modification can be achieved. In some embodiments, wherein the powered particle-containing domain is set at a potential below about ±0.6 V, the powered particle-containing domain will function to electrochemically oxidize/reduce noise-causing species. In some embodiments, a potential of about ±0.1V to about ±0.8V is applied to the particle-containing domain, such that at least one non-constant noise-causing species is electrochemically reduced/oxidized, such that the non-constant noise component of the total signal is less than about 20% (of the total signal). Preferably the non-constant noise component of the signal is less than about 10% of the total signal. More preferably, the non-constant noise component of the signal is less than about 5% of the total signal. In some embodiments, it is preferred to apply a potential of from about ±0.3V to about ±0.7V to the particle-containing domain, such that the non-constant noise component of the signal is less than about 20%, 15%, 10% or 5% of the total signal. In more preferred embodiments, the potential applied to the particle-containing domain is from about ±0.5V to about ±0.6V, such that the non-constant noise component of the signal is less than about 20%, 15%, 10% or 5% of the total signal. In some further embodiments, a potential applied to the particle-containing domain can be constant, cyclical, pulsed, intermittent, variable, or a combination thereof. For example, in some embodiments, the potential applied to the particle-containing domain is set at a constant voltage (e.g., ±0.2V, ±0.5V, ±0.7V, etc.). In another exemplary embodiment, a pulsed potential applied to the particle-containing domain is turned on and off. In still another example, in one embodiment, the potential is oscillated between at least two potentials, such as between ±0.1V and ±0.6V, or such as between ±0.2V and ±0.5V.

In one exemplary embodiment, a "powered" particle-containing domain is a membrane domain formed of conductive particles dispersed in an analyte-permeable polymer, as described elsewhere herein, and operatively connected to sensor electronics. In some embodiments, the powered particle-containing domain is configured to be between the enzyme domain and the outside fluid, when the sensor is implanted in vivo. In some embodiments, the powered particle-containing domain is formed adjacent to the enzyme domain. In a further embodiment, at least one additional domain (resistance, interference, cell disruptive and/or cell impermeable domain) is formed above and/or below the particle-containing domain (e.g., more proximal to and/or distal to the electroactive surface of the electrode than the powered particle-containing domain). In some embodiments, the powered particle-containing domain is configured as a most distal domain of the membrane. In some circumstances, at least one intervening domain (e.g., a resistance and/or interference domain) is formed between the enzyme domain and the particle-containing domain.

Some analytes can fall to such low-levels that they are difficult to accurately measure with standard sensors. In some embodiments, the powered particle-containing domain can be configured as a plurality of alternating polarized layers (e.g., alternately anodically or cathodically polarized by applying alternate voltages to the layers), such that a molecule (e.g., an analyte, a noise-causing species) can be alternately and repeatedly oxidized and reduced as the molecule passes through at least some of the layers. In some embodiments, the noise reducing domain comprises a plurality of alternately polarized layer and is configured to amplify an analyte signal (e.g., the signal of a very low concentration analyte). For example, in one embodiment, the analyte is reduced as it passes through a first layer, then the reduced analyte is oxidized as it passes through the second layer, then oxidized analyte is reduced again as it passes through the third layer, then reduced analyte is oxidized a second time as it passes through the fourth layer, and so on, such that the analyte signal is amplified. Thus, accurate measurement of reduced analyte concentrations (e.g., about 80 mg/dL, 70 mg/dL, 60 mg/dL, 50 mg/dL, 40 mg/dL, 30 mg/dL, 20 mg/dL, 10 mg/dL glucose or less) is enabled.

In some embodiments, it is preferred to form a particle-containing domain wherein the conductive particles function as electrochemical cells (e.g., Galvanic cells) having a potential sufficient to render a non-constant noise-causing species molecule substantially unable to interact with the sensor's electroactive surface. Since this type of particle-containing domain is configured and arranged to generate a potential, it can be referred to as a "self-powered" particle-containing domain. Accordingly, sufficient quantities (e.g., densities) of both positive and negative conductive particles are selected and dispersed within the non-conductive component, wherein the positive particles and negative particles are configured and arranged such that a positive particle and a negative particle form an "electrochemical cell" having a potential sufficient to render a non-constant noise-causing species molecule substantially unable to electrochemically react with the electroactive surface. In preferred embodiments, the plurality of positive and negative particles form a sufficient number of sites for the electrochemical oxidation/reduction of non-constant noise-causing species diffusing through the particle-containing domain, such that the non-constant non-analyte-related noise signal component is less than 20% of the total signal. For example, particles of two dissimilar metals, such as but not limited to silver and gold particles, or platinum and iron particles. Preferably, a sufficient concentration (e.g., from about 20% to about 70%) of each type of conductive particles is dispersed in the non-conductive material such that a potential difference generated between the two types of conductive particles is sufficient to react with a wider variety/spectrum of noise-causing species than is possible with a single type of conductive material, or in some circumstances, the analyte. In other words, the two types of conductive particles behave as "miniature batteries." In preferred embodiments, the conductive particles (e.g., dissimilar metal particle pairs) have sufficient concentration that they are within the diffusion path of noise-causing species. In certain circumstances, it is preferred to apply a potential to this type of particle-containing domain (e.g., powered).

While not wishing to be bound by theory, it is believed that a powered particle-containing domain can reduce current that can be generated by one or more noise-causing species (e.g., diffusing through the particle-containing domain) having different redox potentials. For example, the conductive particles can form a network (within the particle-containing domain) that can function as an array of microelectrodes. Additionally, the powered particle-containing domain can provide all of the advantages described herein for non-powered particle-containing domains.

Sensor Electronics

In preferred embodiments, the sensor includes sensor electronics, including a processing module, a receiver, and the like, such as those applicable to a variety of continuous analyte sensors, such as non-invasive, minimally invasive, and/or invasive (e.g., transcutaneous, intravascular and wholly implantable) sensors. For example, descriptions of sensor electronics and data processing as well as the receiver electronics and data processing can be found in U.S. Patent Application Publication No. US-2005-0245799-A1, U.S. Patent Application Publication No. US-2006-0015020-A1, U.S. Patent Application Publication No. US-2006-0020187-A1, and U.S. Patent Application Publication No. US-2007-0208245-A1, each of which is incorporated herein by reference in its entirety. In general, electrodes of the sensor described above are electrically coupled at their ends to the sensor electronics. In some embodiments, the particle-containing domain is electrically coupled to the sensor electronics.

Figure 6:
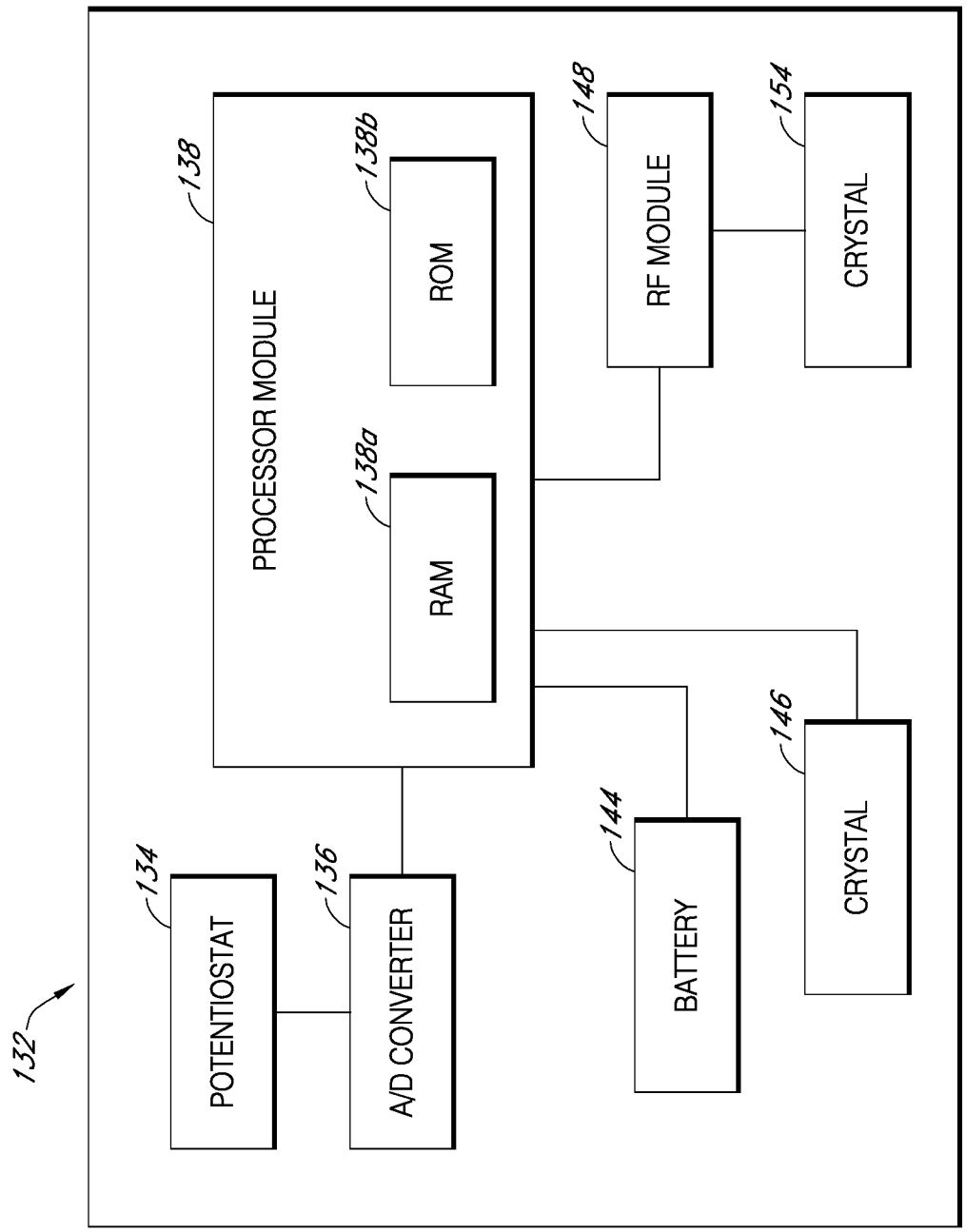
FIG. 6 is a block diagram illustrating the components of sensor electronics, in one embodiment.

FIG. 6 is a block diagram that illustrates one possible configuration of the sensor electronics 132 in one embodiment. In this embodiment, a potentiostat 134 is shown, which is operatively connected to an electrode system (e.g., FIG. 2) and provides a voltage to the electrodes, which biases the sensor to enable measurement of a current value indicative of the analyte concentration in the host (also referred to as the analog portion). The potentiostat 134 (or an optional potentiostat, not shown) is operably associated with the powered particle-containing domain, to provide a bias potential for oxidizing/reducing noise-causing species, as described elsewhere herein. In some embodiments, the potentiostat includes a resistor (not shown) that translates the current into voltage. In some alternative embodiments, a current to frequency converter is provided that is configured to continuously integrate the measured current, for example, using a charge counting device. In the illustrated embodiment, an A/D converter 136 digitizes the analog signal into "counts" for processing. Accordingly, the resulting raw data stream in counts is directly related to the current measured by the potentiostat 134.

A processor module 138 is the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in more detail elsewhere herein). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, ROM 138b provides semi-permanent storage of data, for example, storing data such as sensor identifier (ID) and programming to process data streams (e.g., programming for signal artifacts detection and/or replacement such as described elsewhere herein). In one exemplary embodiment, RAM 138a can be used for the system's cache memory, for example for temporarily storing recent sensor data.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor/transmitter ID code, raw data, filtered data, and/or error detection or correction. The processor module can be configured to transmit any combination of raw and/or filtered data.

A battery 144 is operatively connected to the processor 138 and provides the necessary power for the sensor (e.g., FIG. 2, 34). In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example. A Quartz Crystal 146 is operatively connected to the processor 138 and maintains system time for the computer system as a whole.

An RF module (e.g., an RF Transceiver) 148 is operably connected to the processor 138 and transmits the sensor data from the sensor to a receiver. Although an RF transceiver is shown here, some other embodiments can include a wired rather than wireless connection to the receiver. A second quartz crystal 154 provides the system time for synchronizing the data transmissions from the RF transceiver. It is noted that the transceiver 148 can be substituted with a transmitter in other embodiments. In some alternative embodiments, however, other mechanisms, such as optical, infrared radiation (IR), ultrasonic, and the like, can be used to transmit and/or receive data.

Additional description of sensor electronics can be found in U.S. Pat. Nos. 7,366,556, 7,310,544, U.S. Patent Application Publication No. US-2005-0154271-A1, U.S. Patent Application Publication No. US-2005-0203360-A1, U.S. Patent Application Publication No. US-2005-0027463-A1, U.S. Patent Application Publication No. US-2006-0020188-A1, U.S. Patent Application Publication No. US-2006-258929-A1, U.S. Patent Application Publication No. US-2007-0032706-A1, U.S. Patent Application Publication No. US-2007-0016381-A1, U.S. Patent Application Publication No. US-2007-0203966-A1, and U.S. Patent Application Publication No. US-2008-0033254-A1, each of which is incorporated herein by reference in its entirety.

Particulate Electrodes

In some embodiments, the material used to form the particle-containing domain (e.g., the conductive and non-conductive components) can be formed into an electrode (referred to as a "particulate electrode" herein), such as but not limited to a replacement for a wire electrode, for example. In an exemplary embodiment, a particulate electrode is formed as a drawn "wire," such as by extrusion and/or molding of the particle-containing domain material. For example, such a particulate electrode wire could be used as the working electrode 38 of FIGS. 2 and 3, in some embodiments. However, the particulate electrode can have any useful shape, such as but not limited to planar, rectangular, ovoid, spheroid, round, circular, cylindrical, prismatic and coiled (e.g., 30, FIG. 2) shapes, sheets, films, and the like. Additionally, the particulate electrode is configured and arranged for connection to the sensor electronics, such that the sensor electronics can generate a signal associated with the analyte (e.g., glucose, calcium, pH, sodium, potassium, oxygen, carbon dioxide/bicarbonate, blood nitrogen urea (BUN), creatinine, albumin, total protein, alkaline phosphatase, alanine amino transferase, aspartate amino transferase, bilirubin, and/or hematocrit) concentration of a host.

In one exemplary embodiment, the working electrode is a wire-shaped electrode formed from a plurality of platinum particles dispersed in a non-conductive, non-analyte-permeable material (or an analyte-permeable material), wherein the platinum particles are of a sufficient concentration that $H_2O_2$ can be oxidized at the electrode surface, by loss of an electron, and a current is generated that is detected by the sensor electronics. While not wishing to be bound by theory, it is believed that replacing a metal electrode (e.g., a platinum electrode) with a particulate electrode (e.g., platinum particles distributed in a non-conductive material) can reduce manufacturing costs, such as due to the use of a smaller amount of an expensive material (e.g., platinum), for example.

In one exemplary embodiment, a continuous analyte sensor, configured for in vivo detection of an analyte, includes a particulate electrode formed of a non-analyte-permeable material and a plurality of conductive particles distributed throughout the non-analyte-permeable material, a sensor membrane, and sensor electronics configured and arranged to generate a signal associated with the analyte. In preferred embodiments, the non-analyte-permeable material is a polymer. Analyte-impermeable polymers (e.g., polysulfones, polyesters, polyurethanes, vinyls, acetates) can be used as the non-analyte-permeable material in some embodiments. However, in some alternative embodiments, analyte-permeable polymers (e.g., polyurethanes including hydrophilic groups, silicone polycarbonate urethanes, polyurethanes, silicones, Silicone-PLURONIC® blends, and the like) or blends of analyte-permeable and analyte-impermeable polymers can be used in place of the non-analyte-permeable material. In some embodiments, the conductive particles (e.g., platinum, platinum-iridium, iridium, palladium, graphite, gold, silver, silver chloride, carbon, or conductive polymers, or mixtures, alloys or nanocomposites thereof) are from about 1 wt. % or less to about 60 wt. % or more of the electrode. In more preferred embodiments, the conductive particles are from about 5 wt. %, 10 wt. %, 15 wt. %, 20 wt. %, 25 wt. % or 30 wt. % to about 35 wt. %, 40 wt. %, 45 wt. %, 50 wt. %, 55 wt. % or 60 wt. % of the electrode. Additionally, the particulate electrode can be formed into a variety of shapes, such as but not limited to a wire, a fiber, a string, a sheet, a rod, an orb, a sphere, a ball, an egg, a pyramid, a cone, a cube, a rectangle, a polygon, or a polyhedron.

The size of the individual particles, in diameter or the longest dimension, can be selected, e.g., in view of the shape of the particulate electrode or the nature of the conductive material comprising the particle, however a particle size of from about 1 nm or less to about 500 microns or more, preferably from about 10, 20, 50, 100, or 500 nm to about 1, 10, 50, 100, 200, 300, or 400 microns is generally preferred. The particles can be of a substantially uniform size distribution, that is, a majority of the particles can have a diameter (or longest dimension) generally within about ±50% or less of the average, mean, or mode diameter (or average, mean, or mode longest dimension), preferably within about ±45%, 40%, 35%, 30%, 25%, or 20% or less of the average, mean, or mode diameter (or average, mean, or mode longest dimension). While a uniform size distribution may be generally preferred, individual particles having diameters (or longest dimension) above or below the preferred range may be present, and may even constitute the majority of particles present, provided that a substantial amount of particles having diameters in the preferred range are present. In other embodiments, it may be desirable that the particles constitute a mixture of two or more particle size distributions, for example, a portion of the mixture may include a distribution on nanometer-sized particles and a portion of the mixture may include a distribution of micron-sized particles. The particles of preferred embodiments may have different forms. For example, a particle may constitute a single, integrated particle not adhered to or physically or chemically attached to another particle. Alternatively, a particle may constitute two or more agglomerated or clustered smaller particles that are held together by physical or chemical attractions or bonds to form a single larger particle. The particles may have different atomic level structures, including but not limited to, for example, crystalline, amorphous, and combinations thereof. In various embodiments, it may be desirable to include different combinations of particles having various properties, including, but not limited to, particle size, shape or structure, chemical composition, crystallinity, and the like. The individual particles can be of any desired shape (e.g., substantially spherical, faceted, needle-like, rod-like, irregular, or the like). The particles can be irregularly distributed in the particulate electrode, uniformly distributed throughout the particulate electrode, or the electrode can include a gradient of particle sizes, or domains with different particle sizes. The particles can be identical in one or more features (composition, shape, size), or different in one or more features (e.g., a bimodal size distribution of compositionally-identical particles, or particles of different size but identical composition). The particles can include metal oxides, or nonconductive components (e.g., a nonconducting core coated with or surrounded by metal or another conductor), provided that the particles impart a desired degree of conductivity to the electrode. The particles can be solid, porous (with pores open to the surface of the particle), or contain enclosed voids.

In one exemplary embodiment, the particulate electrode includes a support upon which the electrode is disposed. For example, the support can be formed of a dielectric material, such as plastic, polymer, ceramic or glass. The particulate electrode can be disposed on the support as a film made of the non-analyte-permeable material and the plurality of conductive particles, using any thin- or thick-film techniques known in the art, such as silk screening, sputtering, etching, spin coating, non-impact printing, impact printing and the like.

In preferred embodiments, a sensor membrane system is disposed on the electrode, as described elsewhere herein. For example, in the case of a "wire"-shaped particulate electrode, the membrane system can be disposed coaxially thereon, such as is shown in FIG. 2, for example.

In some embodiments, the particulate electrode is a working electrode, as described elsewhere herein, and the sensor includes at least one additional electrode, such as but not limited to a second working electrode, a reference electrode, a counter electrode, and the like. In one exemplary embodiment, the additional electrode is a second working electrode and comprises a plurality of conductive particles distributed throughout a polymer material (e.g., analyte-permeable or non-analyte permeable). The conductive particles and polymer material can be the same as those used to form the working electrode (e.g., first working electrode, above) or they can be different materials. For example, if the additional electrode is a second working electrode, it can be formed of platinum particles distributed in a polymer material, whereas, if the additional electrode is a reference electrode, it can be formed of silver/silver-chloride particles distributed in the polymer material. Accordingly, the conductive particles and polymer materials selected to form each electrode can be selected to optimize sensor function.

While not wishing to be bound by theory, the particulate electrode provides for simplified manufacturing techniques and is formable/conformable into a variety of shapes and/or depositable onto on a variety of shaped supports. For example, in some embodiments, the material used to form the particulate electrode (e.g., particles of the conductive component dispersed in the non-conductive component) can be molded and/or shaped into any desired shape or size. For example, the material can be mold into a geometry optimized for implantation, a reduced footprint, and the like. For example, in one exemplary embodiment, the material for the particulate electrode is formed by blending a plurality of conductive particles and a liquid polymer to form the electrode material, using known techniques. Then the particulate electrode is formed from the blended electrode material. After the electrode has been formed, a membrane system is applied; and the electrode is functionally connected to sensor electronics (e.g., wherein the sensor electronics are configured and arranged to detect a signal associated with an analyte). In some embodiments, the electrode material is extruded to form the electrode. However, in other embodiments, the electrode material is deposited on a support. In still other embodiments, the electrode can be formed by molding the electrode material.

In some embodiments, the powered particulate electrode is configured as a plurality of alternating polarized layers (e.g., alternately anodically or cathodically polarized by applying alternate voltages to the layers), as described elsewhere herein. While not wishing to be bound by theory, it is believed that such a structure can be used to detect an analyte at a very low concentration; namely, because as the analyte passes through at least some of the multiple layers, it can be alternately oxidized and reduced a plurality of time, thereby amplifying the signal. In one exemplary embodiment, a detectable electrochemical tag is configured to detect an analyte of interest. For example, a probe configured to detect a target molecule is labeled with a species (e.g., an analyte, acetaminophen, ascorbic acid and the like) that can be detected by the powered particulate electrode. In one exemplary embodiment, an RNA probe to detect the transcripts of an expressed gene can be labeled with acetaminophen. The labeled probe is mixed with a sample containing expressed RNAs, such that hybridization can occur between the probe and RNAs containing the probe's target sequence, followed by washing or another type of purification of the RNA hybrids, and then detection of the probe (e.g., via the acetaminophen) with a powered particulate electrode of this embodiment.

Advantageously, the material properties of the polymer, such as but not limited to strength and resistance to fatigue, can be imparted to the particulate electrode. Additionally, the use of conductive particles dispersed in a polymer to form the particulate electrode, such as to replace the platinum working electrode, can substantially lower manufacturing costs, relative to the cost of traditional materials due to the high surface area of the electroactive surfaces in conjunction with a reduced volume of electrode material.

EXAMPLES

Example 1

Effect of Particle-Containing Domain Composition on Sensor Function

Small structured continuous glucose sensors were constructed, including a membrane having enzyme (e.g., GOX) and polyurethane resistance domains. The sensors were divided into three groups, 1) a control group having no particle-containing domain applied (Control), 2) a test group having a non-powered particle-containing domain including platinum particles and carbon particles (e.g., the conductive component) dispersed in a silicone polymer blend (the non-conductive component) (Si+Pt/C), and 3) another test group having a particle-containing domain including only platinum particles dispersed in a silicone polymer blend (Si+Pt). The completed sensors were placed in a PBS buffer solution until sensor break-in was complete. Then the sensors were sequentially placed in PBS solutions containing glucose (100-mg/dL), $H_2O_2$ (200 µM) and/or acetaminophen (220 µM). The $H_2O_2$ solution represents an internally derived noise-producing species (e.g., produced inside the host's body). The acetaminophen solution represents and externally derived noise-producing species (e.g., administered to a host).

Test results are shown in Table 1. When the control sensors were exposed to the $H_2O_2$ and acetaminophen solutions, the signal increased approximately 7-fold and 4-fold, respectively. The inclusion of a noise-reduction domain (Si+Pt/C and Si+Pt) substantially increased the glucose signal (e.g., about 3- and 6-fold, respectively) and substantially decreased $H_2O_2$ and acetaminophen signals, as compared to control sensors.

TABLE 1

| | Average Signal Measured (pA) | | |
| --- | --- | --- | --- |
| Test Solution | Control | Si + Pt/C | Si + Pt |
| Glucose (100 mg/dL) | 1,140 | 3,250 | 6,220 |
| $H_2O_2$ (200 µM) | 7,470 | 890 | 810 |
| Acetaminophen (0.22 µM) | 4,020 | 1,170 | 1,970 |

While not wishing to be bound by theory, it is believed that a particle-containing domain formed of a conductive component (e.g., the metal particles) dispersed in a non-conductive component (e.g., the silicone material) can substantially reduce signal from noise-causing species by oxidizing or reducing the noise-causing species, such that the noise-causing species is rendered substantially unable to interact with the sensor's electroactive surface.

Example 2

Effect of Conductive Component Concentration on Particle-Containing Domain Function Small structured continuous glucose sensors were constructed, including a membrane having enzyme (e.g., GOX) and polyurethane resistance domains. The sensors were divided into three groups and then particle-containing domain materials, having different concentrations of platinum particles were applied. The non-powered particle-containing domain of the first group (Si) included no conductive component. The non-powered particle-containing domain of the second group (Si+0.1% Pt) included 0.1 wt % platinum particles (the conductive component) dispersed in the silicone material (the non-conductive component). The non-powered particle-containing domain of the third group (Si+1% Pt) included 1 wt % platinum particles (the conductive component) dispersed in the silicone material (the non-conductive component). The completed sensors were placed in a PBS buffer solution until sensor break-in was complete; followed by sequential testing in PBS solutions containing glucose (100-mg/dL), $H_2O_2$ (200 μM) or acetaminophen (220 μM).

Table 2 illustrates the test results. Compared to the results of the Si sensors (no conductive component), addition of platinum particles to the particle-containing domain (Si+ 0.1% Pt and Si+1% Pt) had no significant effect on glucose signal measured. However, addition of platinum particles substantially reduced the signal from both internally and externally derived noise-causing species. For example, inclusion of 1% Pt particles in the particle-containing domain resulted in an approximately 50% in the $H_2O_2$ signal, while the 1% Pt blocked nearly 100% of the $H_2O_2$ signal. In another example, the 1% Pt blocked about 46% of the acetaminophen signal, while 0.1% Pt had no significant effect on the acetaminophen signal measured.

TABLE 2

| Test Solution | Average Signal Measured (pA) | | |
|---|---|---|---|
| | Si | Si + 0.1% Pt | Si + 1% Pt |
| Glucose (100 mg/dL) | 15,590 | 16,690 | 11,780 |
| $H_2O_2$ (200 μM) | 6,560 | 3,520 | 470 |
| Acetaminophen (0.22 μM) | 7,660 | 7,730 | 4,200 |

While not wishing to be bound by theory, it is believed that a particle-containing domain including about 0.1 wt %, 1 wt % or more platinum particles can increase sensor glucose sensitivity while substantially blocking signal from internally and/or externally derived noise-causing species (e.g., $H_2O_2$ or acetaminophen, for example).

Example 3

Effectiveness of Particle-Containing Domains Constructed by Alternate Methods

Small structured continuous glucose sensors were constructed, including a membrane having enzyme (e.g., GOX) and polyurethane resistance domains. The sensors were then sprayed with an additional layer of resistance domain material, including 5% Chronothane H (e.g., the non-conductive component) in THF. Next, the sensors were divided into three groups. The first group of sensors had no particle-containing domain applied. The second group of sensors was sprayed with an additional 24 layers of the polyurethane solution and then cured. The third group of sensors was sprayed with an additional 3 layers of the polyurethane solution, lightly rolled in platinum particles and then cured.

The three groups of sensors were placed in a PBS solution until sensor break-in was complete. Then, the sensors were tested sequentially in PBS solutions containing 40 mg/dL glucose, 200 mg/dL glucose, 400 mg/dL glucose, 200 μM $H_2O_2$ or 0.12 μM acetaminophen, and the ratio of noise signal to glucose signal examined. Table 3 shows the experimental results.

TABLE 3

| Sensor Type | Sensor Sensitivity (pA/mg/dL) | Signal Ratio | |
|---|---|---|---|
| | | $H_2O_2$/ Glucose | Acetaminophen/ Glucose |
| Control | 9.84 | 2.89 | 1.9 |
| 24x Polyurethane | 28.01 | 0.92 | 0.59 |
| 3x Polyurethane + Pt | 28.5 | 0.15 | 0.77 |

As shown in Table 3, applying the non-conductive material (polyurethane) of the non-powered particle-containing domain to the sensor both substantially increased glucose sensitivity and substantially reduced signal from the exemplary noise-causing species ($H_2O_2$ and acetaminophen). Application of the conductive material (platinum particles) to the non-powered particle-containing domain substantially attenuated noise from $H_2O_2$ an additional amount over the $H_2O_2$ signal blocked by the non-conductive material alone. While not wishing to be bound by theory, it is believed that a particle-containing domain formed of a conductive component (e.g., the metal particles) dispersed in a non-conductive component (e.g., the polyurethane material) can substantially reduce signal from noise-causing species by oxidizing or reducing the noise-causing species, such that the noise-causing species is rendered substantially unable to interact with the sensor's electroactive surface.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; 7,110,803; 7,192,450; 7,226,978; 7,310,544; 7,364,592; 7,366,556; 7,424,318; 7,471,972; 7,460,898; 7,467,003; 7,497,827; 7,519,408, and 7,583,990.

Methods and devices that are suitable for use in conjunction with aspects of the preferred embodiments are disclosed in U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No.

US-2006-0016700-A1; U.S. Patent Publication No.
US-2006-0142651-A1; U.S. Patent Publication No.
US-2006-0086624-A1; U.S. Patent Publication No.
US-2006-0068208-A1; U.S. Patent Publication No.
US-2006-0040402-A1; U.S. Patent Publication No.
US-2006-0036142-A1; U.S. Patent Publication No.
US-2006-0036141-A1; U.S. Patent Publication No.
US-2006-0036143-A1; U.S. Patent Publication No.
US-2006-0036140-A1; U.S. Patent Publication No.
US-2006-0036139-A1; U.S. Patent Publication No.
US-2006-0142651-A1; U.S. Patent Publication No.
US-2006-0036145-A1; U.S. Patent Publication No.
US-2006-0036144-A1; U.S. Patent Publication No.
US-2006-0200022-A1; U.S. Patent Publication No.
US-2006-0198864-A1; U.S. Patent Publication No.
US-2006-0200019-A1; U.S. Patent Publication No.
US-2006-0189856-A1; U.S. Patent Publication No.
US-2006-0200020-A1; U.S. Patent Publication No.
US-2006-0200970-A1; U.S. Patent Publication No.
US-2006-0183984-A1; U.S. Patent Publication No.
US-2006-0183985-A1; U.S. Patent Publication No.
US-2006-0195029-A1; U.S. Patent Publication No.
US-2006-0229512-A1; U.S. Patent Publication No.
US-2006-0222566-A1; U.S. Patent Publication No.
US-2007-0032706-A1; U.S. Patent Publication No.
US-2007-0016381-A1; U.S. Patent Publication No.
US-2007-0027370-A1; U.S. Patent Publication No.
US-2007-0032718-A1; U.S. Patent Publication No.
US-2007-0059196-A1; U.S. Patent Publication No.
US-2007-0066873-A1; U.S. Patent Publication No.
US-2007-0197890-A1; U.S. Patent Publication No.
US-2007-0173710-A1; U.S. Patent Publication No.
US-2007-0163880-A1; U.S. Patent Publication No.
US-2007-0203966-A1; U.S. Patent Publication No.
US-2007-0213611-A1; U.S. Patent Publication No.
US-2007-0232879-A1; U.S. Patent Publication No.
US-2007-0235331-A1; U.S. Patent Publication No.
US-2008-0021666-A1; U.S. Patent Publication No.
US-2008-0033254-A1; U.S. Patent Publication No.
US-2008-0045824-A1; U.S. Patent Publication No.
US-2008-0071156-A1; U.S. Patent Publication No.
US-2008-0086042-A1; U.S. Patent Publication No.
US-2008-0086044-A1; U.S. Patent Publication No.
US-2008-0086273-A1; U.S. Patent Publication No.
US-2008-0083617-A1; U.S. Patent Publication No.
US-2008-0119703-A1; U.S. Patent Publication No.
US-2008-0119704-A1; U.S. Patent Publication No.
US-2008-0119706-A1 U.S. Patent Publication No.
US-2008-0194936-A1; U.S. Patent Publication No.
US-2008-0194937-A1; U.S. Patent Publication No.
US-2008-0183061-A1; U.S. Patent Publication No.
US-2008-0183399-A1; U.S. Patent Publication No.
US-2008-0189051-A1; U.S. Patent Publication No.
US-2008-0214918-A1; U.S. Patent Publication No.
US-2008-0194938-A1; U.S. Patent Publication No.
US-2008-0214915-A1; U.S. Patent Publication No.
US-2008-0194935-A1; U.S. Patent Publication No.
US-2008-0188731-A1; U.S. Patent Publication No.
US-2008-0242961-A1; U.S. Patent Publication No.
US-2008-0208025-A1; U.S. Patent Publication No.
US-2008-0197024-A1; U.S. Patent Publication No.
US-2008-0200788-A1; U.S. Patent Publication No.
US-2008-0200789-A1; U.S. Patent Publication No.
US-2008-0200791-A1; U.S. Patent Publication No.
US-2008-0228054-A1; U.S. Patent Publication No.
US-2008-0228051-A1; U.S. Patent Publication No.
US-2008-0262469-A1; U.S. Patent Publication No.
US-2008-0108942-A1; U.S. Patent Publication No.
US-2008-0306368-A1; U.S. Patent Publication No.
US-2009-0012379-A1; U.S. Patent Publication No.
US-2008-0287765-A1; U.S. Patent Publication No.
US-2008-0287764-A1; U.S. Patent Publication No.
US-2008-0287766-A1; U.S. Patent Publication No.
US-2008-0275313-A1; U.S. Patent Publication No.
US-2008-0296155-A1; U.S. Patent Publication No.
US-2008-0306434-A1; U.S. Patent Publication No.
US-2008-0306444-A1; U.S. Patent Publication No.
US-2008-0306435-A1; U.S. Patent Publication No.
US-2009-0018424-A1; U.S. Patent Publication No.
US-2009-0043181-A1; U.S. Patent Publication No.
US-2009-0043541-A1; U.S. Patent Publication No.
US-2009-0043542-A1; U.S. Patent Publication No.
US-2009-0043525-A1; U.S. Patent Publication No.
US-2009-0036758-A1; U.S. Patent Publication No.
US-2009-0043182-A1; U.S. Patent Publication No.
US-2009-0030294-A1; U.S. Patent Publication No.
US-2009-0036763-A1; U.S. Patent Publication No.
US-2009-0062633-A1; U.S. Patent Publication No.
US-2009-0062635-A1; U.S. Patent Publication No.
US-2009-0076361-A1; U.S. Patent Publication No.
US-2009-0076360-A1; U.S. Patent Publication No.
US-2009-0076356-A1; U.S. Patent Publication No.
US-2009-0099436-A1; U.S. Patent Publication No.
US-2009-0216103-A1; U.S. Patent Publication No.
US-2009-0137886-A1; U.S. Patent Publication No.
US-2009-0124964-A1; U.S. Patent Publication No.
US-2009-0131776-A1; U.S. Patent Publication No.
US-2009-0137887-A1; U.S. Patent Publication No.
US-2009-0131777-A1; U.S. Patent Publication No.
US-2009-0131768-A1; U.S. Patent Publication No.
US-2009-0131769-A1; U.S. Patent Publication No.
US-2009-0178459-A1; U.S. Patent Publication No.
US-2009-0192380-A1; U.S. Patent Publication No.
US-2009-0156924-A1; U.S. Patent Publication No.
US-2009-0192722-A1; U.S. Patent Publication No.
US-2009-0192366-A1; U.S. Patent Publication No.
US-2009-0192751-A1; U.S. Patent Publication No.
US-2009-0163791-A1; U.S. Patent Publication No.
US-2009-0192724-A1; U.S. Patent Publication No.
US-2009-0124879-A1; U.S. Patent Publication No.
US-2009-0163790-A1; U.S. Patent Publication No.
US-2009-0143660-A1; U.S. Patent Publication No.
US-2009-0156919-A1; U.S. Patent Publication No.
US-2009-0182217-A1; U.S. Patent Publication No.
US-2009-0203981-A1; U.S. Patent Publication No.
US-2009-0204341-A1; U.S. Patent Publication No.
US-2009-0124878-A1; U.S. Patent Publication No.
US-2009-0124877-A1; U.S. Patent Publication No.
US-2009-0143659-A1; and U.S. Patent Publication No. US-2009-0192745-A1

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 12/103,594 filed Apr. 15, 2008 and entitled "BIOINTERFACE WITH MACRO- AND MICRO-ARCHITECTURE"; U.S. patent application Ser. No. 12/055,098 filed Mar. 25, 2008 and entitled "ANALYTE SENSOR"; U.S. patent application Ser. No. 12/054,953 filed Mar. 25, 2008 and entitled "ANALYTE SENSOR"; U.S. patent application Ser. No. 12/133,789 filed Jun. 5, 2008 and entitled "INTEGRATED MEDICAMENT DELIVERY DEVICE FOR USE WITH CONTINUOUS ANALYTE SENSOR"; U.S. patent application Ser. No. 12/139,305 filed Jun. 13, 2008 and entitled "ELECTRODE SYSTEMS FOR ELECTROCHEMICAL SENSORS"; U.S. patent application Ser. No. 12/182,073 filed Jul. 29, 2008 and entitled "INTEGRATED RECEIVER FOR CONTINUOUS ANALYTE SENSOR"; U.S. patent application Ser. No. 12/260,017 filed Oct. 28, 2008 and entitled "SENSOR HEAD FOR USE WITH IMPLANTABLE DEVICES"; U.S. patent application Ser. No. 12/263,993 filed Nov. 3, 2008 and entitled "SIGNAL PROCESSING FOR CONTINUOUS ANALYTE SENSOR"; U.S. patent application Ser. No. 12/264,835 filed Nov. 4, 2008 and entitled "IMPLANTABLE ANALYTE SENSOR"; U.S. patent application Ser. No. 12/362,194 filed Jan. 29, 2009 and entitled "CONTINUOUS CARDIAC MARKER SENSOR SYSTEM"; U.S. patent application Ser. No. 12/365,683 filed Feb. 4, 2009 and entitled "CONTINUOUS MEDICAMENT SENSOR SYSTEM FOR IN VIVO USE"; U.S. patent application Ser. No. 12/390,304 filed Feb. 20, 2009 and entitled "SYSTEMS AND METHODS FOR PROCESSING, TRANSMITTING AND DISPLAYING SENSOR DATA"; U.S. patent application Ser. No. 12/390,205 filed Feb. 20, 2009 and entitled "SYSTEMS AND METHODS FOR CUSTOMIZING DELIVERY OF SENSOR DATA"; U.S. patent application Ser. No. 12/390,290 filed Feb. 20, 2009 and entitled "SYSTEMS AND METHODS FOR BLOOD GLUCOSE MONITORING AND ALERT DELIVERY"; U.S. patent application Ser. No. 12/413,231 filed Mar. 27, 2009 and entitled "POLYMER MEMBRANES FOR CONTINUOUS ANALYTE SENSORS"; U.S. patent application Ser. No. 12/413,166 filed Mar. 27, 2009 and entitled "POLYMER MEMBRANES FOR CONTINUOUS ANALYTE SENSORS"; U.S. patent application Ser. No. 12/509,396 filed Jul. 24, 2009 and entitled "SIGNAL PROCESSING FOR CONTINUOUS ANALYTE SENSOR"; U.S. patent application Ser. No. 12/536,852 filed Aug. 6, 2009 and entitled "INTEGRATED DELIVERY DEVICE FOR CONTINUOUS GLUCOSE SENSOR"; U.S. patent application Ser. No. 12/511,982 filed Jul. 29, 2009 and entitled "SILICONE BASED MEMBRANES FOR USE IN IMPLANTABLE GLUCOSE SENSORS"; and U.S. patent application Ser. No. 12/535,620 filed Aug. 4, 2009 and entitled "ANALYTE SENSOR."

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Terms and phrases used in this document, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; and adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for continuous in vivo measurement of glucose in a host, the system comprising:
    a continuous glucose sensor configured for implantation in a host and configured to measure in vivo a signal indicative of glucose concentration, wherein the continuous glucose sensor comprises an electrode, wherein the electrode comprises:
        a non-conductive material,
        conductive particles distributed within the non-conductive material, wherein each of the conductive particles has a three-dimensional electroactive surface, wherein the conductive particles comprise silver and silver chloride particles, and
        a biocompatible membrane located over at least a portion of the electrode; and
    sensor electronics operably connected to the continuous glucose sensor, wherein the sensor electronics are configured to process the signal from the continuous glucose sensor.

2. The system of claim 1, wherein the electrode comprises a plurality of sensing elements, wherein the sensor electronics are configured to determine the glucose concentration by averaging or integrating signals from the plurality of sensing elements.

3. The system of claim 2, wherein the sensing elements are spaced along a substantial length of an in vivo portion of the continuous glucose sensor.

4. The system of claim 2, wherein the plurality of sensing elements comprise more than two electroactive surfaces.

5. The system of claim 2, wherein the plurality of sensing elements comprise more than three electroactive surfaces.

6. The system of claim 2, wherein the plurality of sensing elements are spaced apart within a diffusion distance of a measured glucose.

7. The system of claim 1, wherein the electroactive surfaces all have a substantially equal area.

8. The system of claim 1, wherein the electroactive surfaces are each spaced apart from at least one adjacent electroactive surface by a substantially equal distance.

9. The system of claim 1, wherein the biocompatible membrane comprises polyurethane.

10. The system of claim 1, wherein the continuous glucose sensor has a planar shape.

11. The system of claim 1, wherein the sensor is configured to apply a bias potential from about 0.1 V to about 0.6 V.

12. The system of claim 11, wherein the sensor is configured to apply a bias potential at around 0.35 V.

13. The system of claim 1, wherein the non-conductive material is a polyurethane.

* * * * *

UNITED STATES PATENT AND TRADEMARK OFFICE
CERTIFICATE OF CORRECTION

PATENT NO. : 10,561,352 B2
APPLICATION NO. : 16/027103
DATED : February 18, 2020
INVENTOR(S) : Peter C. Simpson It is certified that error appears in the above-identified patent and that said Letters Patent is hereby corrected as shown below:

On the Title Page

On Page 7, Column 1, Item (56), Line 21, under Other Publications, delete "Miffling" and insert --Mifflin--.

On Page 7, Column 1, Item (56), Line 32, under Other Publications, delete "hypoglycaemic" and insert --hypoglycemic--.

On Page 7, Column 1, Item (56), Line 43, under Other Publications, delete "telernetry" and insert --telemetry--.

On Page 8, Column 1, Item (56), Line 50, under Other Publications, delete "your" and insert --you--.

On Page 8, Column 1, Item (56), Line 61, under Other Publications, delete "Expoxy" and insert --Epoxy--.

On Page 8, Column 2, Item (56), Line 14, under Other Publications, delete "Hypoglycaemia-" and insert --Hypoglycemia- --.

On Page 8, Column 2, Item (56), Line 41, under Other Publications, delete "sensers" and insert --sensors--.

On Page 8, Column 2, Item (56), Line 43, under Other Publications, delete "subcutaneousiy" and insert --subcutaneously--.

On Page 8, Column 2, Item (56), Line 45, under Other Publications, delete "Giliigan" and insert --Gilligan--.

On Page 8, Column 2, Item (56), Line 64, under Other Publications, delete "giucose" and insert --glucose--.

Signed and Sealed this
Second Day of June, 2020

Andrei Iancu
*Director of the United States Patent and Trademark Office*

CERTIFICATE OF CORRECTION (continued)
U.S. Pat. No. 10,561,352 B2

On Page 9, Column 1, Item (56), Line 2, under Other Publications, delete "controiled" and insert --controlled--.

On Page 9, Column 1, Item (56), Line 23, under Other Publications, delete "combinding" and insert --combining--.

On Page 9, Column 2, Item (56), Line 3, under Other Publications, delete ": i776-" and insert --: 1776- --.

On Page 9, Column 2, Item (56), Line 4, under Other Publications, delete "transcuteneous" and insert --transcutaneous--.

On Page 9, Column 2, Item (56), Line 5, under Other Publications, delete "biotelemeter" and insert --biotelemetry--.

On Page 9, Column 2, Item (56), Line 16, under Other Publications, delete "Tochnology" and insert --Technology--.

On Page 9, Column 2, Item (56), Line 26, under Other Publications, delete "giucose" and insert --glucose--.

On Page 9, Column 2, Item (56), Line 38, under Other Publications, delete "Horm" and insert --Norm--.

On Page 9, Column 2, Item (56), Line 65, under Other Publications, delete "Sensor" and insert --Sensors--.

On Page 10, Column 1, Item (56), Line 10, under Other Publications, delete "insuiin" and insert --insulin--.

On Page 10, Column 1, Item (56), Line 25, under Other Publications, delete "Electronanalysis" and insert --Electroanalysis--.

On Page 10, Column 1, Item (56), Line 44, under Other Publications, delete "artifical" and insert --artificial--.

On Page 10, Column 1, Item (56), Line 58, under Other Publications, delete "amperometeric" and insert --amperometric--.

On Page 10, Column 1, Item (56), Line 65, under Other Publications, delete "profiled" and insert --profile--.

On Page 10, Column 2, Item (56), Line 37, under Other Publications, delete "immobiiized" and insert --immobilized--.

CERTIFICATE OF CORRECTION (continued)
U.S. Pat. No. 10,561,352 B2

On Page 10, Column 2, Item (56), Line 37, under Other Publications, delete "termistor" and insert --thermistor--.

On Page 10, Column 2, Item (56), Line 38, under Other Publications, delete "metaboiites." and insert --metabolites.--.

On Page 10, Column 2, Item (56), Line 55, under Other Publications, delete "signaaldrich.com" and insert --sigmaaldrich.com--.

On Page 10, Column 2, Item (56), Line 70, under Other Publications, delete "amparometric" and insert --amperometric--.

On Page 11, Column 1, Item (56), Line 4, under Other Publications, delete "Amoerometric" and insert --Amperometric--.

On Page 11, Column 1, Item (56), Line 18, under Other Publications, delete "Implantabie" and insert --Implantable--.

On Page 11, Column 1, Item (56), Line 30, under Other Publications, delete "giucose" and insert --glucose--.

On Page 11, Column 1, Item (56), Line 55, under Other Publications, delete "anodas" and insert --anodes--.

On Page 11, Column 2, Item (56), Line 19, under Other Publications, delete "Fetrocene" and insert --Ferrocene--.

On Page 12, Column 1, Item (56), Line 31, under Other Publications, delete "Mlorosensors." and insert --Microsensors.--.

On Page 12, Column 1, Item (56), Line 36, under Other Publications, delete "microdiaiysis" and insert --microdialysis--.

On Page 12, Column 1, Item (56), Line 38, under Other Publications, delete "Pervaporatlon" and insert --Pervaporation--.

On Page 12, Column 1, Item (56), Line 45, under Other Publications, delete "pyruvnte cholesteral" and insert --pyruvate cholesterol--.

On Page 12, Column 1, Item (56), Line 47, under Other Publications, delete "1995" and insert --1995.--.

On Page 12, Column 1, Item (56), Line 51, under Other Publications, delete "all" and insert --al.--.

On Page 12, Column 1, Item (56), Line 64, under Other Publications, delete "GluoWatch" and insert --GlucoWatch--.

CERTIFICATE OF CORRECTION (continued)
U.S. Pat. No. 10,561,352 B2

On Page 12, Column 2, Item (56), Line 31, under Other Publications, delete "Diffusian" and insert --Diffusion--.

On Page 12, Column 2, Item (56), Line 33, under Other Publications, delete "biood" and insert --blood--.

On Page 12, Column 2, Item (56), Line 65, under Other Publications, delete "Technoiogy" and insert --Technology--.

On Page 13, Column 1, Item (56), Line 2, under Other Publications, delete "MetabResearch" and insert --Metab Research--.

On Page 13, Column 1, Item (56), Line 7, under Other Publications, delete "Wiison" and insert --Wilson--.

On Page 13, Column 1, Item (56), Line 25, under Other Publications, delete "Ciinica" and insert --Clinica--.

On Page 13, Column 1, Item (56), Line 27, under Other Publications, delete "Medicai" and insert --Medical--.

On Page 13, Column 1, Item (56), Line 29, under Other Publications, delete "biosenser" and insert --biosensor--.

On Page 13, Column 1, Item (56), Line 38, under Other Publications, delete "Nation" and insert --Nafion--.

In the Specification

In Column 3, Line 4, delete "1-wt%" and insert --1 wt%--.

In Column 3, Line 4, delete "60-wt%" and insert --60 wt%--.

In Column 7, Line 36, delete "dehydroxgenase;" and insert --dehydrogenase--.

In Column 7, Line 44, delete "carbamezepine," and insert --carbamazepine,--.

In Column 7, Line 45, delete "Phenytoin" and insert --Phenyloin--.

In Column 7, Lines 50-51, delete "andrenostenedione;" and insert --androstenedione;--.

In Column 7, Line 67, delete "diptheria" and insert --diphtheria--.

In Column 8, Line 7, delete "perioxidase;" and insert --peroxidase;--.

In Column 8, Line 21, delete "duodenalisa," and insert --duodenalis,--.

CERTIFICATE OF CORRECTION (continued)
U.S. Pat. No. 10,561,352 B2

In Column 8, Line 29, delete "Trepenoma pallidium," and insert --Treponema pallidum,--.

In Column 8, Line 30, delete "stomatis" and insert --stomatitis--.

In Column 8, Line 51, delete "(barbituates," and insert --(barbiturates,--.

In Column 20, Line 41, delete "IR" and insert --IIR--.

In Column 22, Line 67, delete "noise causing" and insert --noise-causing--.

In Column 24, Line 6, delete "it's" and insert --its--.

In Column 27, Line 21, delete "can by" and insert --can be--.

In Column 27, Line 50, delete "byproduct," and insert --by-product,--.

In Column 27, Line 64, delete "polyetheneterephthalate," and insert --polyethylene terephthalate,--.

In Column 37, Line 17, delete "bio stable" and insert --biostable--.

In Column 38, Line 47, delete "semipermeable" and insert --semi-permeable--.